US006552067B2

(12) United States Patent
Cameron et al.

(10) Patent No.: US 6,552,067 B2
(45) Date of Patent: Apr. 22, 2003

(54) EP4 RECEPTOR SELECTIVE AGONISTS IN THE TREATMENT OF OSTEOPOROSIS

(75) Inventors: Kimberly O. Cameron, East Lyme, CT (US); Bruce A. Lefker, Gales Ferry, CT (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 09/990,556

(22) Filed: Nov. 21, 2001

(65) Prior Publication Data

US 2002/0065308 A1 May 30, 2002

Related U.S. Application Data

(60) Provisional application No. 60/253,275, filed on Nov. 27, 2000.

(51) Int. Cl.[7] .................. C07D 207/04; A61K 31/40
(52) U.S. Cl. ............................. 514/424; 548/551
(58) Field of Search ..................... 548/551; 514/424

(56) References Cited

U.S. PATENT DOCUMENTS 4,177,346 A * 12/1979 Nelson ............... 542/427
4,320,136 A * 3/1982 Scribner ............. 424/274

FOREIGN PATENT DOCUMENTS

| EP | 1110949 | 6/2001 | ......... C07D/207/26 |
|----|---------|--------|----------------------|
| EP | 1121939 | 8/2001 | ......... A61K/45/06 |
| EP | 1132086 | 9/2001 | ....... A61K/31/4015 |
| GB | 1158163 | 7/1969 | .......... C08F/45/00 |
| GB | 1343014 | 1/1974 | .......... C07C/59/22 |
| GB | 1487842 | 10/1977 | ......... C07C/177/00 |
| GB | 1583163 | 1/1981 | ......... C07D/207/27 |
| WO | WO 0021542 | 4/2000 | .......... A61K/31/66 |

* cited by examiner

*Primary Examiner*—Joseph K. McKane
*Assistant Examiner*—Golam M.M. Shameem
(74) *Attorney, Agent, or Firm*—Peter C. Richardson; Gregg C. Benson; John A. Wichtowski

(57) ABSTRACT

This invention is directed to EP4 receptor selective prostaglandin agonists of the Formula I,

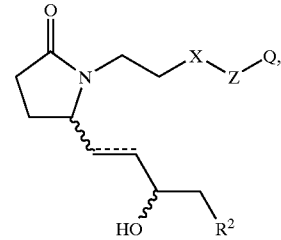

wherein $R^2$, X, Z and Q are as defined in the specification. This invention is also directed to pharmaceutical compositions containing those compounds. This invention is also directed to methods of treating conditions which present with low bone mass, particularly osteoporosis, frailty, an osteoporotic fracture, a bone defect, childhood idiopathic bone loss, alveolar bone loss, mandibular bone loss, bone fracture, osteotomy, bone loss associated with periodontitis, or prosthetic ingrowth in a mammal comprising administering those compounds.

11 Claims, No Drawings

EP4 RECEPTOR SELECTIVE AGONISTS IN THE TREATMENT OF OSTEOPOROSIS

CROSS-REFERENCE TO RELATED APPLICATIONS

The present application is a U.S. non-provisional application. This application claims the benefit of U.S. Ser. No. 60/253,275 filed on Nov. 27, 2000, under 35 USC 119(e).

BACKGROUND OF INVENTION

This invention relates to EP4 receptor selective prostaglandin agonists, combinations, methods, kits and pharmaceutical compositions comprising said prostaglandin agonists which are useful to prevent bone loss, restore or augment bone mass and to enhance bone healing including the treatment of conditions which present with low bone mass and/or bone defects in vertebrates, and particularly mammals, including humans.

Osteoporosis is a systemic skeletal disease, characterized by low bone mass and deterioration of bone tissue, with a consequent increase in bone fragility and susceptibility to fracture. In the U.S., the condition affects more than 25 million people and causes more than 1.3 million fractures each year, including 500,000 spine, 250,000 hip and 240,000 wrist fractures annually. Hip fractures are the most serious consequence of osteoporosis, with 5–20% of patients dying within one year, and over 50% of survivors being incapacitated.

The elderly are at greatest risk of osteoporosis, and the problem is therefore predicted to increase significantly with the aging of the population. Worldwide fracture incidence is forecasted to increase three-fold over the next 60 years, and one study has estimated that there will be 4.5 million hip fractures worldwide in 2050.

Women are at greater risk of osteoporosis than men. Women experience a sharp acceleration of bone loss during the five years following menopause. Other factors that increase the risk include smoking, alcohol abuse, a sedentary lifestyle and low calcium intake.

There are currently two main types of pharmaceutical therapy for the treatment of osteoporosis. The first is the use of anti-resorptive compounds to reduce the resorption of bone tissue.

Estrogen is an example of an anti-resorptive agent. It is known that estrogen reduces fractures. In addition, Black, et al. in EP 0605193A1 report that estrogen, particularly when taken orally, lowers plasma levels of LDL and raises those of the beneficial high density lipoproteins (HDL's). However, estrogen fails to restore bone back to young adult levels in the established osteoporotic skeleton. Furthermore, long-term estrogen therapy has been implicated in a variety of disorders, including an increase in the risk of uterine cancer, endometrial cancer and possibly breast cancer, causing many women to avoid this treatment. The significant undesirable effects associated with estrogen therapy support the need to develop alternative therapies for osteoporosis that have the desirable effect on serum LDL but do not cause undesirable effects.

A second type of pharmaceutical therapy for the treatment of osteoporosis is the use of anabolic agents to promote bone formation and increase bone mass. This class of agents is expected to restore bone to the established osteoporotic skeleton.

In addition to osteoporosis, approximately, 20–25 million women and an increasing number of men have detectable vertebral fractures as a consequence of reduced bone mass, with an additional 250,000 hip fractures reported yearly in America alone. The latter case is associated with a 12% mortality rate within the first two years and with a 30% rate of patients requiring nursing home care after the fracture. While this is already significant, the economic and medical consequences of convalescence due to slow or imperfect healing of these bone fractures is expected to increase, due to the aging of the general population.

Estrogens have been shown (Bolander et al., 38th Annual Meeting Orthopedic Research Society, 1992) to improve the quality of the healing of appendicular fractures. Therefore, estrogen replacement therapy should be effective as a method for the treatment of fracture repair. However, patient compliance with estrogen therapy is relatively poor due to its side effects, including the resumption of menses, mastodynia, an increased risk of uterine cancer, an increased perceived risk of breast cancer, and the concomitant use of progestins. In addition, men are likely to object to the use of estrogen treatment. The need exists for a therapy which would be beneficial to patients who have suffered debilitating bone fractures and which would increase patient compliance.

It has been demonstrated that prostaglandin E2 (PGE2) can restore lost bone in an ovariectomized (OVX) rat model, a model for postmenopausal osteoporosis. Ke, H. Z., et al., Bone, 23:249–255, 1998. However there are severe side effects associated with PGE2. Jee, W. S. S. and Ma, Y. F., Bone, 21:297–304, 1997.

Great Britain Patent Specification 1 553 595 discloses compounds of the formula

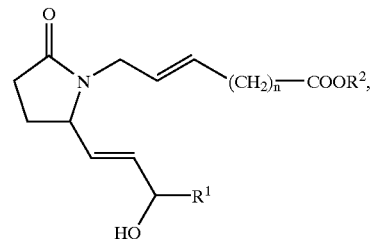

wherein the double bonds are cis or trans and the variables are defined as set forth therein. Those compounds are disclosed as having spasmogenic and spasmolytic activity, for example bronchodilatory and antihypertensive effects. The compounds are also disclosed as having utility in the inhibition of the secretion of gastric juice and as having abortive effects.

U.S. Pat. No. 4,115,401 discloses compound of the formula

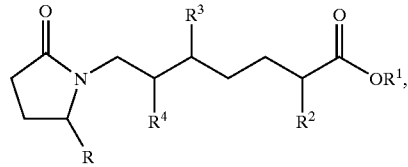

wherein the variables are defined as set forth therein. Those compounds are disclosed as having spasmogenic, cardiovascular and bronchodilatory effects.

U.S. Pat. No. 4,113,873 discloses compound of the formula

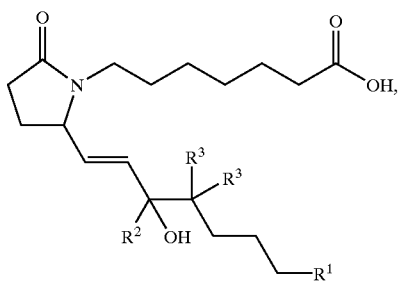

wherein the variables are defined as set forth therein. Those compounds are disclosed as having utility as a bronchodilator, as an antihypertensive agent, as an enhancer of spontaneous contraction of the uterus and for the treatment of gastrointestinal disorders or gastric ulcers.

Great Britain Patent Specification 1 583 163 discloses compounds of the formula

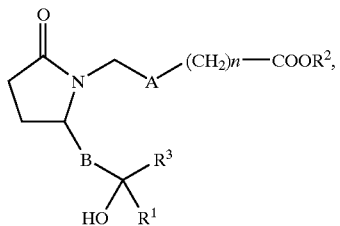

wherein the variables are defined as set forth therein. Those compounds are disclosed as having spasmogenic, bronchodilatory, vasoconstricting, vasodilating and abortive properties as well as utility in the inhibition of gastric acid secretion.

Commonly assigned U.S. Pat. No. 4,177,346 discloses compounds of the formula

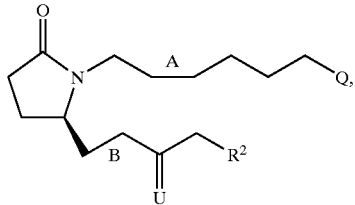

wherein the variables are defined as set forth therein. Those compounds are disclosed as having vasodilator, antihypertensive, bronchodilator, antifertility and antisecretory activity.

International Patent Application Publication No. WO00\21542 discloses that EP4 receptor subtype agonists have utility as stimulators of bone formation.

Although there are a variety of osteoporosis therapies, there is a continuing need and a continuing search in this field of art for alternative osteoporosis therapies. In addition, there is a need for bone fracture healing therapies. Also, there is a need for therapy which can promote bone re-growth into skeletal areas where defects exist such as defects caused or produced by, for example, tumors in bone. Further, there is a need for therapy which can promote bone re-growth into skeletal areas where bone graft surgery has been completed.

SUMMARY OF THE INVENTION

This invention is directed to compounds of Formula I

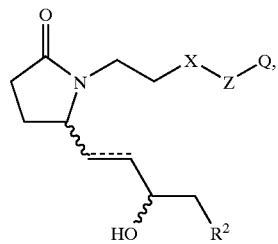

prodrugs thereof, pharmaceutically acceptable salts of said compounds and said prodrugs and stereoisomers and diastereomeric mixtures of said compounds, prodrugs and salts, wherein the dotted line is a bond or no bond; X is —$CH_2$— or O; Z is —$(CH_2)_3$—, thienyl, thiazolyl or phenyl, provided that when X is O, then Z is phenyl; Q is carboxyl, ($C_1$-$C_4$) alkoxylcarbonyl or tetrazolyl; $R^2$ is —Ar or —$Ar^1$—V—$Ar^2$; V is a bond, —O—, —$OCH_2$— or —$CH_2O$—;

Ar is a partially saturated, fully saturated or fully unsaturated five to eight membered ring optionally having one to four heteroatoms selected independently from oxygen, sulfur and nitrogen, or a bicyclic ring consisting of two fused independently partially saturated, fully saturated or fully unsaturated five or six membered rings, taken independently, optionally having one to four heteroatoms selected independently from nitrogen, sulfur and oxygen, said partially or fully saturated ring or bicyclic ring optionally having one or two oxo groups substituted on carbon or one or two oxo groups substituted on sulfur; and $Ar^1$ and $Ar^2$ are each independently a partially saturated, fully saturated or fully unsaturated five to eight membered ring optionally having one to four heteroatoms selected independently from oxygen, sulfur and nitrogen, said partially or fully saturated ring optionally having one or two oxo groups substituted on carbon or one or two oxo groups substituted on sulfur;

said Ar moiety is optionally substituted on carbon or nitrogen, on one ring if the moiety is monocyclic, or on one or both rings if the moiety is bicyclic, with up to three substituents per ring each independently selected from hydroxy, halo, carboxy, ($C_1$-$C_7$)alkoxy, ($C_1$-$C_4$) alkoxy($C_1$-$C_4$)alkyl, ($C_1$-$C_7$)alkyl, ($C_2$-$C_7$)alkenyl, ($C_3$-$C_7$)cycloalkyl, ($C_3$-$C_7$)cycloalkyl($C_1$-$C_4$)alkyl, ($C_3$-$C_7$)cycloalkyl($C_1$-$C_4$)alkanoyl, formyl, ($C_1$-$C_8$) alkanoyl, ($C_1$-$C_6$)alkanoyl($C_1$-$C_6$)alkyl, ($C_1$-$C_4$) alkanoylamino, ($C_1$-$C_4$)alkoxycarbonylamino, hydroxysulfonyl, aminocarbonylamino or mono-N-, di-N,N-, di-N,N'- or tri-N,N,N'-($C_1$-$C_4$)alkyl substituted aminocarbonylamino, sulfonamido, ($C_1$-$C_4$) alkylsulfonamido, amino, mono-N- or di-N,N-($C_1$-$C_4$) alkylamino, carbamoyl, mono-N- or di-N,N-($C_1$-$C_4$) alkylcarbamoyl, cyano, thiol, ($C_1$-$C_6$)alkylthio, ($C_1$-$C_6$)alkylsulfinyl, ($C_1$-$C_4$)alkylsulfonyl and mono-N- or di-N,N-($C_1$-$C_4$)alkylaminosulfinyl, wherein said alkyl and alkoxy substituents in the definition of Ar are optionally substituted on carbon with up to three fluoro;

said $Ar^1$ and $Ar^2$ moieties are independently optionally substituted on carbon or nitrogen with up to three substituents each independently selected from hydroxy, halo, carboxy, ($C_1$-$C_7$)alkoxy, ($C_1$-$C_4$)alkoxy($C_1$-$C_4$) alkyl, ($C_1$-$C_7$)alkyl, ($C_2$-$C_7$)alkenyl, ($C_3$-$C_7$)

cycloalkyl, $(C_3-C_7)$cycloalkyl$(C_1-C_4)$alkyl, $(C_3-C_7)$ cycloalkyl$(C_1-C_4)$alkanoyl, formyl, $(C_1-C_8)$alkanoyl, $(C_1-C_6)$alkanoyl$(C_1-C_6)$alkyl, $(C_1-C_4)$alkanoylamino, $(C_1-C_4)$alkoxycarbonylamino, hydroxysulfonyl, aminocarbonylamino or mono-N-, di-N,N-, di-N,N'- or tri-N,N,N'-$(C_1-C_4)$alkyl substituted aminocarbonylamino, sulfonamido, $(C_1-C_4)$ alkylsulfonamido, amino, mono-N- or di-N,N-$(C_1-C_4)$ alkylamino, carbamoyl, mono-N- or di-N,N-$(C_1-C_4)$ alkylcarbamoyl, cyano, thiol, $(C_1-C_6)$alkylthio, $(C_1-C_6)$alkylsulfinyl, $(C_1-C_4)$alkylsulfonyl and mono-N- or di-N,N-$(C_1-C_4)$alkylaminosulfinyl, wherein said alkyl and alkoxy substituents in the definition of $Ar^1$ and $Ar^2$ are optionally substituted on carbon with up to three fluoro;

provided that (a) when X is $(CH_2)$— and Z is —$(CH_2)_3$—, then $R^2$ is not thienyl, phenyl or phenyl monosubstituted with chloro, fluoro, phenyl, methoxy, trifluoromethyl or $(C_1-C_4)$alkyl; and (b) when X is $(CH_2)$—, Z is —$(CH_2)_3$—, and Q is carboxyl or $(C_1-C_4)$alkoxycarbonyl, then $R^2$ is not (i) $(C_5-C_7)$cycloalkyl or (ii) phenyl, thienyl or furyl each of which may be optionally monosubstituted or disubstituted by one or two substituents selected, independently in the latter case, from halogen atoms, alkyl groups having 1–3 carbon atoms which may be substituted by one or more halogen atoms, and alkoxy groups having 1–4 carbon atoms.

A preferred group of compounds, designated Group A, are those compounds of the Formula Ia,

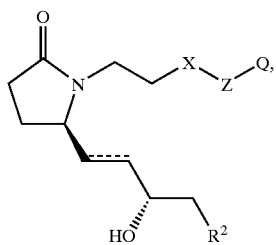

Ia prodrugs thereof, pharmaceutically acceptable salts of said compounds and said prodrugs, and stereoisomers and diastereomeric mixtures of said compounds, prodrugs and salts, wherein: X is —$CH_2$—; Z is —$(CH_2)_3$—,

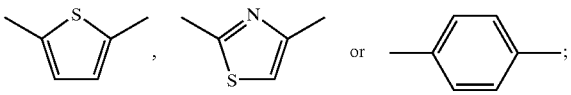

and $R^2$ is Ar wherein said Ar moiety is optionally substituted on carbon or nitrogen, on one ring if the moiety is monocyclic, or on one or both rings if the moiety is bicyclic, with up to three substituents per ring each independently selected from hydroxy, halo, carboxy, $(C_1-C_7)$alkoxy, $(C_1-C_4)$alkoxy$(C_1-C_4)$alkyl, $(C_1-C_7)$alkyl, $(C_2-C_7)$alkenyl, $(C_3-C_7)$cycloalkyl, $(C_3-C_7)$cycloalkyl$(C_1-C_4)$alkyl, $(C_3-C_7)$cycloalkyl$(C_1-C_4)$alkanoyl, formyl, $(C_1-C_8)$ alkanoyl, $(C_1-C_6)$alkanoyl$(C_1-C_6)$alkyl, $(C_1-C_4)$ alkanoylamino, $(C_1-C_4)$alkoxycarbonylamino, hydroxysulfonyl, aminocarbonylamino or mono-N-, di-N, N-, di-N,N'- or tri-N,N,N'-$(C_1-C_4)$alkyl substituted aminocarbonylamino, sulfonamido, $(C_1-C_4)$ alkylsulfonamido, amino, mono-N- or di-N,N-$(C_1-C_4)$ alkylamino, carbamoyl, mono-N- or di-N,N-$(C_1-C_4)$ alkylcarbamoyl, cyano, thiol, $(C_1-C_6)$alkylthio, $(C_1-C_6)$ alkylsulfinyl, $(C_1-C_4)$alkylsulfonyl and mono-N- or di-N, N-$(C_1-C_4)$alkylaminosulfinyl, wherein said alkyl and alkoxy substituents in the definition of Ar are optionally substituted on carbon with up to three fluoro.

A preferred group of compounds within Group A, designated Group B, are those compounds, prodrugs thereof, pharmaceutically acceptable salts of said compounds and said prodrugs, and stereoisomers and diastereomeric mixtures of said compounds, prodrugs and salts wherein Ar is cyclohexyl, 1,3-benzodioxolyl, thienyl, naphthyl or phenyl optionally substituted with one or two $(C_1-C_4)$alkyl, $(C_1-C_4)$alkoxy, $(C_1-C_4)$alkoxy$(C_1-C_4)$alkyl, chloro, fluoro, trifluoromethyl or cyano, wherein said alkyl and alkoxy substituents in the definition of Ar are optionally substituted with up to three fluoro.

A preferred group of compounds within Group B, designated Group C, are those compounds, prodrugs thereof, pharmaceutically acceptable salts of said compounds and said prodrugs, and stereoisomers and diastereomeric mixtures of said compounds, prodrugs and salts wherein the dotted line is no bond; Q is carboxy or $(C_1-C_4)$ alkoxylcarbonyl; and Z is

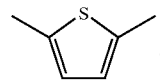

A preferred group of compounds within Group C, designated Group D, are those compounds, prodrugs thereof and pharmaceutically acceptable salts of said compounds and said prodrugs, and stereoisomers and diastereomeric mixtures of said compounds, prodrugs and salts wherein Q is carboxy and Ar is phenyl optionally substituted with one $(C_1-C_4)$alkyl, $(C_1-C_4)$alkoxy, $(C_1-C_4)$alkoxy$(C_1-C_4)$alkyl, chloro, fluoro, trifluoromethyl or cyano, wherein said alkyl and alkoxy substituents in the definition of Ar are optionally substituted with up to three fluoro.

A preferred compound within Group D is the compound, prod rugs thereof and pharmaceutically acceptable salts of said compound and said prodrugs, and stereoisomers and diastereomeric mixtures of said compound, prodrugs and salts wherein Ar is m-trifluoromethylphenyl.

Another preferred compound within Group D is the compound, prodrugs thereof and pharmaceutically acceptable salts of said compound and said prodrugs, and stereoisomers and diastereomeric mixtures of said compound, prodrugs and salts wherein Ar is m-chlorophenyl.

Another preferred compound within Group D is the compound, prodrugs thereof and pharmaceutically acceptable salts of said compound and said prodrugs, and stereoisomers and diastereomeric mixtures of said compound, prodrugs and salts wherein Ar is m-trifluoromethoxyphenyl.

An especially preferred group of compounds of this invention include 5-(3-(2S-(3R-hydroxy-4-(3-trifluoromethyl-phenyl)-butyl)-5-oxo-pyrrolidin-1-yl)-propyl)-thiophene-2-carboxylic acid; 5-(3-(2S-(3R-hydroxy-4-(3-trifluoromethoxy-phenyl)-butyl)-5-oxo-pyrrolidin-1-yl)-propyl)-thiophene-2-carboxylic acid; and 5-(3-(2S-(4-(3-chloro-phenyl)-3R-hydroxy-butyl)-5-oxo-pyrrolidin-1-yl)-propyl)-thiophene-2-carboxylic acid.

Another preferred group of compounds within Group A are those compounds of Group A, pharmaceutically acceptable salts of said compounds and said prodrugs and stereoisomers and diatereomeric mixtures of said compounds, prodrugs and salts, wherein X is —$CH_2$—, Z is —$(CH_2)_3$—, Q is carboxyl or $(C_1-C_4)$alkoxycarbonyl and Ar is phenyl independently substituted with one to three cyano, $(C_1-C_7)$ alkoxy substituted with one to three fluoro or $(C_1-C_4)$alkoxy $(C_1-C_4)$alkyl.

This invention is particularly directed to a compound of Formula I as defined in the immediately preceeding paragraph, pharmaceutically acceptable salts of said compounds and said prodrugs and stereoisomers and diatereomeric mixtures of said compounds, prodrugs and salts, wherein the dotted line is no bond; Q is carboxy or ($C_1$–$C_4$) alkoxylcarbonyl; and Z is

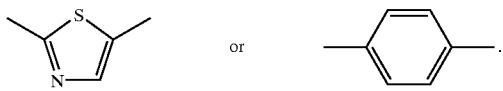

This invention is particularly directed to a compound of Formula I as defined in the immediately preceeding paragraph, a prodrug thereof, pharmaceutically acceptable salts of said compounds and said prodrugs and stereoisomers and diatereomeric mixtures of said compounds, prodrugs and salts, wherein Q is carboxy and Ar is phenyl optionally substituted with one ($C_1$–$C_4$)alkyl, ($C_1$–$C_4$)alkoxy, ($C_1$–$C_4$) alkoxy($C_1$–$C_4$)alkyl, chloro, fluoro, trifluoromethyl or cyano, wherein said alkyl and alkoxy substituents in the definition of Ar are optionally substituted with up to three fluoro.

This invention is further directed to methods of treating a condition which presents with low bone mass in a mammal comprising administering to said mammal an EP4 receptor selective compound of Formula I, a prodrug thereof or a pharmaceutically acceptable salt of said compound or said prodrug, or a stereoisomer or diastereomeric mixture of said compound, salt or prodrug.

This invention is particularly directed to such methods wherein said condition is osteoporosis, frailty, an osteoporotic fracture, a bone defect, childhood idiopathic bone loss, alveolar bone loss, mandibular bone loss, bone fracture, osteotomy, bone loss associated with periodontitis, or prosthetic ingrowth. In preferred methods of this invention, the EP4 receptor selective agonist is administered systemically. In other preferred methods of this invention, the EP4 agonist is administered locally.

This invention is particularly directed to such methods wherein such condition is a metastable bone disease wherein surgical removal of bone leaves a bone defect which requires filling.

The methods of this invention are especially useful wherein said condition is frailty.

The methods of this invention are also especially useful wherein said condition is osteoporosis.

The methods of this invention are also especially useful wherein said condition is bone fracture or osteoporotic fracture.

This invention is also directed to pharmaceutical compositions comprising a compound of Formula I, a prodrug thereof, a pharmaceutically acceptable salt of said compound or said prodrug, or a stereoisomer or diastereomeric mixture of said compound, prodrug or salt of this invention and a pharmaceutically acceptable carrier, vehicle or diluent. This invention is also directed to methods of treating a condition which presents with low bone mass in a mammal comprising administering to said mammal such a pharmaceutical composition.

Preferably post-menopausal women and men over the age of 60 are treated. Also preferred are individuals regardless of age who have significantly reduced bone mass, i.e., greater than or equal to 1.5 standard deviations below young normal levels.

In the methods of this invention, conditions which present with low bone mass include such conditions as, for example, osteoporosis, childhood idiopathic bone loss, alveolar bone loss, mandibular bone loss, bone fracture, osteotomy, bone loss associated with periodontitis and prosthetic ingrowth.

Methods for treating "secondary osteoporosis" are also included within the methods of this invention. "Secondary osteoporosis" includes glucocorticoid-induced osteoporosis, hyperthyroidism-induced osteoporosis, immobilization-induced osteoporosis, heparin-induced osteoporosis and immunosuppressive-induced osteoporosis in a vertebrate, e.g., a mammal (including a human being). These methods are carried out by administering to said vertebrate, e.g., mammal, a "secondary osteoporosis" treating amount of an EP4 receptor selective prostaglandin agonist of Formula I, a prodrug thereof or a pharmaceutically acceptable salt of said EP4 receptor selective prostaglandin agonist or of said prodrug or a stereoisomer or diastereomeric mixture of said compound, prodrug or salt.

Yet another aspect of this invention is directed to methods for strengthening a bone graft, inducing vertebral synostosis, enhancing long bone extension, enhancing bone healing following facial reconstruction, maxillary reconstruction and/or mandibular reconstruction in a vertebrate, e.g., a mammal (including a human being), comprising administering to said vertebrate, e.g., a mammal which has undergone bone graft surgery, induction of vertebral synostosis, enhancement of long bone extension, facial reconstruction, maxillary reconstruction or mandibular reconstruction, a bone enhancing amount of an EP4 receptor selective prostaglandin agonist of Formula I, a prodrug thereof or a pharmaceutically acceptable salt of said EP4 receptor selective prostaglandin agonist or of said prodrug, or a stereoisomer or diastereomeric mixture of said compound, prodrug or salt. The EP4 receptor selective prostaglandin agonists of this invention may be applied locally to the site of bone reconstruction or may be administered systemically.

This invention is also directed to a method of treating impotence or erectile dysfunction which comprises administering to a patient in need of such treatment an impotence or erectile dysfunction treating amount of a compound of Formula I, a prodrug thereof, a pharmaceutically acceptable salt of said compound or said prodrug or a stereoisomer or diastereomeric mixture of said compound, prodrug or salt.

This invention is also directed to a method for treating a mammal which presents with impaired renal function comprising administering to said mammal a kidney regenerating effective amount of a compound of Formula I, a prodrug thereof, a pharmaceutically acceptable salt of said compound or said prodrug or a stereoisomer or diastereomeric mixture of said compound, prodrug or salt.

This invention is also directed to methods of promoting bone growth comprising administering to a mammal a therapeutically effective amount of a compound of Formula I, a prodrug thereof, a pharmaceutically acceptable salt of said compound or said prodrug or a stereoisomer or diastereomeric mixture of said compound, prodrug or salt; and a therapeutically effective amount of a HMG-CoA reductase inhibitor (statin) or a prodrug thereof or a pharmaceutically acceptable salt of said compound or said prodrug.

A preferred dosage is about 0.001 to about 100 mg/kg/day of a compound of Formula I, a prodrug thereof or a pharmaceutically acceptable salt of said compound or said prodrug, or a stereoisomer or a diastereomeric mixture of said compound, prodrug or salt. An especially preferred dosage is about 0.01 to about 10 mg/kg/day of a compound of Formula I, a prodrug thereof or a pharmaceutically acceptable salt of said compound or said prodrug, or a stereoisomer or a diastereomeric mixture of said compound, prodrug or salt.

Yet another aspect of this invention is directed to combinations of a Formula I compound, a prodrug thereof or a pharmaceutically acceptable salt of said compound or of said prodrug, or a stereoisomer or diastereomeric mixture of said compound, prodrug or salt, and other compounds as described below.

Yet another aspect of this invention is directed to pharmaceutical compositions comprising a compound of Formula I, a prodrug thereof or a pharmaceutically acceptable salt of said compound or said prodrug, or a stereoisomer or diastereomeric mixture of said compound, prodrug or salt, and an anti-resorptive agent, a prodrug thereof or a pharmaceutically acceptable salt of said agent or said prodrug and for the use of such compositions for the treatment or prevention of conditions which present with low bone mass, including osteoporosis in a vertebrates, e.g., mammals (e.g., humans, particularly women) or the use of such compositions for other bone mass augmenting uses.

The combinations of this invention comprise a therapeutically effective amount of a first compound, said first compound being a Formula I compound, a prodrug thereof or a pharmaceutically acceptable salt of said compound or said prodrug, or a stereoisomer or diastereomeric mixture of said compound, prodrug or salt; and a therapeutically effective amount of a second compound, said second compound being an anti-resorptive agent, a prodrug thereof or a pharmaceutically acceptable salt of said agent or said prodrug such as an estrogen agonist/antagonist or a bisphosphonate.

Another aspect of this invention is directed to methods for treating vertebrates, e.g., mammals which present with low bone mass comprising administering to said vertebrate, e.g., a mammal having a condition which presents with low bone mass a. an amount of a first compound, said first compound being a Formula I compound, a prodrug thereof or a pharmaceutically acceptable salt of said compound or said prodrug, or a stereoisomer or diastereomeric mixture of said compound, prodrug or salt; and b. an amount of a second compound, said second compound being an anti-resorptive agent, a prodrug thereof or a pharmaceutically acceptable salt of said agent or said prodrug such as an estrogen agonist/antagonist or a bisphosphonate.

Such compositions and methods may also be used for other bone mass augmenting uses.

A preferred aspect of this method is wherein the condition which presents with low bone mass is osteoporosis.

Another preferred aspect of this method is wherein the first compound and the second compound are administered substantially simultaneously.

Another aspect of this invention is a kit comprising:

a. an amount of a Formula I compound, a prodrug thereof or a pharmaceutically acceptable salt of said compound or said prodrug, or a stereoisomer or diastereomeric mixture of said compound, prodrug or salt and a pharmaceutically acceptable carrier or diluent in a first unit dosage form;

b. an amount of an anti-resorptive agent, a prodrug thereof or a pharmaceutically acceptable salt of said agent or said prodrug such as an estrogen agonist/antagonist or a bisphosphonate and a pharmaceutically acceptable carrier or diluent in a second unit dosage form; and c. a container.

Yet another aspect of this invention is directed to pharmaceutical compositions comprising a compound of Formula I, a prodrug thereof or a pharmaceutically acceptable salt of said compound or said prodrug, or a stereoisomer or diastereomeric mixture of said compound, prodrug or salt, and another bone anabolic agent (although the other bone anabolic agent may be a different Formula I compound), a prodrug thereof or a pharmaceutically acceptable salt of said agent or said prodrug and for the use of such compositions for the treatment of conditions which present with low bone mass, including osteoporosis in a vertebrates, e.g., mammals (e.g., humans, particularly women), or the use of such compositions for other bone mass augmenting uses. Such compositions comprise a therapeutically effective amount of a first compound, said first compound being a Formula I compound, a prodrug thereof or a pharmaceutically acceptable salt of said compound or said prodrug or a stereoisomer or diastereomeric mixture of said compound, prodrug or salt; and a therapeutically effective amount of a second compound, said second compound being another bone anabolic agent, a prodrug thereof or a pharmaceutically acceptable salt of said agent or said prodrug.

Another aspect of this invention is directed to methods for treating vertebrates, e.g., mammals which present with low bone mass comprising administering to said vertebrate, e.g., a mammal having a condition which presents with low bone mass a. an amount of a first compound, said first compound being a Formula I compound, a prodrug thereof or a pharmaceutically acceptable salt or prodrug therof, or a stereoisomer or diastereomeric mixture of said compound, prodrug or salt; and b. an amount of a second compound, said second compound being another bone anabolic agent, a prodrug thereof or a pharmaceutically acceptable salt of said agent or said prodrug.

Such compositions and methods may also be used for other bone mass augmenting uses.

A preferred aspect of this method is wherein the condition which presents with low bone mass is osteoporosis.

Another aspect of this invention is a kit comprising:

a. an amount of a Formula I compound, a prodrug thereof or a pharmaceutically acceptable salt of said compound or said prodrug, or a stereoisomer or diastereomeric mixture of said compound, prodrug or salt, and a pharmaceutically acceptable carrier or diluent in a first unit dosage form;

b. an amount of a second compound, said second compound being another bone anabolic agent, a prodrug thereof or a pharmaceutically acceptable salt of said agent or said prodrug in a second unit dosage form; and c. a container.

Where used in any of the above methods, kits and compositions, certain bone anabolic agents, estrogen agonists/antagonists and bisphosphonates are preferred or especially preferred.

Preferred bone anabolic agents include IGF-1, prostaglandins, prostaglandin agonists/antagonists, sodium fluoride, parathyroid hormone (PTH), active fragments of parathyroid hormone, parathyroid hormone related peptides and active fragments and analogues of parathyroid hormone related peptides, growth hormones or growth hormone secretagogues and the pharmaceutically acceptable salts thereof.

Preferred estrogen agonists/antagonists include droloxifene, raloxifene, tamoxifen; 4-hydroxy-tamoxifen; toremifene; centchroman; levormeloxifene; idoxifene; 6-(4-hydroxy-phenyl)-5-(4-(2-piperidin-1-yl-ethoxy)-benzyl)-naphthalen-2-ol; (4-(2-(2-aza-bicyclo[2.2.1]hept-2-yl)- ethoxy)-phenyl)-(6-hydroxy-2-(4-hydroxy-phenyl)-benzo[b]thiophen-3-yl)-methanone;

3-(4-(1,2-diphenyl-but-1-enyl)-phenyl)-acrylic acid;
2-(4-methoxy-phenyl)-3-[4-(2-piperidin-1-yl-ethoxy)-phenoxy]-benzo[b]thiophen-6-ol;
cis-6-(4-fluoro-phenyl)-5-(4-(2-piperidin-1-yl-ethoxy)-phenyl)-5,6,7,8-tetrahydro-naphthalene-2-ol;
(−)-cis-6-phenyl-5-(4-(2-pyrrolidin-1-yl-ethoxy)-phenyl)-5,6,7,8-tetrahydro-naphthalene-2-ol (lasofoxifene);
cis-6-phenyl-5-(4-(2-pyrrolidin-1-yl-ethoxy)-phenyl)-5,6,7,8-tetrahydro-naphthalene-2-ol;
cis-1-(6'-pyrrolodinoethoxy-3'-pyridyl)-2-phenyl-6-hydroxy-1,2,3,4-tetrahydronaphthalene;
1-(4'-pyrrolidinoethoxyphenyl)-2-(4"-fluorophenyl)-6-hydroxy-1,2,3,4-tetrahydroisoquinoline;
cis-6-(4-hydroxyphenyl)-5-(4-(2-piperidin-1-yl-ethoxy)-phenyl)-5,6,7,8-tetrahydro-naphthalene-2-ol; and
1-(4'-pyrrolidinolethoxyphenyl)-2-phenyl-6-hydroxy-1,2,3,4-tetrahydroisoquinoline and the pharmaceutically acceptable salts thereof.

Especially preferred estrogen agonists/antagonists include:
3-(4-(1,2-diphenyl-but-1-enyl)-phenyl)-acrylic acid;
2-(4-methoxy-phenyl)-3-[4-(2-piperidin-1-yl-ethoxy)-phenoxy]-benzo[b]thiophen-6-ol;
cis-6-(4-fluoro-phenyl)-5-(4-(2-piperidin-1-yl-ethoxy)-phenyl)-5,6,7,8-tetrahydro-naphthalene-2-ol;
(−)-cis-6-phenyl-5-(4-(2-pyrrolidin-1-yl-ethoxy)-phenyl)-5,6,7,8-tetrahydro-naphthalene-2-ol (lasofoxifene);
cis-6-phenyl-5-(4-(2-pyrrolidin-1-yl-ethoxy)-phenyl)-5,6,7,8-tetrahydro-naphthalene-2-ol;
cis-1-(6'-pyrrolodinoethoxy-3'-pyridyl)-2-phenyl-6-hydroxy-1,2,3,4-tetrahydronaphthalene;
1-(4'-pyrrolidinoethoxyphenyl)-2-(4"-fluorophenyl)-6-hydroxy-1,2,3,4-tetrahydroisoquinoline;
cis-6-(4-hydroxyphenyl)-5-(4-(2-piperidin-1-yl-ethoxy)-phenyl)-5,6,7,8-tetrahydro-naphthalene-2-ol;
1-(4'-pyrrolidinolethoxyphenyl)-2-phenyl-6-hydroxy-1,2,3,4-tetrahydroisoquinoline; and the pharmaceutically acceptable salts thereof.

Preferred bisphosphonates include, tiludronic acid, alendronic acid, zoledronic acid, ibandronic acid, risedronic acid, etidronic acid, clodronic acid, and pamidronic acid and their pharmaceutically acceptable salts.

It will be recognized that prodrugs and pharmaceutically acceptable salts may be formed from the compounds used as the second compounds in the combinations of this invention. All of such prodrugs and pharmaceutically acceptable salts so formed are within the scope of this invention. Particularly preferred salt forms include raloxifene hydrochloride, tamoxifen citrate and toremifene citrate.

The phrase "condition(s) which presents with low bone mass" refers to a condition where the level of bone mass is below the age specific normal as defined in standards by the World Health Organization "Assessment of Fracture Risk and its Application to Screening for Postmenopausal Osteoporosis (1994). Report of a World Health Organization Study Group. World Health Organization Technical Series 843". Included in "condition(s) which presents with low bone mass" are primary and secondary osteoporosis, as described above. Also included is periodontal disease, alveolar bone loss, post-osteotomy and childhood idiopathic bone loss. The phrase "condition(s) which presents with low bone mass" also includes long term complications of osteoporosis such as curvature of the spine, loss of height and prosthetic surgery.

The phrase "condition(s) which presents with low bone mass" also refers to a vertebrate, e.g., a mammal, known to have a significantly higher than average chance of developing such diseases as are described above including osteoporosis (e.g., post-menopausal women, men over the age of 50). Other bone mass augmenting or enhancing uses include bone restoration, increasing the bone fracture healing rate, replacing bone graft surgery entirely, enhancing the rate of successful bone grafts, bone healing following facial reconstruction or maxillary reconstruction, mandibular reconstruction, long bone reconstruction, prosthetic ingrowth, vertebral synostosis or long bone extension.

The methods of this invention may also be used in conjunction with orthopedic devices such as spinal fusion cages, spinal fusion hardware, internal and external bone fixation devices, screws and pins.

Those skilled in the art will recognize that the term bone mass actually refers to bone mass per unit area which is sometimes (although not strictly correctly) referred to as bone mineral density.

The term "treating", "treat" or "treatment" as used herein includes preventative (e.g., prophylactic), palliative and curative treatment.

By "pharmaceutically acceptable" it is meant the carrier, vehicle, diluent, excipients, and/or salt must be compatible with the other ingredients of the formulation, and not deleterious to the recipient thereof.

The expression "prodrug" refers to compounds that are drug precursors which, following administration, release the drug in vivo via some chemical or physiological process (e.g., a prodrug on being brought to the physiological pH or through enzyme action is converted to the desired drug form). Exemplary prodrugs upon cleavage release the corresponding drug compound.

The expression "pharmaceutically acceptable salt" refers to nontoxic anionic salts containing anions such as, but not limited to, chloride, bromide, iodide, sulfate, bisulfate, phosphate, acetate, maleate, fumarate, oxalate, lactate, tartrate, citrate, gluconate, methanesulfonate and 4-toluenesulfonate. The expression also refers to nontoxic cationic salts such as, but not limited to, sodium, potassium, calcium, magnesium, ammonium or protonated benzathine (N,N'-dibenzylethylenediamine), choline, ethanolamine, diethanolamine, ethylenediamine, meglamine (N-methylglucamine), benethamine (N-benzylphenethylamine), piperazine or tromethamine (2-amino-2-hydroxymethyl-1,3-propanediol).

The chemist of ordinary skill in the art will also recognize that certain compounds of formula I of this invention can exist in tautomeric form, i.e., that an equilibrium exists between two isomers which are in rapid equilibrium with each other. A common example of tautomerism is keto-enol tautomerism, i.e.,

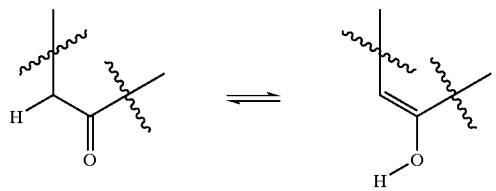

Examples of compounds which can exist as tautomers include hydroxypyridines, hydroxypyrimidines and hydroxyquinolines. Other examples will be recognized by those skilled in the art. All such tautomers and mixtures thereof are included in this invention.

The subject invention also includes isotopically-labeled compounds, which are identical to those recited in Formula I, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, sulfur, fluorine and chlorine, such as $^2$H, $^3$H, $^3$C, $^{14}$C, $^{15}$N, $^{18}$O, $^{17}$O, $^{31}$P, $^{32}$P, $^{35}$S, $^{18}$F and $^{36}$Cl, respectively. Compounds of Formula I of the present invention, prodrugs thereof, and pharmaceutically acceptable salts of said compounds and said prodrugs, and stereoisomers and diastereomeric mixtures of said compounds, prodrugs and salts, which contain the aforementioned isotopes and/or other isotopes of other atoms are within the scope of this invention. Certain isotopically-labeled compounds of the present invention, for example those into which radioactive isotopes such as $^3$H and $^{14}$C are incorporated, are useful in drug and/or substrate tissue distribution assays. Tritiated, i.e., $^3$H, and carbon-14, i.e., $^{14}$C, isotopes are particularly preferred for their ease of preparation and detectability. Further, substitution with heavier isotopes such as deuterium, i.e., $^2$H, can afford certain therapeutic advantages resulting from greater metabolic stability, for example increased in vivo half-life or reduced dosage requirements and, hence, may be preferred in some circumstances. Isotopically labeled compounds of Formula I of this invention and prodrugs thereof can generally be prepared by carrying out the procedures disclosed in the Schemes and/or in the Examples and Preparations below, by substituting a readily available isotopically labeled reagent for a non-isotopically labeled reagent.

The compounds of Formula I of this invention have asymmetric carbon atoms and therefore are enantiomers or diastereomers. Diasteromeric mixtures can be separated into their individual diastereomers on the basis of their physical chemical differences by methods known per se, for example, by chromatography and/or fractional crystallization. Enantiomers can be separated by converting the enantiomeric mixture into a diastereomeric mixture by reaction with an appropriate optically active compound (e.g., alcohol), separating the diastereomers and converting (e.g., hydrolyzing) the individual diastereomers to the corresponding pure enantiomers. Enantiomers and diastereomers of this invention can also be prepared by utilizing suitable enantiomerically enriched starting materials, or by asymmetric or diastereoselective reactions to introduce asymmetric carbon atoms with the correct stereochemistry. All such isomers, including diastereomers, enantiomers and mixtures thereof are considered as part of this invention. Some of the compounds of this invention are acidic and they form a salt with a pharmaceutically acceptable cation. All such salts are within the scope of this invention and they can be prepared by conventional methods. For example, they can be prepared simply by contacting the acidic and basic entities, usually in a stoichiometric ratio, in either an aqueous, non-aqueous or partially aqueous medium, as appropriate. The salts are recovered either by filtration, by precipitation with a non-solvent followed by filtration, by evaporation of the solvent, or, in the case of aqueous solutions, by lyophilization, as appropriate.

The methods of this invention result in bone formation resulting in decreased fracture rates. This invention makes a significant contribution to the art by providing methods that increase bone formation resulting in prevention, retardation, and/or regression of osteoporosis and related bone disorders.

Other features and advantages will be apparent from the description and claims which describe the invention.

DETAILED DESCRIPTION OF THE INVENTION

In general, the compounds of Formula I of this invention (hereinafter collectively referred to as "the compounds of this invention") are made by processes which include processes analogous to those known in the chemical arts. These processes include methods which may require protection of remote functionality (e.g., primary amine, secondary amine, secondary alcohol, primary alcohol, carboxyl in Formula I precursors). The need for such protection will vary depending upon the nature of the remote functionality and the conditions of the preparation methods. The need for such protection is readily determined by one skilled in the art. The use of such protection/deprotection methods is also within the skill in the art. The term "protecting group," where used herein, refers to a radical which may be attached to a functional group on a substrate which is easily attached and easily removed without affecting other functional groups of the substrate and which prevents the protected functional group from being removed, altered or otherwise destroyed. For a general description of protecting groups and their use, see Greene, T. W.; Wuts, P. G. M., Protective Groups in Organic Synthesis, $2^{nd}$ ed.; John Wiley and Sons Inc.: New York, 1991. The starting materials and reagents for the above described compounds are also readily available or can be easily synthesized by those skilled in the art using conventional methods of organic synthesis in light of this disclosure.

In general, compounds of Formula I are prepared by protection of the hydroxyl group of either racemic or (R)-hydroxymethyl-2-pyrrolidinone, followed by alkylation of the amide nitrogen with an alkyl halide which contains a suitably protected acid precursor or isostere (Scheme A). The term "isostere," where used herein, refers to a functional group which, when used in place of another functional group, approximates the reactivity of the functional group which it replaces. In some cases, the alkyl halide must be further elaborated to install the suitably protected acid precursor or isostere (Scheme B1). The hydroxyl protecting group is removed, the alcohol oxidized to the aldehyde which is then reacted with the anion of a suitable ketophosphonate (Scheme C). The resulting enone of formula 8 of Scheme E is then subjected to reduction of both the double bond and ketone to give the desired saturated alcohols of formula 9 of Scheme E. If desired, a diastereoselective reduction of the enone can be effected to give, for example, predominantly the 15-(R) isomer or the 15-(S) isomer. The carboxylic ester or precursor to an acid isostere (e.g., nitrile) is then converted into the appropriate acidic group (carboxylic acid, tetrazole, etc).

A preferred method for converting a nitrile into the desired tetrazole is treatment of the nitrile with dibutyltin oxide and trimethylsilylazide, in refluxing toluene (S. J. Wittenberger and B. G. Donner, J. Org. Chem. 1993, 58, 4139–4141, 1993). For a review of alternative preparations of tetrazoles see R. N. Butler, Tetrazoles, in Comprehensive Heterocyclic Chemistry; Potts, K. T. Ed.; Pergamon Press: Oxford, 1984, Vol. 5, pp 791–838.

Scheme A

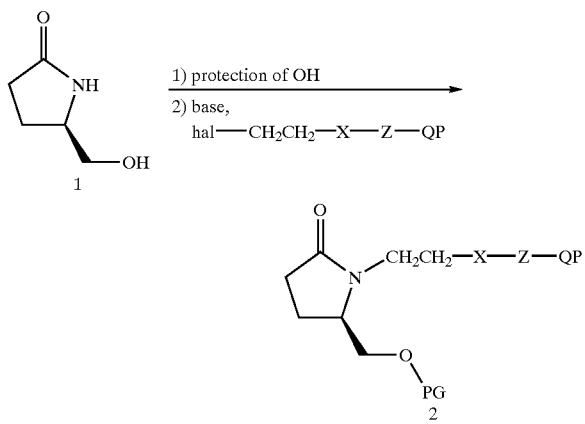

More specifically, compounds of Formula I are prepared by the following procedures. In the first general sequence, which begins with Scheme A, the hydroxyl group of 5-(R)-hydroxymethyl-2-pyrrolidinone (Aldrich Chemical, or prepared as described by Bruckner et al., Acta. Chim. Hung. Tomus, 21, 106 (1959)) is suitably protected (where PG is a suitable protecting group) by reaction of a compound of formula 1 in a reaction inert solvent. As used herein, the expressions "reaction inert solvent" and "inert solvent" refer to a solvent or mixture of solvents which does not interact with starting materials, reagents, intermediates or products in a manner which adversely affects the yield of the desired product. In some cases herein, a list of preferred reaction inert solvents is described. However, any solvent which meets the above definition of reaction inert solvent for a particular reaction may be used in that reaction. All reactions are carried out in a reaction inert solvent unless specifically stated otherwise. Any standard alcohol protecting group may be utilized, including tetrahydropyranyl, trimethylsilyl, tert-butyl-dimethylsilyl, or benzyl. A preferred protecting group is tert-butyl-dimethylsilyl (TBS), which can be installed by standard methods as described in Greene, T. W.; Wuts, P. G. M., Protective Groups in Organic Synthesis, $2^{nd}$ ed.; John Wiley and Sons Inc.: New York, 1991. It is preferred to treat 5-(R)-hydroxymethyl-2-pyrrolidinone in methylene chloride at 0° C. with 0.1 eq of 4-dimethylaminopyridine, 1.1 eq. of tert-butyl-dimethylsilylchloride, and 2 eq. of imidazole (see, e.g., Tetrahedron Asymmetry, 7, 2113, (1996)). The amide nitrogen is alkylated with one of a variety of alkylating agents (hal-$CH_2CH_2$—X—Z—QP, where hal is a leaving group such as bromide or iodide, X and Z are as described in the Summary, and QP is a nitrile, carboxylic acid ester or other precursor to a carboxylic acid or acid isostere) to introduce the desired side chain. The amide nitrogen is first deprotonated with a suitable base. Preferred bases include sodium hexamethyldisilazide (also referred to herein as NaHMDS or NaN(SiMe$_3$)$_2$) or sodium hydride in a reaction inert solvent such as N,N-dimethylformamide (DMF), tetrahydrofuran (THF), 1,2-dimethoxyethane or 1,4-dioxane. A preferred solvent is DMF. The appropriate temperature range for anion formation is between −78° C. and the temperature at which the solvent refluxes. A preferred temperature for this reaction is about 0° C. After formation of the anion, the alkylating agent (hal-$CH_2CH_2$—X—Z—QP) is added and the solution is stirred at an appropriate temperature. The appropriate temperature range for alkylation is between −20° C. and the temperature at which the solvent refluxes. The preferred temperature range for this reaction is between 0° C. and 100° C. Typical alkylating agents are primary, secondary, benzylic, propargyllic halides and primary, secondary, benzylic or propargyllic sulfonates. Preferred alkylating agents are alkyl bromides or alkyl iodides.

Many of the useful alkylating agents of the formula hal-$CH_2CH_2$—X—Z—QP are commercially available. For example, ethyl-7-bromoheptanoate and 7-bromoheptanonitrile may be obtained from Aldrich Chemical, P.O. Box 355, Milwaukee, Wis. 53201, USA. Numerous methods known to those skilled in the art exist for the synthesis of those and other desired alkylating agents used in the above Scheme (see, e.g., "The Chemistry of the Carbon-Halogen Bond," Ed. S. Patai, J. Wiley, New York, 1973 and/or "The Chemistry of Halides, Pseudo-Halides, and Azides," Eds. S. Patai and Z. Rappaport, J. Wiley, New York, 1983).

Alkyl halides are also prepared by halogenation of an alcohol or an alcohol derivative. Alkyl chlorides are typically prepared from the alcohols with reagents such as hydrogen chloride, thionyl chloride, phosphorous pentachloride, phosphorous oxychloride or triphenylphosphine/carbon tetrachloride in a reaction inert solvent. For the preparation of alkyl bromides the alcohol is commonly treated with reagents such as hydrogen bromide, phosphorous tribromide, triphenylphosphine/bromine or carbonyldiimidazole/allyl bromide in a reaction inert solvent. To prepare alkyl iodides, the alcohol is typically reacted with reagents such as triphenylphosphine/iodine/imidazole or hydrogen iodide in a reaction inert solvent. Alkyl chlorides are converted to the more reactive alkyl bromides or alkyl iodides by treatment with an inorganic salt such as sodium bromide, lithium bromide, sodium iodide or potassium iodide in a reaction inert solvent such as acetone or methyl ethyl ketone. Alkyl sulfonates are also used as electrophiles or are converted to alkyl halides. Sulfonates are prepared from the alcohol using a mild base such as triethylamine or pyridine and a sulfonyl chloride in a reaction inert solvent such a methylene chloride or diethyl ether. Conversion to the halide is accomplished by treatment of the alkyl sulfonate with an inorganic halide (sodium iodide, sodium bromide, potassium iodide, potassium bromide, lithium chloride, lithium bromide, etc) or a tetrabutylammonium halide in a reaction inert solvent.

Alkyl halides of the formula hal-$CH_2CH_2$—X—Z—QP where X is $CH_2$ and Z is phenyl, thienyl or thiazolyl are also prepared as shown in Scheme B1. For example, propargyl alcohol is treated with a compound of formula 14 of Scheme B1 containing the suitably protected acid isostere (hal-Z—QP), where the "hal-Z" group is an aryl bromide, iodide or triflate, in the presence of copper (I) iodide; a palladium catalyst such as palladium chloride, bis(triphenylphosphine) palladium dichloride or tetrakis(triphenylphosphine) palladium(0); and an amine such as triethylamine, diisopropylamine or butylamine in a reaction inert solvent, preferably an aprotic solvent such as acetonitrile, at a temperature of about 0° C. to about 100° C. For additional references, see Tetrahedron, 40, 1433 (1984) and Org. Lett. 2, 12, 1729 (2000). The resulting alkynes are then converted to the corresponding alkanes via hydrogenation in the presence of a palladium or platinum catalyst in a reaction inert solvent such as methanol, ethanol and/or ethyl acetate at a temperature of about 0° C. to about 50° C. The alcohol portion of the molecule is replaced with a suitable leaving group such as bromide or iodide For the preparation of alkyl bromides, the alcohol is commonly treated with reagents such as hydrogen bromide, phosphorous tribromide, triphenylphosphine/ bromine or carbonyldiimidazole/allyl bromide. The use of carbonyldiimidazole/allyl bromide is preferred. To prepare alkyl iodides, the alcohol is typically reacted with a reagent such as triphenylphosphine/iodine/imidazole or hydrogen iodide in a reaction inert solvent. Alkyl chlorides are converted to the more reactive alkyl bromides or alkyl iodides by treatment with an inorganic salt such as sodium bromide, lithium bromide, sodium iodide or potassium iodide in a reaction inert solvent such as acetone or methyl ethyl ketone. Alkyl sulfonates can be used as electrophiles or are converted to alkyl halides. Alkyl sulfonates are prepared from the corresponding alcohol using a mild base such as triethylamine or pyridine and a sulfonyl chloride in a reaction inert solvent such as methylene chloride or diethyl ether. Conversion to the halide is accomplished by treating the alkyl sulfonate with an inorganic halide such as, for example, sodium iodide, sodium bromide, potassium iodide, potassium bromide, lithium chloride or lithium bromide in a reaction inert solvent. Conversion to the halide may also be accomplished by treating the alkyl sulfonate with an organic ammonium halide such as tetrabutylammonium halide in a reaction inert solvent. Alkyl chlorides are typically prepared from the alcohols with reagents such as hydrogen chloride, thionyl chloride, phosphorous pentachloride, phosphorous oxychloride, or triphenylphosphine/carbon tetrachloride.

Scheme B1

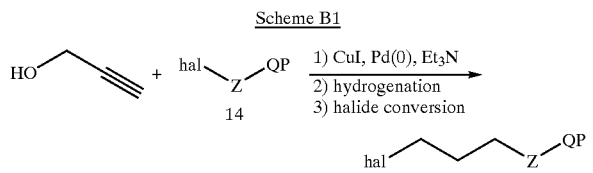

In some cases, as shown in Scheme B2, it is preferred to first alkylate with propargyl bromide or iodide, and then further elaborate to introduce the suitably protected acid precursor or isostere. For example, where the alkylating agent is propargyl bromide or iodide, compounds of Formula 3 of Scheme B2 are treated with compounds of Formula 14 of Scheme B2 containing the suitably protected acid precursor or isostere (hal-Z—QP), where the "hal-Z" group is an aryl bromide, iodide or triflate, in the presence of copper (I) iodide; a palladium catalyst such as palladium chloride, bis(triphenylphosphine)palladium dichloride or tetrakis(triphenylphosphine) palladium(0); and an amine such as triethylamine, diisopropylamine or butylamine in a reaction inert solvent, preferably an aprotic solvent such as acetonitrile, at a temperature of about 0° C. to about 100° C. For additional references see Tetrahedron, 40, 1433 (1984) and Org. Lett. 2,12,1729 (2000). The resulting alkynes are then converted to the corresponding alkanes via hydrogenation in the presence of a palladium or platinum catalyst in a reaction inert solvent such as methanol, ethanol and/or ethyl acetate at a temperature of about 0° C. to about 50° C.

Scheme B2

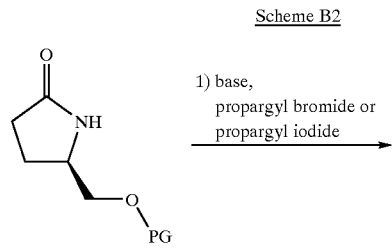

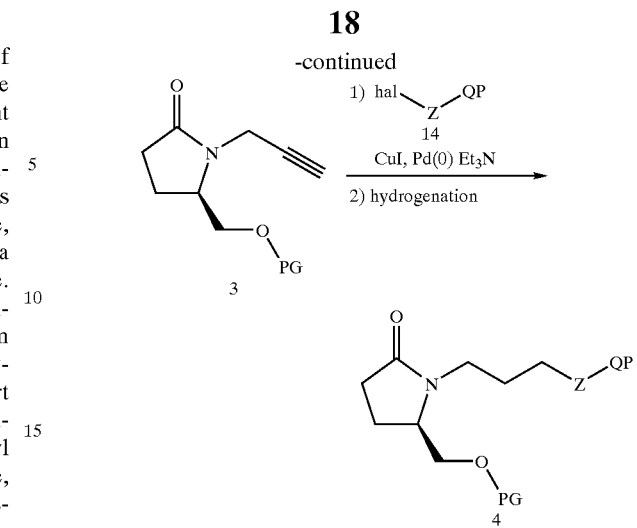

Halo-arylesters and halo-arylnitriles of Formula 14 of Scheme B2 are prepared by methods known to those skilled in the art. For example, 2-bromo-4-(ethoxycarbonyl)thiazole is prepared according to the procedure described in J. Org. Chem. 61, 14, 4623, (1996); and 2-bromo-5-(ethoxycarbonyl)thiazole is prepared according to the procedure described in Helv. Chim. Acta, 25, 1073, (1942). Other halo-arylesters and halo-arylnitriles of Formula 14 of Scheme B2 which are useful in the procedures of this invention, such as, inter alia, ethyl-4-bromobenzoate and 4-bromobenzonitrile are commercially available. Ethyl-2-bromo-thiophene-5-carboxylate is prepared by esterification of commercially available 2-bromo-thiophene-5-carboxylic acid.

The alcohol protecting groups of compounds of Formula 2 of Scheme A or Formula 4 of Scheme B2 are then removed. For a general description of methods for deprotection of protected alcohols, see Greene, T. W.; Wuts, P. G. M., Protective Groups in Organic Synthesis, $2^{nd}$ ed.; John Wiley and Sons Inc.: New York, 1991. Removal of the tert-butyl-dimethylsilyl group in compounds of Formula 2 and Formula 4 of Scheme B2 is preferably accomplished by treating the compound with tetrabutylammonium fluoride or trifluoroacetic acid in a reaction inert solvent, preferably in a suitable aprotic solvent at a temperature of about of −30° C. to about ambient temperature. Where used herein, the term "ambient temperature" refers to the temperature of the immediate, unaltered surroundings of the reaction mixture. Ambient temperature is generally between 20° C. and 25° C. An especially preferred solvent is methylene chloride. A preferred temperature range is between 0° C. to ambient temperature. Another preferred method to remove the TBS group is by treatment of the silyl ether with an aqueous solution of a mineral acid in a protic solvent. In this case, it is preferred that the silyl ether is treated with a 1N aqueous solution of hydrochloric acid in methanol at ambient temperature. Subsequent to deprotection, the alcohols are oxidized to the aldehyde by use of a modification of the Pfitzner Moffatt oxidation [K. E. Pfitzner and M. E. Moffatt, J. Am. Chem. Soc., 87, 5661 (1965)] which minimizes racemization by avoiding contact with water. For example, oxidation of the alcohol to the aldehyde is achieved by stirring the alcohol in a reaction inert solvent, preferably a hydrocarbon solvent such as toluene, xylene or, preferably, benzene, with dimethyl sulfoxide, a weak acid such as acetic acid or, preferably, pyridinium trifluoroacetate, and a diimide such as diethyl carbodiimide or, preferably, dimethylaminopropylethylcarbodiimide or, if desired, dimethylaminopropylethylcarbodiimide hydrochloride, at temperatures of about 0° C. to about ambient temperature for about one to about four hours. Alternate methods to achieve oxidation while minimizing racemization of the asymmetric center adjacent to the resulting aldehyde are discussed in detail in Tetrahedron Letters, 41, 1359, (2000) and include the usual Pfitzner-Moffatt reaction, oxidation with chromium trioxide-pyridine complex [J. Org. Chem., 35, 4000 (1970)], oxidation with Dess-Martin reagent [J. Org. Chem. 48, 4155, (1983)] or oxidation with TEMPO-bleach [Tetrahedron Letters 33, 5029, (1992)].

The resulting aldehyde is preferably subjected without purification to a Horner-Wittig reaction with the sodium or lithium salt of a phosphonate of Formula 7 of Scheme C (R is lower alkyl, haloalkyl or aryl). The sodium or lithium salts are pre-formed by prior treatment of the phosphonates with a suitable base such as sodium hydride or $NaN(SiMe_3)_2$ in a suitable reaction inert solvent, preferably an aprotic ethereal solvent at a temperature of about 0° C. to about 50° C. A preferred solvent is THF and a preferred temperature is ambient temperature. A solution of the aldehyde is then added to the salt of the phosphonate in a reaction inert solvent, preferably an aprotic solvent at a temperature of about 0° C. to about 50° C. to give enones of Formula 8 of Scheme C. A preferred solvent is THF. A preferred temperature is ambient temperature.

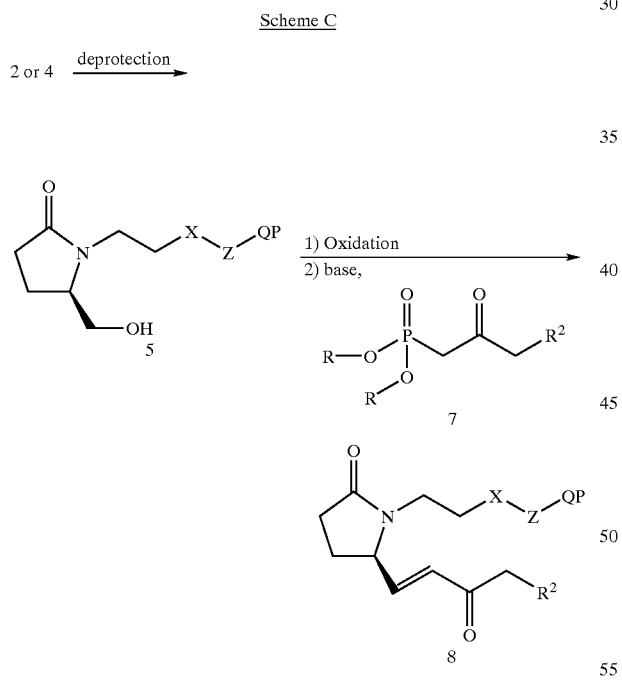

Methods for the preparation of phosphonates of Formula 7 of Scheme C1 can be found in U.S. Pat. Nos. 3,932,389; 4,177,346; Tetrahedron Lett., 30, 36, 4787–4790, (1989); and Angew.Chem., 108, 3, 366–369, (1996). In general, as shown in Scheme C1, the phosphonates of Formula 7 are prepared from reaction of the appropriately substituted arylacetic acid esters or the methoxymethyl amide of the arylacetic acid with th elithium reagent derived from a dialkyl methylphosphonate. These methods are also applicable to cycloalkylacetic esters and methoxymethylamides such as ethyl-cyclohexylacetate and ethyl-cyclopentylacetate. The aryl- and cycloalkyl-acetic acid esters are prepared by esterification of the corresponding acetic acid by methods known to those skilled in the art. The methoxymethylamides are prepared by a standard amide bond forming reaction between the corresponding acetic acid and methoxymethyl amine. Preferably the coupling of the amine with the carboxylic acid is carried out in a reaction inert solvent such as dichloromethane or DMF by a coupling reagent such as 1-(3-dimethylaminopropyl-3-ethylcarbodiimide hydrochloride (EDC) or 1,3-dicyclohexylcarbodiimide (DCC) in the presence of an acid activating agent such as 1-hydroxybenzotriazole hydrate (HOBT) to generate the methoxymethyl amide. In the case where the amine is present as the hydrochloride salt, it is preferable to add one equivalent of a suitable base such as triethylamine to the reaction mixture. Alternatively, coupling of the amine with the carboxylic acid is effected with a coupling reagent such as benzotriazol-1-yloxy-tris(dimethylamino)-phosphonium hexafluorophosphate (BOP) in a reaction inert solvent such as methanol. Such coupling reactions are generally conducted at temperatures of about −30° C. to about 80° C., preferably about 0° C. to about 25° C. For a discussion of other conditions used for amide couplings, see HeubenWeyl, Vol. XV, part 11, E. Wunsch, Ed., George Theime Verlag, 1974, Stuttgart.

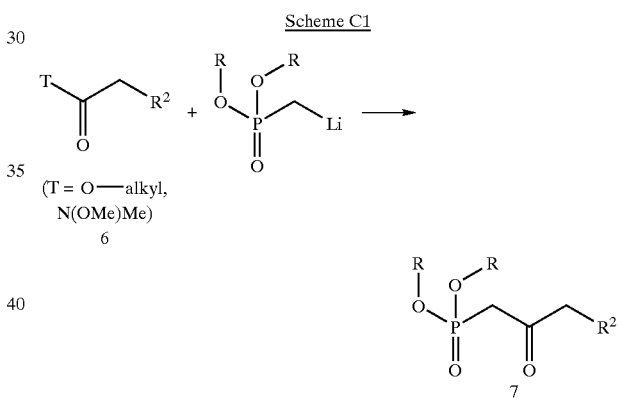

The requisite arylacetic acids and esters of Formula 6 of Scheme C1 are commercially available or are prepared by methods well known to those skilled in the art. As shown in Scheme C2, many aryl and heteroaryl substituted aryl acetic acids are prepared by Suzuki couplings of the appropriate arylboronic acids or arylboronate esters with the desired aryl halides (for a review of the Suzuki coupling reaction see A. R. Martin and Y. Yang in Acta Chem. Scand. 1993, 47, 221 or J. Am. Chem. Soc., 2000, 122, 17, 4020). For example, the 3-pinacolboronate ester of ethyl-3-bromophenylacetate is prepared using the method described by Masuda et al. in J. Org. Chem., 65, 164 (2000). Said 3-pinacolboronate ester of ethyl-3-bromophenylacetate is then coupled with the desired aryl halide to give the desired 3-aryl-phenylacetic acid (see Synlett., 6, 829 (2000)). Hydroxy substituted aryl acetic esters are alkylated with alkyl halides and benzylic halides by methods well known to those skilled in the art.

Scheme C2

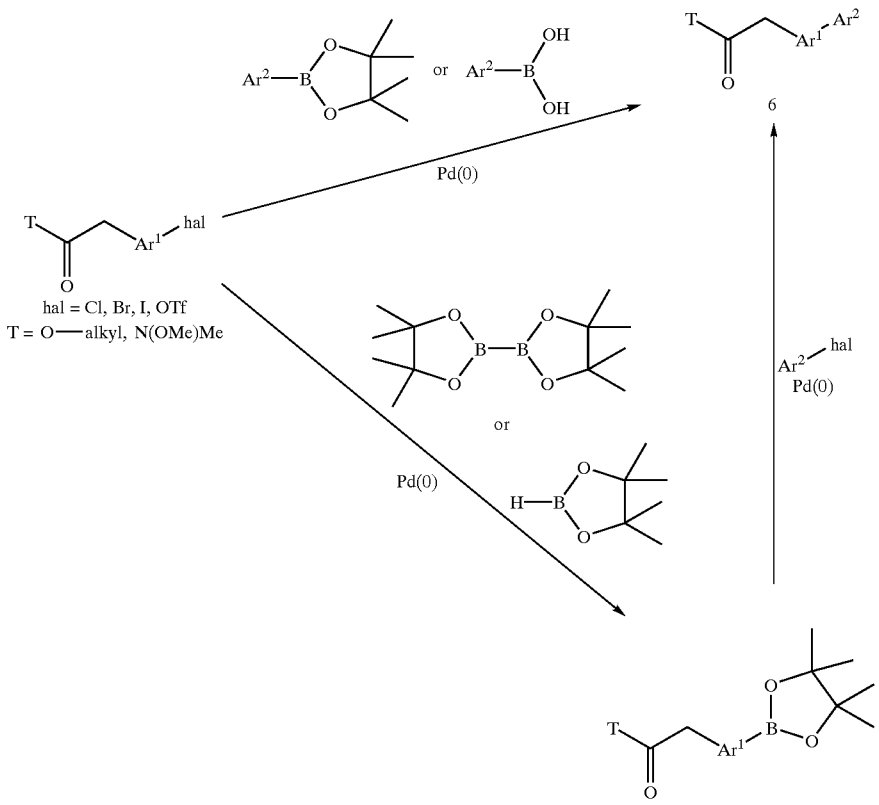

For a review of the preparation of diaryl ethers, see Angew. Chem., Int. Ed., 38, 16, 2345, (1999). Aryl acetic acids substituted with an alkylether linkage are prepared using Mitsunobu conditions (for a review see Synthesis, 1, (1981)). Typically, the coupling between a phenolic component and a benzylic alcohol is achieved by addition of triphenylphosphine and diethyl azodicarboxylate or diisopropyl azodicarboxylate in a reaction inert solvent such as methylene chloride or THF.

Alternatively, phosphonates of Formula 7 of Scheme D are prepared as shown in Scheme D. In general, triethylphosphite is added slowly to epibromo- or epichlorohydrin (10) at a temperature of about 135° C. As the triethylphosphite is added, the temperature drops to about 105° C. The reaction mixture is refluxed overnight and the product, a compound of formula 11, is isolated by vacuum distillation (see Phosphorus, Sulfur Silicon Relat. Elem., 165, 71 (1992) or U.S. Pat. No. 2,627,521). The required Grignard solutions are prepared from the appropriate aryl halides according to procedures well known to those skilled in the art in a reaction inert solvent, preferably an ethereal solvent such as THF and cooled to approximately −30° C. Catalytic copper (I) iodide is added followed by addition of the epoxide of Formula 11 [Phosphorus, Sulfur Silicon Relat. Elem., 105, 45 (1995)]. The requisite aryl halides (e.g., 3-bromo-biphenyl) are commercially available or are prepared by methods well known to those skilled in the art.

The resulting alcohols are then oxidized, preferably using a Swern oxidation [Synthesis, pp. 165–185, (1981)] or Dess-Martin reagent [J. Org. Chem. 48, 4155, (1983)]. Alternative oxidation procedures such as Pfitzner-Moffatt reaction, chromium trioxide-pyridine complex [R. Ratcliffe, et al., J. Org. Chem., 35, 4000 (1970)], TEMPO-bleach [Tet. Lett. 33, 5029, (1992)], Jones oxidation, Manganese dioxide, pyridiniumchlorochromate or pyridinium dichromate may also be utilized to prepare keto-phosphonates of Formula 7 of Scheme D, Scheme D

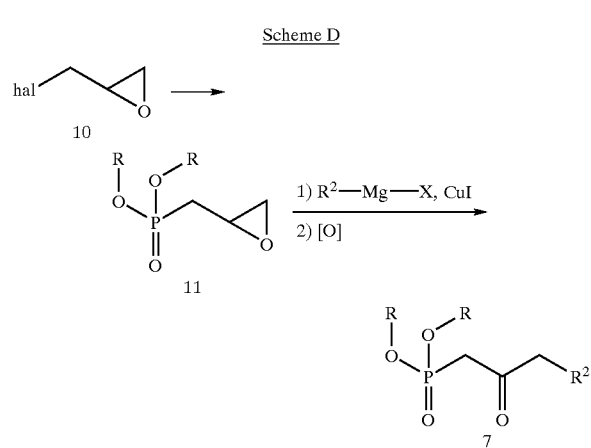

An enone of Formula 8 of Scheme E (which may also be prepared as shown in Scheme C) is reduced to a mixture of alcohol diastereomers of Formula 9 of Scheme E by methods well known to those skilled in the art. In general, the double bond of the enone is first reduced by catalytic hydrogenation. It is preferred that the double bond is reduced by hydrogenation over a noble metal catalyst such as palladium on carbon or platinum oxide in a reaction inert solvent such as ethyl acetate, methanol or ethanol at ambient temperature to about the reflux temperature of the solvent being used under 1–4 atmospheres of hydrogen. The resulting ketone is then treated with a reducing agent, preferably sodium borohydride, in a protic solvent, preferably ethanol or methanol, to give alcohols of Formula 9 of Scheme E. Other selective reduction reagents well known to those skilled in the art which will reduce the ketone but no other groups, e.g. zinc borohydride or lithium triethylborohydride may be employed with equal facility. The temperature selection will be based upon the activity of the reducing agent and will preferably be between about 0° C. to ambient temperature. If desired, the mixture of alcohols of Formula 9 may be separated by preparative chromatography or HPLC to give the desired 15-(R) diastereomer.

In an alternative sequence shown in Scheme E, an enone of Formula 8 of Scheme E is first treated with a hydride reducing agent in the presence of a chiral catalyst. Where used herein, the term "hydride reducing agent" refers to compounds which are able to reduce a compound having a higher oxidation state by transferring hydrogen to the compound. A preferred hydride reducing agent is catecholborane. A preferred chiral catalyst for performing such reactions enantioselectively is (R)-2-methyl-CBS-oxazaborolidine reagent (Aldrich Chemical Co.) (see the method described in Eur. J. Org. Chem., 2655 (1999)). The reduction is carried out in a reaction inert solvent, preferably an aprotic solvent such as methylene chloride, at a temperature of about −100° C. to ambient temperature. A preferred temperature for this reaction is about −40° C. Alternative methods and catalysts which are utilized to effect stereoselective reduction of the enone carbonyl are described in J. Am. Chem. Soc., 117, 2675, (1995); J. Am. Chem. Soc., 101, 5843, (1979); Tett. Lett., 31, 611, (1990); U.S. Pat. No. 6,037,505; and Angew. Chem. Int. Ed., 37, 1986, (1998). The double bond of the allylic alcohol is then reduced. It is preferred that the double bond is reduced by hydrogenation over a noble metal catalyst such as palladium on carbon or platinum oxide in a reaction inert solvent such as ethyl acetate, methanol or ethanol at ambient temperature to the reflux temperature of the solvent being used under 1–4 atmospheres of hydrogen.

Scheme E

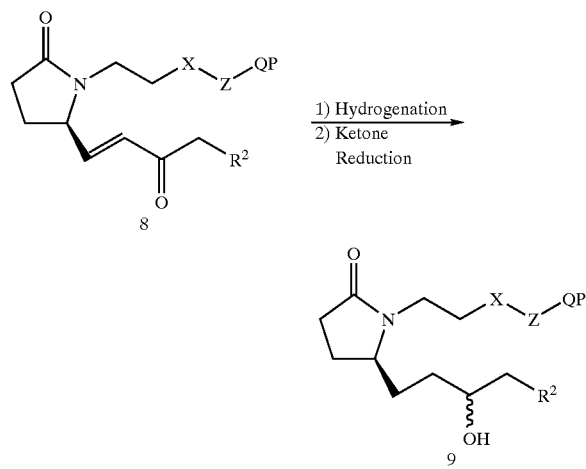

or

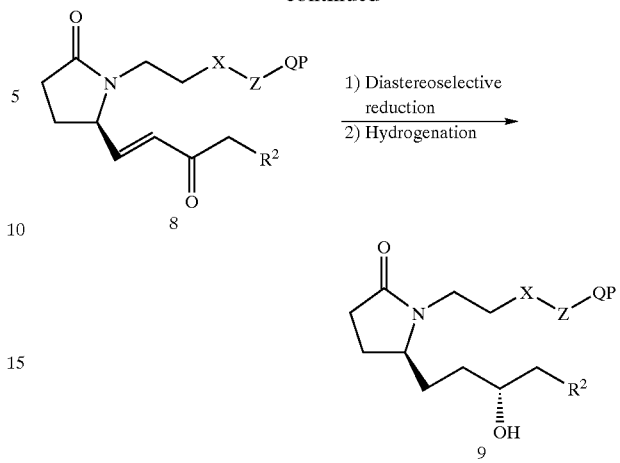

An alternative procedure for the preparation of compounds of formula 9 of Scheme F is shown in Scheme F. In general, tetrahydro-pyrrolizine-3,5-dione (the compound of formula 12 of Scheme F) is prepared as described in U.S. Pat. No. 4,663,464 or J.Med.Chem. 30; 3; 498–503; (1987). The compound of Formula 12 of Scheme F is then dissolved in a reaction inert solvent, preferably an aprotic solvent at a suitable temperature. It is preferred that said compound is dissolved in methylene chloride at about 0C. The reaction mixture is then treated with the appropriate Grignard reagent (for additional references on addition of Grignard reagents to Formula 12 of Scheme F, see Synth.Commun., 18, 1, 37–44, (1988); Helv.Chim.Acta, 70, 2003–2010, (1987)). The reaction may be warmed to ambient temperature to effect complete reaction. The resulting ketone is then treated with a reducing agent, preferably sodium borohydride in a protic solvent, preferable ethanol or methanol. Other selective reducing reagents which will reduce the ketone but no other groups, e.g., zinc borohydride or lithium triethylborohydride, can be employed with equal facility. The temperature selection will be based upon the activity of the reducing agent, preferably from about 0° C. to ambient temperature. The resulting hydroxyl group is then suitably protected. Standard alcohol protecting groups such as tetrahydropyranyl, trimethylsilyl, tert-butyl-dimethylsilyl or benzyl may be utilized. A preferred protecting group is tert-butyl-dimethylsilyl which is installed by standard methods as described in Greene, T. W.; Wuts, P. G. M., Protective Groups in Organic Synthesis, 2$^{nd}$ ed.; John Wiley and Sons Inc.: New York, 1991. Preferred conditions for this reaction include treating the alcohol in DMF at ambient temperature with 0.1 eq of 4-dimethylaminopyridine, 1.1 eq. of tert-butyl-dimethylsilylchloride and 2 eq. of imidazole.

The resulting compound of Formula 13 of Scheme F is then alkylated on nitrogen with one of a variety of alkylating agents of the formula hal-CH$_2$CH$_2$—X—QP to introduce the desired side chain. The amide nitrogen is first deprotonated with a suitable base in a reaction inert solvent. Preferred bases for this reaction include NaN(SiMe$_3$)$_2$ or sodium hydride in a solvent such as DMF, tetrahydrofuran, dimethoxyethane or dioxane. An especially preferred solvent is DMF. The appropriate temperature range for anion formation is between −78° C. and about the temperature at which the solvent refluxes. It is preferred that the reaction is conducted at ambient temperature. After formation of the anion, the alkylating agent of the formula hal-CH$_2$CH$_2$—X—QP is added, and the solution is stirred at a temperature between −20° C. to about the temperature at which the solvent refluxes. A preferred temperature is between ambient temperature and 100° C. Typical alkylating agents include primary halides and primary sulfonates. Preferably, an alkyl bromide or alkyl iodide is used. The alcohol protecting group is then removed by methods well known to those skilled in the art (see Greene, T. W.; Wuts, P. G. M., Protective Groups in Organic Synthesis, $2^{nd}$ ed.; John Wiley and Sons Inc.: New York, 1991) to produce compounds of Formula 9.

Scheme F

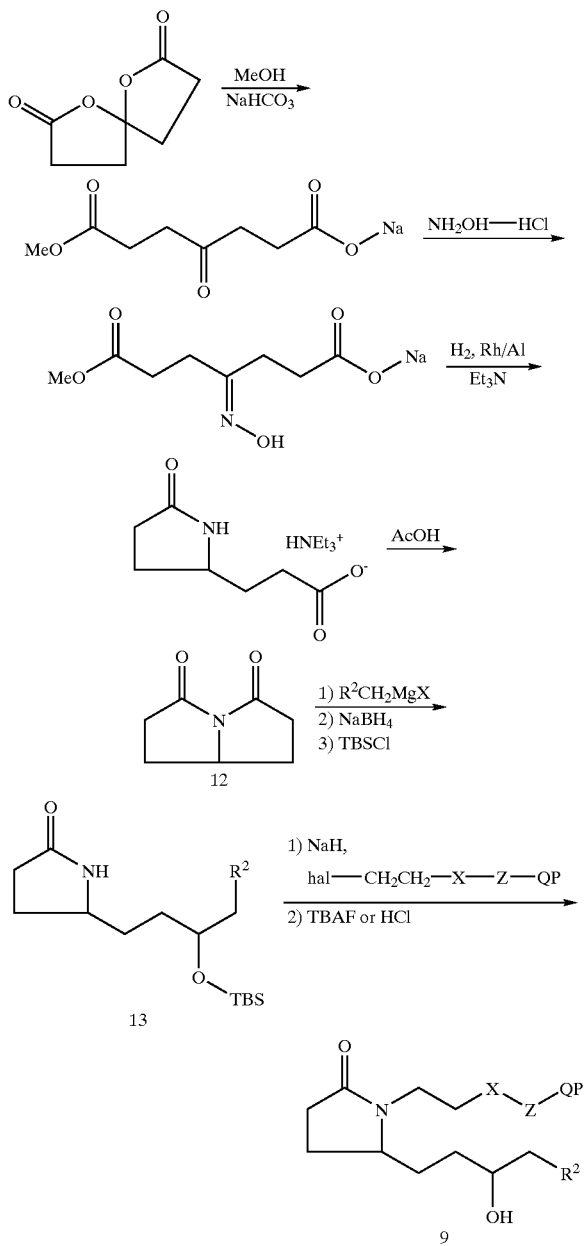

Compounds of formula 9 of Scheme F are converted to compounds of Formula I by methods well known to those skilled in the art. In cases where the QP group is a carboxylic ester, either acidic or basic aqueous hydrolysis conditions may be utilized. Typically, lower alkyl esters are hydrolyzed by base catalyzed hydrolysis in a reaction inert solvent at ambient temperature to about the reflux temperature of the solvent being used. Preferably the lower alkyl ester is hydrolyzed with aqueous 1 N sodium hydroxide in methanol at a suitable temperature, preferably at ambient temperature. When QP is a benzyl ester or a t-butyl ester, standard deprotection methods are utilized as described in Greene, T. W.; Wuts, P. G. M., Protective Groups in Organic Synthesis, $2^{nd}$ ed.; John Wiley and Sons Inc.: New York, 1991. When QP is a nitrile and not a protected carboxylic acid, a preferred method for preparation of the tetrazole is treatment of the nitrile with dibutyltin oxide and trimethylsilylazide in refluxing toluene (S. J. Wittenberger and B. G. Donner, J. Org. Chem. 1993, 58, 4139–4141, 1993). For a review of alternative preparations of tetrazoles see R. N. Butler, Tetrazoles, In comprehensive Heterocyclic Chemistry; Potts, K. T. Ed.; Pergamon Press: Oxford, 1984, Vol. 5, p 791–838.

The EP4 receptor selective agonists of Formula I of this invention are all adapted to therapeutic use as agents that stimulate bone formation and increase bone mass in vertebrates, e.g., mammals, and particularly humans. Since bone formation is closely related to the development of osteoporosis and bone related disorders, the agonists used in the methods of this invention, by virtue of their action on bone, prevent, arrest and/or regress osteoporosis.

The utility of the EP4 selective agonists of Formula I of the present invention as medical agents in the treatment of conditions which present with low bone mass (e.g., osteoporosis) in vertebrates, e.g., mammals (especially humans and particularly female humans) is demonstrated by the activity of those agonists in conventional assays, including a cyclic AMP assay, an in vivo assay and a fracture healing assay, all of which are described below. Such assays also provide a means whereby the activities of the EP4 selective agonists of Formula I of this invention can be compared to each other and with the activities of other known compounds and compositions. The results of these comparisons are useful for determining dosage levels in a vertebrates, e.g., mammals, including humans, for the treatment of such diseases.

In Vivo Assay

The activity of anabolic bone agents in stimulating bone formation and increasing bone mass can be tested in intact male or female rats, sex hormone deficient male (orchidectomy) or female (ovariectomy) rats.

Male or female rats at different ages (such as 3 months of age) can be used in the study. The rats are either intact or castrated (ovariectomized or orchidectomized), and subcutaneously injected or gavaged with a compound of Formula I of this invention at different doses (such as 1, 3, or 10 mg/kg/day) for 30 days. In the castrated rats, treatment is started on the next day after surgery (for the purpose of preventing bone loss) or at the time bone loss has already occured (for the purpose of restoring bone mass). During the study, all rats are allowed free access to water and a pelleted commercial diet (Teklad Rodent Diet #8064, Harlan Teklad, Madison, Wis.) containing 1.46% calcium, 0.99% phosphorus and 4.96 1U/g of Vitamin $D_3$. All rats are given subcutaneous injections of 10 mg/kg calcein on days 12 and 2 before sacrifice. The rats are sacrificed. The following endpoints are determined:

Femoral Bone Mineral Measurements

The right femur from each rat is removed at autopsy and scanned using dual energy X-ray absorptiometry (DXA, QDR 1000/W, Hologic Inc., Waltham, Mass.) equipped with "Regional High Resolution Scan" software (Hologic Inc., Waltham, Mass.). The scan field size is 5.08×1.902 cm, resolution is 0.0254×0.0127 cm and scan speed is 7.25 mm/second. The femoral scan images are analyzed and bone area, bone mineral content (BMC), and bone mineral density (BMD) of whole femora (WF), distal femoral metaphyses (DFM), femoral shaft (FS), and proximal femora (PF) are determined.

Tibial Bone Histomorphometric Analyses

The right tibia is removed at autopsy, dissected free of muscle, and cut into three parts. The proximal tibia and the tibial shaft are fixed in 70% ethanol, dehydrated in graded concentrations of ethanol, defatted in acetone, then embedded in methyl methacrylate (Eastman Organic Chemicals, Rochester, N.Y.).

Frontal sections of proximal tibial metaphyses at 4 and 10 μm thickness are cut using a Reichert-Jung Polycut S microtome. The 4 μm sections are stained with modified Masson's Trichrome stain while the 10 μm sections remain unstained. One 4 μm and one 10 μm section from each rat are used for cancellous bone histomorphometry.

Cross sections of tibial shaft at 10 μm thickness are cut using a Reichert-Jung Polycut S microtome. These sections are used for cortical bone histomorphometric analysis.

Cancellous bone histomorphometry: A Bioquant OS/2 histomorphometry system (R&M Biometrics, Inc., Nashville, Tenn.) is used for the static and dynamic histomorphometric measurements of the secondary spongiosa of the proximal tibial metaphyses between 1.2 and 3.6 mm distal to the growth plate-epiphyseal junction. The first 1.2 mm of the tibial metaphyseal region needs to be omitted in order to restrict measurements to the secondary spongiosa. The 4 μm sections are used to determine indices related to bone volume, bone structure, and bone resorption, while the 10 μm sections are used to determine indices related to bone formation and bone turnover.

I) Measurements and calculations related to trabecular bone volume and structure: (1) Total metaphyseal area (TV, $mm^2$): metaphyseal area between 1.2 and 3.6 mm distal to the growth plate-epiphyseal junction. (2) Trabecular bone area (BV, $mm^2$): total area of trabeculae within TV. (3) Trabecular bone perimeter (BS, mm): the length of total perimeter of trabeculae. (4) Trabecular bone volume (BV/TV, %): BV/TV×100. (5) Trabecular bone number (TBN, #/mm): 1.199/2×BS/TV. (6) Trabecular bone thickness (TBT, μm): (2000/1.199)×(BV/BS). (7) Trabecular bone separation (TBS, μm): (2000×1.199)×(TV−BV).

II) Measurements and calculations related to bone resorption: (1) Osteoclast number (OCN, #): total number of osteoclast within total metaphyseal area. (2) Osteoclast perimeter (OCP, mm): length of trabecular perimeter covered by osteoclast. (3) Osteoclast number/mm (OCN/mm, #/mm): OCN/BS. (4) Percent osteoclast perimeter (%OCP, %): OCP/BS×100.

III) Measurements and calculations related to bone formation and turnover: (1) Single-calcein labeled perimeter (SLS, mm): total length of trabecular perimeter labeled with one calcein label. (2) Double-calcein labeled perimeter (DLS, mm): total length of trabecular perimeter labeled with two calcein labels. (3) Inter-labeled width (ILW, μm): average distance between two calcein labels. (4) Percent mineralizing perimeter (PMS, %): (SLS/2+DLS)/BS×100. (5) Mineral apposition rate (MAR, μm/day): ILW/label interval. (6) Bone formation rate/surface ref. (BFR/BS, $μm^2/d/μm$): (SLS/2+DLS)×MAR/BS. (7) Bone turnover rate (BTR, %/y): (SLS/2+DLS)×MAR/BV×100.

Cortical bone histomorphometry: A Bioquant OS/2 histomorphometry system (R&M Biometrics, Inc., Nashville, Tenn.) is used for the static and dynamic histomorphometric measurements of tibial shaft cortical bone. Total tissue area, marrow cavity area, periosteal perimeter, endocortical perimeter, single labeled perimeter, double labeled perimeter, and interlabeled width on both periosteal and endocortical surface are measured, and cortical bone area (total tissue area−marrow cavity area), percent cortical bone area (cortical area/total tissue area×100), percent marrow area (marrow cavity area/total tissue area×100), periosteal and endocortical percent labeled perimeter [(single labeled perimeter/2+double labeled perimeter)/total perimeter× 100], mineral apposition rate (interlabeled width/intervals), and bone formation rate [mineral apposition rate×[(single labeled perimeter/2+double labeled perimeter)/total perimeter] are calculated.

Statistics

Statistics can be calculated using StatView 4.0 packages (Abacus Concepts, Inc., Berkeley, Calif.). The analysis of variance (ANOVA) test followed by Fisher's PLSD (Stat View, Abacus Concepts Inc., 1918 Bonita Ave, Berkeley, Calif. 94704–1014) are used to compare the differences between groups.

The full length coding sequence for the $EP_1$ receptor is made as disclosed in Funk et al., Journal of Biological Chemistry, 1993, 268, 26767–26772. The full length coding sequence for the $EP_2$ receptor is made as disclosed in Regan et al., Molecular Pharmacology, 1994, 46, 213–220. The full length coding sequence for the $EP_3$ receptor is made as disclosed in Regan et al., British Journal of Pharmacology, 1994, 112, 377–385. The full length coding sequence for the $EP_4$ receptor is made as disclosed in Bastien, Journal of Biological Chemistry, 1994, 269, 11873–11877. These full length receptors are used to prepare 293S cells expressing the $EP_1$, $EP_2$, $EP_3$ or $EP_4$ receptors.

293S cells expressing either the human $EP_1$, $EP_2$, $EP_3$ or $EP_4$ prostaglandin $E_2$ receptors are generated according to methods known to those skilled in the art. Typically, PCR (polymerase chain reaction) primers corresponding to the 5' and 3' ends of the published full length receptor are made according to the well known methods disclosed above and are used in an RT-PCR reaction using the total RNA from human kidney (for $EP_1$), human lung (for $EP_2$), human lung (for $EP_3$) or human lymphocytes (for $EP_4$) as a source. PCR products are cloned by the TA overhang method into pCR2.1 (Invitrogen, Carlsbad, Calif.) and identity of the cloned receptor is confirmed by DNA sequencing.

293S cells (Mayo, Dept. of Biochemistry, Northwestern Univ.) are transfected with the cloned receptor in pcDNA3 by electroporation. Stable cell lines expressing the receptor are established following selection of transfected cells with G418.

Clonal cell lines expressing the maximal number of receptors are chosen following a whole cell $^3H$-$PGE_2$ binding assay using unlabeled $PGE_2$ as a competitor.

Fracture Healing Assays Assay for Effects on Fracture Healing After Systemic Administration Fracture Technique: Sprage-Dawley rats at 3 months of age are anesthetized with Ketamine. A 1 cm incision is made on the anteromedial aspect of the proximal part of the right tibia or femur. The following describes the tibial surgical technique. The incision is carried through to the bone, and a 1 mm hole is drilled 4 mm proximal to the distal aspect of the tibial tuberosity 2 mm medial to the anterior ridge. Intramedullary nailing is performed with a 0.8 mm stainless steel tube (maximum load 36.3 N, maximum stiffness 61.8 N/mm, tested under the same conditions as the bones). No reaming of the medullary canal is performed. A standardized closed fracture is produced 2 mm above the tibiofibular junction by three-point bending using specially designed adjustable forceps with blunt jaws. To minimize soft tissue damage, care is taken not to displace the fracture. The skin is closed with monofilament nylon sutures. The operation is performed under sterile conditions. Radiographs of all fractures are taken immediately after nailing, and rats with fractures outside the specified diaphyseal area or with displaced nails are excluded. The remaining animals are divided randomly into the following groups with 10–12 animals per each subgroup per time point for testing the fracture healing. The first group receives daily gavage of vehicle (water:100% ethanol=95:5) at 1 ml/rat, while the others receive daily gavage from 0.01 to 100 mg/kg/day of the compound to be tested (1 ml/rat) for 10, 20, 40 and 80 days.

At 10, 20, 40 and 80 days, 10–12 rats from each group are anesthetized with Ketamine and sacrificed by exsanguination. Both tibiofibular bones are removed by dissection and all soft tissue is stripped. Bones from 5–6 rats for each group are stored in 70% ethanol for histological analysis, and bones from another 5–6 rats for each group are stored in a buffered Ringer's solution (+4° C., pH 7.4) for radiographs and biomechanical testing which is performed.

Histological Analysis: The methods for histologic analysis of fractured bone have been previously published by Mosekilde and Bak (The Effects of Growth Hormone on Fracture Healing in Rats: A Histological Description. Bone, 14:19–27, 1993). Briefly, the fracture site is sawed 8 mm to each side of the fracture line, embedded undecalcified in methymethacrylate, and cut frontals sections on a Reichert-Jung Polycut microtome in 8 µm thick. Masson-Trichrome stained mid-frontal sections (including both tibia and fibula) are used for visualization of the cellullar and tissue response to fracture healing with and without treatment. Sirius red stained sections are used to demonstrate the characterisitics of the callus structure and to differentiate between woven bone and lamellar bone at the fracture site. The following measurements are performed: (1) fracture gap—measured as the shortest distance between the cortical bone ends in the fracture, (2) callus length and callus diameter, (3) total bone volume area of callus, (4) bony tissue per tissue area inside the callus area, (5) fibrous tissue in the callus, and (6) cartilage area in the callus.

Biomechanical Analysis: The methods for biomechanical analysis have been previously published by Bak and Andreassen (The Effects of Aging on Fracture Healing in Rats. Calcif Tissue Int 45:292–297, 1989). Briefly, radiographs of all fractures are taken prior to the biomechanical test. The mechanical properties of the healing fractures are analyzed by a destructive three- or four-point bending procedure. Maximum load, stiffness, energy at maximum load, deflection at maximum load, and maximum stress are determined.

Assay for Effects on Fracture Healing After Local Administration

Fracture Technique: Female or male beagle dogs at approximately 2 years of age are used under anesthesia in the study. Transverse radial fractures are produced by slow continuous loading in three-point bending as described by Lenehan et al. (Lenehan, T. M.; Balligand, M.; Nunamaker, D. M.; Wood, F. E.: Effects of EHDP on Fracture Healing in Dogs. J Orthop Res 3:499–507; 1985). A wire is pulled through the fracture site to ensure complete anatomical disruption of the bone. Thereafter, local delivery of the compound to be tested to the fracture site is achieved by slow release of compound delivered by slow release pellets or by administration of the compound in a suitable formulation such as a paste gel solution or suspension for 10, 15, or 20 weeks.

Histological Analysis: The methods for histologic analysis of fractured bone have been previously published by Peter et al. (Peter, C. P.; Cook, W. O.; Nunamaker, D. M.; Provost, M. T.; Seedor, J. G.; Rodan, G. A. Effects of alendronate on fracture healing and bone remodeling in dogs. J. Orthop. Res. 14:74-70, 1996) and Mosekilde and Bak (The Effects of Growth Hormone on Fracture Healing in Rats: A Histological Description. Bone, 14:19–27, 1993). Briefly, after sacrifice, the fracture site is sawed 3 cm to each side of the fracture line, embedded undecalcified in methymethacrylate, and cut on a Reichert-Jung Polycut microtome in 8 µm thick of frontal sections. Masson-Trichrome stained mid-frontal sections (including both tibia and fibula) are used for visualization of the cellullar and tissue response to fracture healing with and without treatment. Sirius red stained sections are used to demonstrate the characterisitics of the callus structure and to differentiate between woven bone and lamellar bone at the fracture site. The following measurements are performed: (1) fracture gap—measured as the shortest distance between the cortical bone ends in the fracture, (2) callus length and callus diameter, (3) total bone volume area of callus, (4) bony tissue per tissue area inside the callus area, (5) fibrous tissue in the callus and (6) cartilage area in the callus.

Biomechanical Analysis: The methods for biomechanical analysis have been previously published by Bak and Andreassen (The Effects of Aging on Fracture Healing in Rats. Calcif Tissue Int 45:292–297, 1989) and Peter et al. (Peter, C. P.; Cook, W. O.; Nunamaker, D. M.; Provost, M. T.; Seedor, J. G.; Rodan, G. A. Effects of Alendronate On Fracture Healing And Bone Remodeling In Dogs. J. Orthop. Res. 14:74-70, 1996). Briefly, radiographs of all fractures are taken prior to the biomechanical test. The mechanical properties of the healing fractures are analyzed by a destructive three- or four-point bending procedures. Maximum load, stiffness, energy at maximum load, deflection at maximum load, and maximum stress are determined.

Kidney Regeneration Assay

The role of a prostaglandin agonist in kidney regeneration is investigated by the ability of Prostaglandin $E_2$ ($PGE_2$) or a prostaglandin agonist to induce the expression of Bone Morphogenetic Protein 7 (BMP-7) in wild type 293S cells and in 293S cells transfected with $EP_2$.

Methods: 293S and EP2 293S cells are grown in Dulbecco's Modified Egale medium (DMEM, Gibco, BRL; Gaithersburg, Md.). One day prior to treatment with $PGE_2$ or a prostaglandin agonist, cells are plated at a density of $1.5 \times 10^6$ cells /10 cm dish. Generally about 16 to 24 hours later the cell monolayer is washed once with OptiMEM (Gibco, BRL; Gaithersburg, Md.) followed by the addition of 10 ml OptiMEM/dish in the presence and absense of vehicle (DMSO), $PGE_2$ ($10^{-6}$M) or a prostaglandin agonist ($10^{-6}$M). Cells are harvested and RNA is extracted at 8, 16 and 24 hours. Northern blot analysis of total RNA (20 mg/lane) is carried out by probing the blots with $^{32}$P-labeled BMP-7 probe. The blots are normalized for RNA loading by hybridization with $^{32}$P-labeled 18s ribosomal RNA probe. $PGE_2$ and prostaglandin agonists induce the expression of BMP-7 in the $EP_2$ 293S cells in a time dependent manner. Such induction of expression is generally not observed in the parental cell line. Given the known role of BMP-7 in kidney regeneration and the ability of an prostaglandin agonist to induce BMP-7 expression in 2933 kidney cells in a time and receptor specific manner indicates a role for prostaglandin agonist in kidney regeneration.

Those skilled in the art will recognize that anti-resorptive agents (for example progestins, polyphosphonates, bisphosphonate(s), estrogen agonists/antagonists, estrogen, estrogen/progestin combinations, Premarin®, estrone, estriol or 17α- or 17β-ethynyl estradiol) may be used in conjunction with the compounds of this invention.

Exemplary progestins are available from commercial sources and include: algestone acetophenide, altrenogest, amadinone acetate, anagestone acetate, chlormadinone acetate, cingestol, clogestone acetate, clomegestone acetate, delmadinone acetate, desogestrel, dimethisterone, dydrogesterone, ethynerone, ethynodiol diacetate, etonogestrel, flurogestone acetate, gestaclone, gestodene, gestonorone caproate, gestrinone, haloprogesterone, hydroxyprogesterone caproate, levonorgestrel, lynestrenol, medrogestone, medroxyprogesterone acetate, melengestrol acetate, methynodiol diacetate, norethindrone, norethindrone acetate, norethynodrel, norgestimate, norgestomet, norgestrel, oxogestone phenpropionate, progesterone, quingestanol acetate, quingestrone, and tigestol.

Preferred progestins are medroxyprogestrone, norethindrone and norethynodrel.

Exemplary bone resorption inhibiting polyphosphonates include polyphosphonates of the type disclosed in U.S. Pat. No. 3,683,080, the disclosure of which is incorporated herein by reference. Preferred polyphosphonates are geminal diphosphonates (also referred to as bis-phosphonates). Tiludronate disodium is an especially preferred polyphosphonate. Ibandronic acid is an especially preferred polyphosphonate. Alendronate is an especially preferred polyphosphonate. Zoledronic acid is an especially preferred polyphosphonate. Other preferred polyphosphonates are 6-amino-1-hydroxy-hexylidene-bisphosphonic acid and 1-hydroxy-3(methylpentylamino)-propylidene-bisphosphonic acid. The polyphosphonates may be administered in the form of the acid, or of a soluble alkali metal salt or alkaline earth metal salt. Hydrolyzable esters of the polyphosphonates are likewise included. Specific examples include ethane-1-hydroxy 1,1-diphosphonic acid, methane diphosphonic acid, pentane-1-hydroxy-1,1-diphosphonic acid, methane dichloro diphosphonic acid, methane hydroxy diphosphonic acid, ethane-1-amino-1,1-diphosphonic acid, ethane-2-amino-1,1-diphosphonic acid, propane-3-amino-1-hydroxy-1,1-diphosphonic acid, propane-N,N-dimethyl-3-amino-1-hydroxy-1,1-diphosphonic acid, propane-3,3-dimethyl-3-amino-1-hydroxy-1,1-diphosphonic acid, phenyl amino methane diphosphonic acid,N,N-dimethylamino methane diphosphonic acid, N(2-hydroxyethyl) amino methane diphosphonic acid, butane-4-amino-1-hydroxy-1,1-diphosphonic acid, pentane-5-amino-1-hydroxy-1,1-diphosphonic acid, hexane-6-amino-1-hydroxy-1,1-diphosphonic acid and pharmaceutically acceptable esters and salts thereof.

In particular, the compounds of this invention may be combined with a mammalian estrogen agonist/antagonist. Any estrogen agonist/antagonist may be used as the second compound of this invention. The term estrogen agonist/antagonist refers to compounds which bind with the estrogen receptor, inhibit bone turnover and/or prevent bone loss. In particular, estrogen agonists are herein defined as chemical compounds capable of binding to the estrogen receptor sites in mammalian tissue, and mimicking the actions of estrogen in one or more tissue. Estrogen antagonists are herein defined as chemical compounds capable of binding to the estrogen receptor sites in mammalian tissue, and blocking the actions of estrogen in one or more tissues. Such activities are readily determined by those skilled in the art of standard assays including estrogen receptor binding assays, standard bone histomorphometric and densitometer methods, and Eriksen E. F. et al., Bone Histomorphometry, Raven Press, New York, 1994, pages 1–74; Grier S. J. et. al., The Use of Dual-Energy X-Ray Absorptiometry In Animals, Inv. Radiol., 1996, 31(1):50–62; Wahner H. W. and Fogelman I., The Evaluation of Osteoporosis: Dual Energy X-Ray Absorptiometry in Clinical Practice., Martin Dunitz Ltd., London 1994, pages 1–296). A variety of these compounds are described and referenced below.

A preferred estrogen agonist/antagonist is droloxifene: (phenol, 3-(1-(4-(2-(dimethylamino)ethoxy)phenyl)-2-phenyl-1-butenyl)-, (E)-) and related compounds which are disclosed in U.S. Pat. No. 5,047,431, the disclosure of which is incorporated herein by reference.

Another preferred estrogen agonist/antagonist is 3-(4-(1, 2-diphenyl-but-1-enyl)-phenyl)-acrylic acid, which is disclosed in Willson et al., Endocrinology, 1997, 138, 3901–3911.

Another preferred estrogen agonist/antagonist is tamoxifen: (ethanamine,2-(-4-(1,2-diphenyl-1-butenyl)phenoxy)-N,N-dimethyl, (Z)-2-, 2-hydroxy-1,2,3-propanetricarboxylate(1:1)) and related compounds which are disclosed in U.S. Pat. No. 4,536,516, the disclosure of which is incorporated herein by reference.

Another related compound is 4-hydroxy tamoxifen which is disclosed in U.S. Pat. No. 4,623,660, the disclosure of which is incorporated herein by reference.

A preferred estrogen agonist/antagonist is raloxifene: (methanone, (6-hydroxy-2-(4-hydroxyphenyl)benzo[b]thien-3-yl)(4-(2-(1-piperidinyl)ethoxy)phenyl)-hydrochloride) which is disclosed in U.S. Pat. No. 4,418,068, the disclosure of which is incorporated herein by reference.

Another preferred estrogen agonist/antagonist is toremifene: (ethanamine, 2-(4-(4-chloro-1,2-diphenyl-1-butenyl)phenoxy)-N,N-dimethyl-, (Z)-, 2-hydroxy-1,2,3-propanetricarboxylate (1:1) which is disclosed in U.S. Pat. No. 4,996,225, the disclosure of which is incorporated herein by reference.

Another preferred estrogen agonist/antagonist is centchroman: 1-(2-((4-(-methoxy-2,2, dimethyl-3-phenyl-chroman-4-yl)-phenoxy)-ethyl)-pyrrolidine, which is disclosed in U.S. Pat. No. 3,822,287, the disclosure of which is incorporated herein by reference. Also preferred is levormeloxifene.

Another preferred estrogen agonist/antagonist is idoxifene: (E)-1-(2-(4-(1-(4-iodo-phenyl)-2-phenyl-but-1-enyl)-phenoxy)-ethyl)-pyrrolidinone, which is disclosed in U.S. Pat. No. 4,839,155, the disclosure of which is incorporated herein by reference.

Another preferred estrogen agonist/antagonist is 2-(4-methoxy-phenyl)-3-[4-(2-piperidin-1-yl-ethoxy)-phenoxy]-benzo[b]thiophen-6-ol which is disclosed in U.S. Pat. No. 5,488,058, the disclosure of which is incorporated herein by reference.

Another preferred estrogen agonist/antagonist is 6-(4-hydroxy-phenyl)-5-(4-(2-piperidin-1-yl-ethoxy)-benzyl)-naphthalen-2-ol which is disclosed in U.S. Pat. No. 5,484,795, the disclosure of which is incorporated herein by reference.

Another preferred estrogen agonist/antagonist is (4-(2-(2-aza-bicyclo[2.2.1]hept-2-yl)-ethoxy)-phenyl)-(6-hydroxy-2-(4-hydroxy-phenyl)-benzo[b]thiophen-3-yl)-methanone which is disclosed, along with methods of preparation, in PCT publication no. WO 95/10513 assigned to Pfizer Inc.

Other preferred estrogen agonist/antagonists include compounds as described in commonly assigned U.S. Pat. No. 5,552,412, the disclosure of which is incorporated herein by reference.

Especially preferred compounds described therein are:
cis-6-(4-fluoro-phenyl)-5-(4-(2-piperidin-1-yl-ethoxy)-phenyl)-5,6,7,8-tetrahydro-naphthalene-2-ol;
(−)-cis-6-phenyl-5-(4-(2-pyrrolidin-1-yl-ethoxy)-phenyl)-5,6,7,8-tetrahydro-naphthalene-2-ol (lasofoxifene);
cis-6-phenyl-5-(4-(2-pyrrolidin-1-yl-ethoxy)-phenyl)-5,6,7,8-tetrahydro-naphthalene-2-ol (lasofoxifene);
cis-1-(6'-pyrrolodinoethoxy-3'-pyridyl)-2-phenyl-6-hydroxy-1,2,3,4-tetrahydronaphthalene;
1-(4'-pyrrolidinoethoxyphenyl)-2-(4"-fluorophenyl)-6-hydroxy-1,2,3,4-tetrahydroisoquinoline;
cis-6-(4-hydroxyphenyl)-5-(4-(2-piperidin-1-yl-ethoxy)-phenyl)-5,6,7,8-tetrahydro-naphthalene-2-ol; and
1-(4'-pyrrolidinolethoxyphenyl)-2-phenyl-6-hydroxy-1,2,3,4-tetrahydroisoquinoline.

Other estrogen agonist/antagonists are described in U.S. Pat. No. 4,133,814 (the disclosure of which is incorporated herein by reference). U.S. Pat. No. 4,133,814 discloses derivatives of 2-phenyl-3-aroyl-benzothiophene and 2-phenyl-3-aroylbenzothiophene-1-oxide.

Those skilled in the art will recognize that other bone anabolic agents, also referred to as bone mass augmenting agents, may be used in conjunction with the compounds of this invention. A bone mass augmenting agent is a compound that augments bone mass to a level which is above the bone fracture threshold as detailed in the World Health Organization Study World Health Organization, "Assessment of Fracture Risk and its Application to Screening for Postmenopausal Osteoporosis (1994). Report of a WHO Study Group. World Health Organization Technical Series 843."

Any prostaglandin, or prostaglandin agonist/antagonist may be used as the second compound in certain aspects of this invention. This includes utilizing two different compounds of Formula I of this inventon. Those skilled in the art will recognize that IGF-1, sodium fluoride, parathyroid hormone (PTH), active fragments of parathyroid hormone, growth hormone or growth hormone secretagogues may also be used. The following paragraphs describe exemplary second compounds of this invention in greater detail.

Any prostaglandin may be used as the second compound in certain aspects of this invention. The term prostaglandin refers to compounds which are analogs of the natural prostaglandins $PGD_1$, $PGD_2$, $PGE_2$, $PGE_1$ and $PGF_2$ which are useful in the treatment of osteoporosis. These compounds bind to the prostaglandin receptors. Such binding is readily determined by those skilled in the art of standard assays (e.g., An S. et al., Cloning and Expression of the $EP_2$ Subtype of Human Receptors for Prostaglandin $E_2$, Biochemical and Biophysical Research Communications, 1993, 197(1):263–270).

Prostaglandins are alicyclic compounds related to the basic compound prostanoic acid. The carbon atoms of the basic prostaglandin are numbered sequentially from the carboxylic carbon atom through the cyclopentyl ring to the terminal carbon atom on the adjacent side chain. Normally the adjacent side chains are in the trans orientation. The presence of an oxo group at C-9 of the cyclopentyl moiety is indicative of a prostaglandin within the E class while $PGE_2$ contains a trans unsaturated double bond at the $C_{13}$–$C_{14}$ and a cis double bond at the $C_5$–$C_6$ position.

A variety of prostaglandins are described and referenced below. However, other prostaglandins will be known to those skilled in the art. Exemplary prostaglandins are disclosed in U.S. Pat. Nos. 4,171,331 and 3,927,197, the disclosures of each of which are incorporated herein by reference.

Norrdin et al., *The Role of Prostaglandins in Bone In Vivo*, Prostaglandins Leukotriene Essential Fatty Acids 41, 139–150, 1990 is a review of bone anabolic prostaglandins.

Any prostaglandin agonist/antagonist may be used as the second compound in certain aspects of this invention. The term prostaglandin agonist/antagonist refers to compounds which bind to prostaglandin receptors (e.g., An S. et al., Cloning and Expression of the $EP_2$ Subtype of Human Receptors for Prostaglandin $E_2$, Biochemical and Biophysical Research Communications, 1993, 197(1):263–270) and mimic the action of prostaglandin in vivo (e.g., stimulate bone formation and increase bone mass). Such actions are readily determined by those skilled in the art of standard assays. Eriksen E. F. et al., *Bone Histomorphometry*, Raven Press, New York, 1994, pages 1–74; Grier S. J. et. al., The Use of Dual-Energy X-Ray Absorptiometry In Animals, Inv. Radiol., 1996, 31(1):50–62; Wahner H. W. and Fogelman I., The Evaluation of Osteoporosis: Dual Energy X-Ray Absorptiometry in Clinical Practice., Martin Dunitz Ltd., London 1994, pages 1–296. A variety of these compounds are described and referenced below. However, other prostaglandin agonists/antagonists will be known to those skilled in the art. Exemplary prostaglandin agonists/antagonists are disclosed as follows.

Commonly assigned U.S. Pat. No. 3,932,389, the disclosure of which is incorporated herein by reference, discloses 2-descarboxy-2-(tetrazol-5-yl)-11-desoxy-15-substituted-omega-pentanorprostaglandins useful for bone formation activity.

Commonly assigned U.S. Pat. No. 4,018,892, the disclosure of which is esters useful for bone formation activity."

Commonly assigned U.S. Pat. No. 4,219,483, the disclosure of which is incorporated herein by reference, discloses 2,3,6-substituted-4-pyrones useful for bone formation activity.

Commonly assigned U.S. Pat. No. 4,132,847, the disclosure of which is incorporated herein by reference, discloses 2,3,6-substituted-4-pyrones useful for bone formation activity.

U.S. Pat. No. 4,000,309, the disclosure of which is incorporated herein by reference, discloses 16-aryl-13,14-dihydro-$PGE_2$ p-biphenyl esters useful for bone formation activity.

U.S. Pat. No. 3,982,016, the disclosure of which is incorporated herein by reference, discloses 16-aryl-13,14-dihydro-$PGE_2$ p-biphenyl esters useful for bone formation activity.

U.S. Pat. No. 4,621,100, the disclosure of which is incorporated herein by reference, discloses substituted cyclopentanes useful for bone formation activity.

U.S. Pat. No. 5,216,183, the disclosure of which is incorporated herein by reference, discloses cyclopentanones useful for bone formation activity.

Sodium fluoride may be used as the second compound in certain aspects of this invention. The term sodium fluoride refers to sodium fluoride in all its forms (e.g., slow release sodium fluoride, sustained release sodium fluoride). Sustained release sodium fluoride is disclosed in U.S. Pat. No.

4,904,478, the disclosure of which is incorporated herein by reference. The activity of sodium fluoride is ready determined by those skilled in the art of biological protocols (e.g., see Eriksen E. F. et al., Bone Histomorphometry, Raven Press, New York, 1994, pages 1–74; Grier S. J. et. al., The Use of Dual-Energy X-Ray Absorptiometry In Animals, Inv. Radiol., 1996, 31(1):50–62; Wahner H. W. and Fogelman I., The Evaluation of Osteoporosis: Dual Energy X-Ray Absorptiometry in Clinical Practice., Martin Dunitz Ltd., London 1994, pages 1–296).

Bone morphogenetic protein may be used as the second compound of this invention (e.g., see Ono, et al., Promotion of the Osteogenetic Activity of Recombinant Human Bone Morphogenetic Protein by Prostaglandin E1, Bone, 1996, 19(6), 581–588).

Any parathyroid hormone (PTH) may be used as the second compound in certain aspects of this invention. The term parathyroid hormone refers to parathyroid hormone, fragments or metabolites thereof and structural analogs thereof which can stimulate bone formation and increase bone mass. Also included are parathyroid hormone related peptides and active fragments and analogs of parathyroid related peptides (see PCT publication no. WO 94/01460). Such bone anabolic functional activity is readily determined by those skilled in the art of standard assays (e.g., see Eriksen E. F. et al., Bone Histomorphometry, Raven Press, New York, 1994, pages 1–74; Grier S. J. et. al., The Use of Dual-Energy X-Ray Absorptiometry In Animals, Inv. Radiol., 1996, 31(1):50–62; Wahner H. W. and Fogelman I., The Evaluation of Osteoporosis: Dual Energy X-Ray Absorptiometry in Clinical Practice., Martin Dunitz Ltd., London 1994, pages 1–296). A variety of these compounds are described and referenced below. However, other parathyroid hormones will be known to those skilled in the art. Exemplary parathyroid hormones are disclosed in the following references.

"Human Parathyroid Peptide Treatment of Vertebral Osteoporosis", Osteoporosis Int., 3, (Supp 1):199–203.

"PTH 1–34 Treatment of Osteoporosis with Added Hormone Replacement Therapy: Biochemical, Kinetic and Histological Responses" Osteoporosis Int. 1:162–170.

Any growth hormone or growth hormone secretagogue may be used as the second compound in certain aspects of this invention. The term growth hormone secretagogue refers to a compound which stimulates the release of growth hormone or mimics the action of growth hormone (e.g., increases bone formation leading to increased bone mass). Such actions are readily determined by those skilled in the art of standard assays well known to those of skill in the art. A variety of these compounds are disclosed in the following published PCT patent applications: WO 95/14666; WO 95/13069; WO 94/19367; WO 94/13696; and WO 95/34311. However, other growth hormones or growth hormone secretagogues will be known to those skilled in the art.

In particular a preferred growth hormone secretagogue is N-[1(R)-[1,2-Dihydro-1-methanesulfonylspiro[3H-indole-3,4'-piperidin]-1'-yl)carbonyl]-2-(phenylmethyloxy)ethyl]-2-amino-2-methylpropanamide:MK-677.

Other preferred growth hormone secretagogues include:
2-amino-N-(2-(3a-(R)-benzyl-2-methyl-3-oxo-2,3,3a,4,6,7-hexahydro-pyrazolo-[4,3-c]pyridin-5-yl)-1-(R)-benzyloxymethyl-2-oxo-ethyl)-isobutyramide or its L-tartaric acid salt:
2-amino-N-(1-(R)-benzyloxymethyl-2-(3a-(R)-(4-fluoro-benzyl)-2-methyl-3-oxo-2,3,3a,4,6,7-hexahydro-pyrazolo[4,3-c]pyridin-5-yl)-2-oxo-ethyl)isobutyramide;
2-amino-N-(2-(3a-(R)-benzyl-3-oxo-2,3,3a,4,6,7-hexahydro-pyrazolo[4,3-c]pyridin-5-yl)-1-(R) benzyloxymethyl-2-oxo-ethyl)isobutyramide; and 2-amino-N-(1-(2,4-difluoro-benzyloxymethyl)-2-oxo-2-(3-oxo-3a-pyridin-2-ylmethyl-2-(2,2,2-trifluoro-ethyl)-2,3,3a,4,6,7-hexahydro-pyrazolo[4,3-c]pyridin-5-yl)-ethyl)-2-methyl-propionamide.

The term "HMG-CoA reductase inhibitor" is intended to include compounds which inhibit the enzyme 3-hydroxy-3-methylglutaryl coenzyme A (HMG-CoA) reductase. Any HMG-COA reductase inhibitor may be used as the second compound of this invention, including mevastatin, lovastatin, pravastatin, velostatin, simvastaine, fluvastatin, cerivastatin, mevastatin, dalvastatin, fluindostatin and atorvastatin, or a prodrug thereof or a pharmaceutically acceptable salt of said compound or said prodrug.

Statins enhance the production of osteoblasts, the cells that produce new bone. The expression of the bone growth factor Bone Morphogenetic Protein (BMP) is known to enhance osteoblast differentiation. S. E. Harris, et al., Mol. Cell. Differ. 3, 137 (1995). Statins are in turn found to enhance BMP production. G. Mundy, et al., Stimulation of Bone Formation in Vitro and in Rodents by Statins, Science, 286, 1946 (1999). Mundy, et al. find that statins increase new bone formation as well as increase osteoblast cell numbers at all stages of differentiation.

It is preferred that said statin is mevastatin, lovastatin, pravastatin, velostatin, simvastatin, fluvastatin, cerivastatin, mevastatin, dalvastatin, fluindostatin or atorvastatin, or a prodrug thereof, or a pharmaceutically acceptable salt of said compound or prodrug.

It is especially preferred that said statin is atorvastatin, most preferably atorvastatin calcium.

HMG-CoA reductase inhibitors may be readily prepared by processes known in the chemical arts. Mevastatin, lovastatin, pravastatin, velostatin, simvastatin, fluvastatin, cerivastatin and mevastatin, dalvastatin and fluindostatin may be made in accordance with the process set forth in U.S. Pat. Nos. 3,983,140, 4,231,938, 4,346,227, 4,448,784, 4,450,171, 4,739,073, 5,177,080, 5,177,080, European Patent Application No. 738,510 A2 and European Patent Application No. 363,934 A1 respectively, which are all incorporated herein by reference.

Atorvastatin may readily be prepared as described in U.S. Pat. No. 4,681,893, which is incorporated herein by reference. The hemicalcium salt of atorvastatin, which is currently sold as Lipitor®, may readily be prepared as described in U.S. Pat. No. 5,273,995, which is incorporated herein by reference. Other pharmaceutically-acceptable cationic salts of atorvastatin may be readily prepared by reacting the free acid form of atorvastatin with an appropriate base, usually one equivalent, in a co-solvent.

Administration of the EP4 receptor selective agonists according to the methods of this invention can be via any mode which delivers the EP4 receptor selective agonist systemically and/or locally (e.g., at the site of the bone fracture, osteotomy, or orthopedic surgery). These methods include oral routes, parenteral, intraduodenal routes, etc. Generally, the compounds of this invention are administered orally, but parenteral administration (e.g., intravenous, intramuscular, transdermal, subcutaneous, rectal or intramedullary) may be utilized, for example, where oral administration is inappropriate for the target or where the patient is unable to ingest the drug.

The methods of this invention are used for the treatment and promotion of healing of bone fractures and osteotomies by the local application (e.g., to the sites of bone fractures of osteotomies) of EP4 receptor selective agonists. The EP4 receptor selective agonists of this invention are applied to the sites of bone fractures or osteotomies, for example, either by injection of the compound in a suitable solvent (e.g., an oily solvent such as arachis oil) to the cartilage growth plate or, in cases of open surgery, by local application thereto of the compound in a suitable vehicle, carrier or diluent such as bone-wax, demineralized bone powder, polymeric bone cements, bone sealants, etc. Alternatively, local application can be achieved by applying a solution or dispersion of the compound in a suitable carrier or diluent onto the surface of, or incorporating it into solid or semi-solid implants conventionally used in orthopedic surgery, such as dacron-mesh, gel-foam and kiel bone, or prostheses.

In any event, the amount and timing of compounds administered will, of course, be dependent on the subject being treated, on the severity of the affliction, on the manner of administration and on the judgment of the prescribing physician. Thus, because of patient to patient variability, the dosages given herein are a guideline and the physician may titrate doses of the compound to achieve the treatment (e.g., bone mass augmentation) that the physician considers appropriate for the patient. In considering the degree of treatment desired, the physician must balance a variety of factors such as bone mass starting level, age of the patient, presence of preexisting disease, as well as presence of other diseases (e.g., cardiovascular disease).

In general, an amount of a compound of Formula I of this invention is used that is sufficient to augment bone mass to a level which is above the bone fracture threshold (as detailed in the World Health Organization Study previously cited herein).

The compounds used in the methods of this invention are generally administered in the form of a pharmaceutical composition comprising at least one of the compounds of this invention together with a pharmaceutically acceptable carrier, vehicle or diluent. Thus, the EP4 receptor selective agonist can be administered individually in any conventional local, oral, intranasal, parenteral, rectal or transdermal dosage form.

For oral administration the pharmaceutical composition can take the form of solutions, suspensions, tablets, pills, capsules, powders, and the like. Tablets containing various excipients such as sodium citrate, calcium carbonate and calcium phosphate are employed along with various disintegrants such as starch and preferably potato or tapioca starch and certain complex silicates, together with binding agents such as polyvinylpyrrolidone, sucrose, gelatin and acacia. Additionally, lubricating agents such as magnesium stearate, sodium lauryl sulfate and talc are often very useful for tabletting purposes. Solid compositions of a similar type are also employed as fillers in soft and hard-filled gelatin capsules; preferred materials in this connection also include lactose or milk sugar as well as high molecular weight polyethylene glycols. When aqueous suspensions and/or elixirs are desired for oral administration, the compositions of this invention can be combined with various sweetening agents, flavoring agents, coloring agents, emulsifying agents and/or suspending agents, as well as such diluents as water, ethanol, propylene glycol, glycerin or various like combinations thereof.

For purposes of parenteral administration, solutions in sesame or peanut oil or in aqueous propylene glycol can be employed, as well as sterile aqueous solutions of the corresponding water-soluble salts. Such aqueous solutions may be suitably buffered, if necessary, and the liquid diluent first rendered isotonic with sufficient saline or glucose. These aqueous solutions are especially suitable for intravenous, intramuscular, subcutaneous and intraperitoneal injection purposes. In this connection, the sterile aqueous media employed are all readily obtainable by standard techniques well-known to those skilled in the art.

For purposes of transdermal (e.g.,topical) administration, dilute sterile, aqueous or partially aqueous solutions (usually in about 0.1% to 5% concentration), otherwise similar to the above parenteral solutions, are prepared.

Methods of preparing various pharmaceutical compositions with a certain amount of active ingredient are known, or will be apparent in light of this disclosure, to those skilled in the art. For examples of methods of preparing pharmaceutical compositions, see *Remington: The Science and Practice of Pharmacy,* Mack Publishing Company, Easton, Pa., 19th Edition (1995).

General Experimental Procedures

NMR spectra were recorded on a Varian Unity 400 spectrometer (Varian Co., Palo Alto, Calif.) at about 23° C. at 400 MHz for proton nuclei. Chemical shifts are expressed in parts per million. The peak shapes are denoted as follows: s, singlet; d, doublet; t, triplet; q, quartet; m, multiplet; bs, broad singlet. Atmospheric pressure chemical ionization (APCI) mass spectra were obtained on a Fisons Platform II Spectrometer (Micromass Inc., Beverly, Mass.). Where the intensity of chlorine or bromine-containing ions are described the expected intensity ratio was observed (approximately 3:1 for $^{35}Cl/^{37}Cl$-containing ions) and 1:1 for $^{79}Br/^{81}Br$-containing ions) and the intensity of only the lower mass ion is given.

Medium pressure chromatography was performed using a Biotage purification system (Biotage, Dyax Corporation, Charlottesville, Va.) under nitrogen pressure. Flash chromatography was performed with either Baker Silica Gel (40 $\mu$m) (J. T. Baker, Phillipsburg, N.J.) or Silica Gel 60 (EM Sciences, Gibbstown, N.J.) in glass columns under low nitrogen pressure. Radial Chromatography was performed using a Chromatotron (model 7924T, Harrison Research, Palo Alto, Calif.). Preparative Chromatography was performed using Analtech Uniplates Silica Gel GF (20×20 cm) (Analtech, Inc. Newark, Del.). Dimethylformamide (DMF), tetrahydrofuran (THF), and dichloromethane ($CH_2Cl_2$) used as reaction solvents were the anhydrous grade supplied by Aldrich Chemical Company (Milwaukee, Wis.). The term "concentrated" refers to removal of solvent at water aspirator pressure on a rotary evaporator. The term "EtOAc" means ethyl acetate. The abbreviation 'h' stands for hours. The term "TBAF" refers to tetrabutylammonium fluoride. The term "DMAP" refers to dimethylaminopyridine. The terms "dichloromethane" and "methylene chloride" are synonymous and are used interchangeably throughout this description and in the Examples and Preparations.

General Experimental Procedures

NMR spectra were recorded on a Varian Unity 400 spectrometer (Varian Co., Palo Alto, Calif.) at about 23° C. at 400 MHz for proton nuclei. Chemical shifts are expressed in parts per million. The peak shapes are denoted as follows: s, singlet; d, doublet; t, triplet; q, quartet; m, multiplet; bs, broad singlet. Atmospheric pressure chemical ionization (APCI) mass spectra were obtained on a Fisons Platform II Spectrometer (Micromass Inc., Beverly, Mass.). Where the intensity of chlorine or bromine-containing ions are described the expected intensity ratio was observed (approximately 3:1 for $^{35}Cl/^{37}Cl$-containing ions) and 1:1 for $^{79}Br/^{81}Br$-containing ions) and the intensity of only the lower mass ion is given.

Medium pressure chromatography was performed using a Biotage purification system (Biotage, Dyax Corporation, Charlottesville, Va.) under nitrogen pressure. Flash chromatography was performed with either Baker Silica Gel (40 μm) (J. T. Baker, Phillipsburg, N.J.) or Silica Gel 60 (EM Sciences, Gibbstown, N.J.) in glass columns under low nitrogen pressure. Radial Chromatography was performed using a Chromatotron (model 7924T, Harrison Research, Palo Alto, Calif.). Preparative Chromatography was performed using Analtech Uniplates Silica Gel GF (20×20 cm) (Analtech, Inc. Newark, Del.). Dimethylformamide (DMF), tetrahydrofuran (THF), and dichloromethane ($CH_2Cl_2$) used as reaction solvents were the anhydrous grade supplied by Aldrich Chemical Company (Milwaukee, Wis.). The term "concentrated" refers to removal of solvent at water aspirator pressure on a rotary evaporator. The term "EtOAc" means ethyl acetate. The abbreviation 'h' stands for hours. The term "TBAF" refers to tetrabutylammonium fluoride. The term "DMAP" refers to dimethylaminopyridine. The terms "dichloromethane" and "methylene chloride" are synonymous and are used interchangeably throughout this description and in the Examples and Preparations.

EXAMPLE 1A

4-{3-[2-(3-Hydroxy-4-phenyl-butyl)-5-oxo-pyrrolidin-1-yl]-propyl}-benzoic acid

Step A: 5-(3-Oxo-4-phenyl-butyl)-pyrrolidin-2-one. To a solution of tetrahydro-pyrrolizine-3,5-dione (5 g, 36 mmol) in $CH_2Cl_2$ (320 mL) at 0° C. was added benzyl magnesium chloride (1 M solution in THF, 39 mL, 39 mmol) dropwise. The solution was stirred at 0° C. for 3 h and was quenched with saturated aqueous ammonium chloride. After warming to room temperature, the aqueous solution was extracted with $CH_2Cl_2$ (3×). The combined organic extracts were dried ($MgSO_4$), filtered and concentrated. The residue was purified by medium pressure chromatography eluting with a solvent gradient (1% MeOH in $CH_2Cl_2$ to 2% MeOH in $CH_2Cl_2$) to yield 5.9021 g of 5-(3-oxo-4-phenyl-butyl)-pyrrolidin-2-one. $^1$H NMR ($CDCl_3$) δ7.35-7.18 (m, 5H), 3.69 (s, 2H), 3.56 (m, 1H), 2.50 (t, 2H), 2.27 (m, 2H), 2.15 (m, 1H), 1.73 (m, 2H), 1.61 (m, 1H).

Step B: 5-(3-Hydroxy-4-phenyl-butyl)-pyrrolidin-2-one. To a solution of 5-(3-oxo-4-phenyl-butyl)-pyrrolidin-2-one (5.902 g, 25.52 mmol) in EtOH (30 mL) at 0° C. was added $NaBH_4$ (485 mg, 12.76 mmol) and the reaction mixture was stirred at 0° C. for 2.5 h. The reaction mixture was quenched with saturated aqueous ammonium chloride. Water and $CH_2Cl_2$ were added. The aqueous layer was washed with $CH_2Cl_2$ (2×) and the combined organic extracts were dried ($MgSO_4$), filtered and concentrated. The residue was purified by medium pressure chromatography with a solvent gradient (1:1 hexanes:EtOAc to EtOAc to 1% MeOH in $CH_2Cl_2$) to yield 4.3 g of 5-(3-hydroxy-4-phenyl-butyl)-pyrrolidin-2-one. $^1$H NMR ($CDCl_3$) δ7.35-7.16 (m, 5H), 6.02 (m, 1H), 3.80 (m, 1H), 3.63 (m, 1H), 2.79 (m, 1H), 2.64 (m, 1H), 2.26 (m, 3H), 1.72-1.22 (m, 6H).

Step C: 5-[3-(tert-Butyl-dimethyl-silanyloxy)-4-phenyl-butyl]-pyrrolidin-2-one. To a solution of 5-(3-hydroxy-4-phenyl-butyl)-pyrrolidin-2-one (4.3 g, 18.43 mmol) in DMF (86 mL) was added tert-butyldimethylsilyl chloride (3.06 g, 20.3 mmol) followed by imidazole (2.5 g, 37 mmol) and DMAP (225 mg). The reaction mixture was stirred for 24 h and was quenched with saturated aqueous ammonium chloride. The aqueous solution was washed with EtOAc (3×) and the combined organic extracts were dried ($MgSO_4$), filtered and concentrated. The residue was purified by medium pressure chromatography eluting with a solvent gradient ($CH_2Cl_2$ to 1% MeOH in $CH_2Cl_2$ to 2% MeOH in $CH_2Cl_2$) to yield 5.94 g of 5-[3-(tert-butyl-dimethyl-silanyloxy)-4-phenyl-butyl]-pyrrolidin-2-one. $^1$H NMR ($CDCl_3$) δ7.26-7.10 (m, 5H), 5.68 (m, 1H), 3.83 (m, 1H), 3.54 (m, 1H), 2.69 (m, 2H), 2.30-2.16 (m, 3H), 1.66-1.35 (m, 5H), 0.82 (s, 9H), −0.06 (d, 3H), −0.2 (d, 3H).

Step D: 4-(3-{2-[3-(tert-Butyl-dimethyl-silanyloxy)-4-phenyl-butyl]-5-oxo-pyrrolidin-1-yl}-propyl)-benzoic acid methyl ester. To a solution of 5-[3-(tert-butyl-dimethyl-silanyloxy)-4-phenyl-butyl]-pyrrolidin-2-one (3.20 g, 9.21 mmol) in DMF (30 mL) at 0° C. was added NaHMDS (1M in THF, 11.5 mL, 11.5 mmol). After 1 h, 4-(3-bromo-propyl)-benzoic acid methyl ester (2.84 g, 11.0 mmol) was added and the reaction mixture was stirred at 70° C. for 18 h. The DMF was removed in vacuo and the residue was dissolved in EtOAc. The organic solution was washed with water, dried ($MgSO_4$), filtered and concentrated. The residue was purified by medium pressure chromatography (30% EtOAc in hexanes) to yield 3.39 g of 4-(3-{2-[3-(tert-butyl-dimethyl-silanyloxy)-4-phenyl-butyl]-5-oxo-pyrrolidin-1-yl}-propyl)-benzoic acid methyl ester. $^1$H NMR ($CDCl_3$) (selected peaks) δ7.92 (m, 2H), 7.25-7.09 (m, 7H), 3.86 (s, 3H), 3.80 (m, 1H), 3.61 (m, 1H), 3.46 (m, 1H), 2.90 (m, 1H), 2.78-2.57 (m, 4H), 2.38-2.18 (m, 2H), 0.83 (s, 9H); MS 524.1 (M+1).

Step E: 4-{3-[2-(3-Hydroxy-4-phenyl-butyl)-5-oxo-pyrrolidin-1-yl]-propyl}-benzoic acid methyl ester. To a solution of 4-(3-{2-[3-(tert-butyl-dimethyl-silanyloxy)-4-phenyl-butyl]-5-oxo-pyrrolidin-1-yl}-propyl)-benzoic acid methyl ester (3.37 g, 6.43 mmol) in THF (40 mL) at 0° C. was added tetra-butylammonium fluoride (1M in THF, 9.6 mL, 9.6 mmol). The reaction mixture was stirred at room temperature for 18 h and the volatiles were removed in vacuo. EtOAc was added and the organic solution was washed with saturated aqueous $NaHCO_3$ (2×), water (1×), and brine (1×). The organic solution was dried ($MgSO_4$), filtered and concentrated. The residue was purified by medium pressure chromatography eluting with EtOAc to yield 2.28 g of 4-{3-[2-(3-hydroxy-4-phenyl-butyl)-5-oxo-pyrrolidin-1-yl]-propyl}-benzoic acid methyl ester. $^1$H NMR ($CDCl_3$) (selected peaks) δ7.91 (d, 2H), 7.32-7.15 (m, 7H), 3.86 (s, 3H), 3.75 (m, 1H), 3.63 (m, 1H), 3.54 (m, 1H), 2.94 (m, 1H), 2.78 (m, 1H), 2.61 (m, 3H); MS 410.1 (M+1).

Step F: 4-{3-[2-(3-Hydroxy-4-phenyl-butyl)-5-oxo-pyrrolidin-1-yl]-propyl}-benzoic acid.

To a solution of 4-{3-[2-(3-hydroxy-4-phenyl-butyl)-5-oxo-pyrrolidin-1-yl]-propyl}-benzoic acid methyl ester (2.28 g, 5.57 mmol) in MeOH (20 mL) was added 2N NaOH (5 mL). The reaction mixture was stirred at room temperature for 20 h and was heated under reflux for 3 h. The volatiles were removed in vacuo and the residue was diluted with $CH_2Cl_2$ and 1 N HCl. The aqueous solution was extracted with $CH_2Cl_2$ (2×) and the combined organic extracts were washed with brine. The organic solution was dried ($MgSO_4$), filtered and concentrated to yield the title compound (2.03 g). $^1$H NMR ($CDCl_3$) δ7.98 (d, 2H), 7.34-7.18 (m, 7H), 3.80 (m, 1H), 3.67 (m, 1H), 3.58 (m, 1H), 2.97 (m, 1H), 2.81 (m, 1H), 2.68 (m, 3H), 2.45-2.27 (m, 2H), 2.13-1.30 (m, 9H); MS 396.3 (M+1), 394.2 (M−1).

EXAMPLE 1B 4-(3-{2-[3-Hydroxy-4-(3-trifluoromethyl-phenyl)-butyl]-5-oxo-pyrrolidin-1-yl}-propyl)-benzoic acid Step A: 5-[3-Oxo-4-(3-trifluoromethyl-phenyl)-butyl]-pyrrolidin-2-one Magnesium coils (1.13 g) were stirred under vacuum in a round bottom flask for 60 h. Anhydrous Et$_2$O (5 mL) was added and the reaction mixture was cooled to 0° C. A solution of 3-trifluoromethylbenzyl chloride (1.0 mL, 7.5 mmol) in Et$_2$O (25 mL) was added dropwise over 3 h. The reaction mixture was stirred for an additional 2.5 h. The solution was slowly added via a syringe and filtered through a Nylon Acrodisc™ syringe filter into a solution of tetrahydro-pyrrolizine-3,5-dione (650 mg, 4.68 mmol) in CH$_2$Cl$_2$ (30 mL) at 0° C. After 2 h, the reaction mixture was quenched with 1 N HCl and the aqueous solution was washed with CH$_2$Cl$_2$ (2×). The organic solutions were combined, dried (MgSO$_4$), filtered and concentrated. Medium pressure chromatography (1:1 hexanes:EtOAc) provided 5-[3-oxo-4-(3-trifluoromethyl-phenyl)-butyl]-pyrrolidin-2-one (1.376 g). $^1$H NMR (CDCl$_3$) δ7.38 (m, 4H), 3.78 (s, 2H), 3.61 (m, 1H), 2.58 (t, 2H), 2.30 (m, 2H), 2.20 (m, 1H), 2.86-1.59 (m, 3H).

Step B: 5-[3-Hydroxy-4-(3-trifluoromethyl-phenyl)-butyl]-pyrrolidin-2-one. Analogous to the procedure described for Example 1A, Step B, 5-[3-oxo-4-(3-trifluoromethyl-phenyl)-butyl]-pyrrolidin-2-one (1.37 g, 4.59 mmol) was reduced with NaBH$_4$ (174 mg) at 0° C. over 2 h. Purification by medium pressure chromatography (2% MeOH in CH$_2$Cl$_2$) provided 5-[3-hydroxy-4-(3-trifluoromethyl-phenyl)-butyl]-pyrrolidin-2-one (1.19 g). $^1$H NMR (CDCl$_3$) δ7.42 (m, 4H), 6.26 (m, 1H), 3.82 (m, 1H), 3.65 (m, 1H), 2.84 (m, 1H), 2.72 (m, 1H), 2.27 (m, 3H), 1.86 (m, 1H), 1.75-1.42 (m, 5H); MS 302.2 (M+1).

Step C: 5-[3-(tert-Butyl-dimethyl-silanyloxy)-4-(3-trifluoromethyl-phenyl)-butyl]-pyrrolidin-2-one. Analogous to the procedure described for Example 1A, Step C, 5-[3-hydroxy-4-(3-trifluoromethyl-phenyl)-butyl]-pyrrolidin-2-one (1.19 g, 3.95 mmol) was protected with tert-butyldimethylsilyl chloride (893 mg, 6.22 mmol). Purification by medium pressure chromatography eluting with EtOAc provided 5-[3-(tert-butyl-dimethyl-silanyloxy)-4-(3-trifluoromethyl-phenyl)-butyl]-pyrrolidin-2-one. $^1$H NMR (CDCl$_3$) δ7.47-7.32 (m, 4H), 5.73 (m, 1H), 3.86 (m, 1H), 3.59 (m, 1H), 2.75 (m, 2H), 2.35-2.20 (m, 3H), 1.70-1.40 (m, 5H), 0.81 (s, 9H), −0.05 (d, 3H), −0.3 (d, 3H); MS 416.1 (M+1).

Step D: 4-(3-{2-[3-(tert-Butyl-dimethyl-silanyloxy)-4-(3-trifluoromethyl-phenyl)-butyl]5-oxo-pyrrolidin-1-yl}-propyl)-benzoic acid methyl ester. Analogous to the procedure described for Example 1A, Step D, 5-[3-(tert-butyl-dimethyl-silanyloxy)-4-(3-trifluoromethyl-phenyl)-butyl]-pyrrolidin-2-one (250 mg, 0.602 mmol) was alkylated with NaHMDS (1M in THF, 0.72 mL, 0.72 mmol) and 4-(3-bromo-propyl)-benzoic acid methyl ester (170 mg, 0.663 mmol) to yield 4-(3-{2-[3-(tert-butyl-dimethyl-silanyloxy)-4-(3-trifluoromethyl-phenyl)-butyl]-5-oxo-pyrrolidin-1-yl}-propyl)-benzoic acid methyl ester (300 mg). MS 592.1 (M+1).

Step E: 4-(3-{2-[3-Hydroxy-4-(3-trifluoromethyl-phenyl)-butyl]-5-oxo-pyrrolidin-1-yl}-propyl)-benzoic acid methyl ester. 4-(3-{2-[3-Hydroxy-4-(3-trifluoromethyl-phenyl)-butyl]-5-oxo-pyrrolidin-1-yl}-propyl)-benzoic acid methyl ester was prepared Analogous to the procedure described for Example 1A, Step E. $^1$H NMR (CDCl$_3$) (selected peaks) δ7.91 (d, 2H), 7.49-7.35 (m, 4H), 7.22 (d, 2H), 3.85 (s, 3H), 3.80 (m, 1H), 3.65 (m, 1H), 3.55 (m, 1H), 2.98-2.61 (m, 5H).

Step F: 4-(3-{2-[3-Hydroxy-4-(3-trifluoromethyl-phenyl)-butyl]-5-oxo-pyrrolidin-1-yl}-propyl)-benzoic acid. Analogous to the procedure described for Example 1A, Step F, 4-(3-{2-[3-hydroxy-4-(3-trifluoromethyl-phenyl)-butyl]-5-oxo-pyrrolidin-1-yl}-propyl)-benzoic acid methyl ester was hydrolyzed at room temperature over 24 h to generate 4-(3-{2-[3-hydroxy-4-(3-trifluoromethyl-phenyl)-butyl]-5-oxo-pyrrolidin-1-yl}-propyl)-benzoic acid. $^1$H NMR (CDCl$_3$) δ7.98 (d, 2H), 7.52-7.37 (m, 4H), 7.26 (d, 2H), 3.82 (m, 1H), 3.68 (m, 1H), 3.58 (m, 1H), 2.98-2.66 (m, 5H), 2.34 (m, 2H), 2.09 (m, 1H), 1.95-1.37 (m, 7H); MS 464.2 (M+1).

EXAMPLE 1C 4-(3-{2-[4-(3-Chloro-phenyl)-3-hydroxy-butyl]-5-oxo-pyrrolidin-1-yl}-propyl)-benzoic acid Step A: 5-[4-(3-Chloro-phenyl)-3-oxo-butyl]-pyrrolidin-2-one. Analogous to the procedure described for Example 1A, Step A, tetrahydro-pyrrolizine-3,5-dione (2 g, 14 mmol) was reacted with 3-chlorobenzylmagnesium chloride (0.25M in Et$_2$O, 62 mL, 15.5 mmol) over 2 h. Purification by medium pressure chromatography eluting with a solvent gradient (2:1 hexanes:EtOAc to EtOAc to 5% MeOH in CH$_2$Cl$_2$) provided 5-[4-(3-chloro-phenyl)-3-oxo-butyl]-pyrrolidin-2-one (1.9142 g). $^1$H NMR (CDCl$_3$) δ7.27 (m, 2H), 7.19 (m, 1H), 7.08 (m, 1H), 6.27 (br, 1H), 3.68 (s, 2H), 3.60 (m, 1H), 2.52 (t, 2H), 2.29 (m, 2H), 2.21 (m, 1H), 1.88-1.60 (m, 3H); MS 266.2 (M+1), 264.2 (M−1).

Step B: 5-[4-(3-Chloro-phenyl)-3-hydroxy-butyl]-pyrrolidin-2-one. Analogous to the procedure described for Example 1A, Step B, 5-[4-(3-chloro-phenyl)-3-oxo-butyl]-pyrrolidin-2-one (1.9 g, 7.15 mmol) was reduced with NaBH$_4$ (135 mg, 3.57 mmol). Purification by medium pressure chromatography eluting with a solvent gradient (1:1 hexanes:EtOAc to EtOAc to 1% MeOH in CH$_2$Cl$_2$ to 4% MeOH in CH$_2$Cl$_2$ to 8% MeOH in CH$_2$Cl$_2$) provided 5-[4-(3-chloro-phenyl)-3-hydroxy-butyl]-pyrrolidin-2-one (1.53 g). $^1$H NMR (CDCl$_3$) δ7.22 (m, 3H), 7.07 (m, 1H), 6.51 (d, 1H), 3.82 (m, 1H), 3.66 (m, 1H), 2.77 (m, 1H), 2.66 (m, 1H), 2.33-2.19 (m, 3H), 2.04 (d, 1H), 1.74-1.45 (m, 5H); MS 268.2 (M+1).

Step C: 5-[3-(tert-Butyl-dimethyl-silanyloxy)-4-(3-chloro-phenyl)-butyl]-pyrrolidin-2-one. Analogous to the procedure described for Example 1A, Step C, 5-[4-(3-chloro-phenyl)-3-hydroxy-butyl]-pyrrolidin-2-one (1.53 g, 5.71 mmol) was reacted with tert-butyldimethylsilyl chloride (0.97 g, 6.4 mmol). Purification by medium pressure chromatography using a solvent gradient (1:1 hexanes:EtOAc to EtOAc to 1% MeOH in CH$_2$Cl$_2$ to 2% MeOH in CH$_2$Cl$_2$ to 4% MeOH in CH$_2$Cl$_2$) provided 5-[3-(tert-butyl-dimethyl-silanyloxy)-4-(3-chloro-phenyl)-butyl]-pyrrolidin-2-one (1.77 g). $^1$H NMR (CDCl$_3$) δ7.16 (m, 3H), 7.01 (m, 1H), 5.61 (d, 1H), 3.83 (m, 1H), 3.58 (m, 1H), 2.68 (m, 2H), 2.28 (m, 3H), 1.73-1.36 (m, 5H), 0.84 (s, 9H), −0.05 (s, 3H), −0.2 (d, 3H).

Step D: 4-(3-{2-[3-(tert-Butyl-dimethyl-silanyloxy)-4-(3-chloro-phenyl)-butyl]-5-oxo-pyrrolidin-1-yl}-propyl)-benzoic acid methyl ester. Analogous to the procedure described for Example 1A, Step D, 5-[3-(tert-butyl-dimethyl-silanyloxy)-4-(3-chloro-phenyl)-butyl]-pyrrolidin-2-one (246.5 mg, 0.645 mmol) was alkylated with NaHMDS (1M in THF, 0.77 mL, 0.77 mmol) and 4-(3-bromo-propyl)-benzoic acid methyl ester (200 mg, 0.767 mmol). Purification by medium pressure chromatography (5:1 hexanes:EtOAc to 1:1 hexanes:EtOAc to EtOAc to 1% MeOH in CH$_2$Cl$_2$ to 5% MeOH in CH$_2$Cl$_2$) provided 5-[3-(tert-butyl-dimethyl-silanyloxy)-4-(3-chloro-phenyl)-butyl]-pyrrolidin-2-one (246.3 mg). $^1$H NMR (CDCl$_3$) δ7.94 (d, 2H), 7.25-7.13 (m, 5H), 7.01 (m, 1H), 3.88 (s, 3H), 3.82 (m, 1H), 3.66 (m, 1H), 3.50 (m, 1H), 2.94 (m, 1H), 2.73-2.57

(m, 4H), 2.47-2.27 (m, 2H), 2.12–11.23 (m, 8H), 0.84 (s, 9H), −0.05 (d, 3H), −0.2 (d, 3H); MS 558.5 (M+).

Step E: 4-(3-{2-[4-(3-Chloro-phenyl)-3-hydroxy-butyl]-5-oxo-pyrrolidin-1-yl}-propyl)-benzoic acid methyl ester. 4-(3-{2-[4-(3-Chloro-phenyl)-3-hydroxy-butyl]-5-oxo-pyrrolidin-1-yl}-propyl)-benzoic acid methyl ester was prepared Analogous to the procedure described for Example 1A, Step E after purification by medium pressure chromatography (CH$_2$Cl$_2$ to 1% MeOH in CH$_2$Cl$_2$ to 2% MeOH in CH$_2$Cl$_2$ to 5% MeOH in CH$_2$Cl$_2$). $^1$H NMR (CDCl$_3$) δ7.94 (d, 2H), 7.25-7.19 (m, 5H), 7.07 (m, 1H), 3.88 (s, 3H), 3.78 (m, 1H), 3.66 (m, 1H), 3.58 (m, 1H), 2.97 (m, 1H), 2.76 (m, 1H), 2.68-2.58 (m, 3H), 2.45-2.27 (m, 2H), 2.07 (m, 1H), 1.95-1.34 (m, 8H).

Step F: 4-(3-{2-[4-(3-Chloro-phenyl)-3-hydroxy-butyl]-5-oxo-pyrrolidin-1-yl}-propyl)-benzoic acid. Analogous to the procedure described for Example 1A, Step F, 4-(3-{2-[4-(3-chloro-phenyl)-3-hydroxy-butyl]-5-oxo-pyrrolidin-1-yl}-propyl)-benzoic acid methyl ester was hydrolyzed with 6N NaOH at room temperature over 24 h to generate 4-(3-{2-[4-(3-chloro-phenyl)-3-hydroxy-butyl]-5-oxo-pyrrolidin-1-yl}-propyl)-benzoic acid. $^1$H NMR (CDCl$_3$) δ7.98 (d, 2H), 7.27-7.09 (m, 6H), 3.81 (m, 1H), 3.65 (m, 2H), 2.99 (m, 2H), 2.75 (m, 3H), 2.39 (m, 2H), 2.20-1.30 (m, 9H).

EXAMPLE 1D 4-(3-{2-[4-(3-Fluoro-phenyl)-3-hydroxy-butyl]-5-oxo-pyrrolidin-1-yl}-propyl)-benzoic acid Step A: 5-[4-(3-Fluoro-phenyl)-3-oxo-butyl]-pyrrolidin-2-one. Analogous to the procedure described for Example 1A, Step A, tetrahydro-pyrrolizine-3,5-dione (2 g, 14 mmol) was reacted with 3-fluorobenzylmagnesium chloride (0.25M in Et$_2$O, 62 mL, 15.5 mmol) over 2.5 h. Purification by medium pressure chromatography using a solvent gradient (1:1 hexanes:EtOAc to 2:1 EtOAc:hexanes to EtOAc to 2% MeOH in CH$_2$Cl$_2$ to 10% MeOH in CH$_2$Cl$_2$) provided 5-[4-(3-fluoro-phenyl)-3-oxo-butyl]-pyrrolidin-2-one (2.1730 g). $^1$H NMR (CDCl$_3$) δ7.32-7.27 (m, 1H), 7.00-6.90 (m, 3H), 6.12 (bs, 1H), 3.69 (s, 2H), 3.59 (m, 1H), 2.52 (t, 2H), 2.30 (m, 2H), 2.19 (m, 1H), 1.75 (m, 2H), 1.65 (m, 1H).

Step B: 5-[4-(3-Fluoro-phenyl)-3-hydroxy-butyl]-pyrrolidin-2-one. Analogous to the procedure described for Example 1A, Step B, 5-[4-(3-fluoro-phenyl)-3-oxo-butyl]-pyrrolidin-2-one (2.17 g, 8.71 mmol) was reduced with NaBH$_4$ (165 mg, 4.35 mmol). Purification by medium pressure chromatography using a solvent gradient (1:1 hexanes:EtOAc to EtOAc to 1% MeOH in CH$_2$Cl$_2$ to 3% MeOH in CH$_2$Cl$_2$ to 6% MeOH in CH$_2$Cl$_2$) provided 5-[4-(3-fluoro-phenyl)-3-hydroxy-butyl]-pyrrolidin-2-one (2.23 g). $^1$H NMR (CDCl$_3$) δ7.27 (m, 1H), 6.94 (m, 3H), 6.38 (m, 1H), 3.82 (m, 1H), 3.66 (m, 1H), 2.79 (m, 1H), 2.67 (m, 1H), 2.33-2.21 (m, 3H), 1.92 (d, 1H), 1.75-1.40 (m, 5H); MS 252.2 (M+1).

Step C: 5-[3-(tert-Butyl-dimethyl-silanyloxy)-4-(3-fluoro-phenyl)-butyl]-pyrrolidin-2-one. Analogous to the procedure described for Example 1A, Step C, 5-[4-(3-fluoro-phenyl)-3-hydroxy-butyl]-pyrrolidin-2-one (2.23 g, 8.87 mmol) was reacted with tert-butyldimethylsilyl chloride (1.47 g, 9.76 mmol). Purification by medium pressure chromatography using a solvent gradient (1:1 hexanes:EtOAc to EtOAc to 1% MeOH in CH$_2$Cl$_2$ to 2% MeOH in CH$_2$Cl$_2$ to 4% MeOH in CH$_2$Cl$_2$) provided 5-[3-(tert-butyl-dimethyl-silanyloxy)-4-(3-fluoro-phenyl)-butyl]-pyrrolidin-2-one (2.84 g). $^1$H NMR (CDCl$_3$) δ7.23 (m, 1H), 6.88 (m, 3H), 5.75 (m, 1H), 3.85 (m, 1H), 3.57 (m, 1H), 2.71 (m, 2H), 2.30 (m, 2H), 2.25 (m, 1H), 1.70-1.38 (m, 5H), 0.84 (s, 9H), 0 (s, 3H), −0.2 (s, 3H).

Step D: 4-(3-{2-[3-(tert-Butyl-dimethyl-silanyloxy)-4-(3-fluoro-phenyl)-butyl]-5-oxo-pyrrolidin-1-yl}-propyl)-benzoic acid methyl ester. Analogous to the procedure described in Example 1A, Step D, 5-[3-(tert-butyl-dimethyl-silanyloxy)-4-(3-fluoro-phenyl)-butyl]-pyrrolidin-2-one (254.7 mg, 0.697 mmol) was alkylated with NaHMDS (1M in THF, 0.84 mL, 0.84 mmol) and 4-(3-bromo-propyl)-benzoic acid methyl ester (200 mg, 0.778 mmol). Purificaton by medium pressure chromatography (5:1 hexanes:EtOAc to 1:1 hexanes:EtOAc to EtOAc to 1% MeOH in CH$_2$Cl$_2$ to 5% MeOH in CH$_2$Cl$_2$) provided 4-(3-{2-[3-(tert-butyl-dimethyl-silanyloxy)-4-(3-fluoro-phenyl)-butyl]-5-oxo-pyrrolidin-1-yl}-propyl)-benzoic acid methyl ester (275.3 mg). $^1$H NMR (CDCl$_3$) (selected peaks) δ7.94 (d, 2H), 7.23 (m, 3H), 6.87 (m, 3H), 3.88 (s, 3H), 3.86 (m, 1H), 3.63 (m, 1H), 3.50 (m, 1H), 2.94 (m, 1H), 0.84 (s, 9H).

Step E: 4-(3-{2-[4-(3-Fluoro-phenyl)-3-hydroxy-butyl]-5-oxo-pyrrolidin-1-yl}-propyl)-benzoic acid methyl ester. Analogous to the procedure described for Example 1A, Step E, 4-(3-{2-[3-(tert-butyl-dimethyl-silanyloxy)-4-(3-fluoro-phenyl)-butyl]-5-oxo-pyrrolidin-1-yl}-propyl)-benzoic acid methyl ester (275.3 mg, 0.508 mmol) was deprotected to yield 4-(3-{2-[4-(3-fluoro-phenyl)-3-hydroxy-butyl]-5-oxo-pyrrolidin-1-yl}-propyl)-benzoic acid methyl ester (217.2 mg). Purification was performed by medium pressure chromatography eluting with a solvent gradient (CH$_2$Cl$_2$ to 1% MeOH in CH$_2$Cl$_2$ to 2% MeOH in CH$_2$Cl$_2$ to 5% MeOH in CH$_2$Cl$_2$). $^1$H NMR (CDCl$_3$) δ7.94 (d, J=7.88 Hz, 2H), 7.27 (m, 3H), 6.93 (m, 3H), 3.88 (s, 3H), 3.78 (m, 1H), 3.66 (m, 1H), 3.57 (m, 1H), 2.97 (m, 1H), 2.78 (m, 1H), 2.64 (m, 4H), 2.45-2.25 (m, 2H), 2.07 (m, 1H), 1.95-1.30 (m, 7H).

Step F: 4-(3-{2-[4-(3-Fluoro-phenyl)-3-hydroxy-butyl]-5-oxo-pyrrolidin-1-yl}-propyl)-benzoic acid. Analogous to the procedure described for Example 1A, Step F, 4-(3-{2-[4-(3-fluoro-phenyl)-3-hydroxy-butyl]-5-oxo-pyrrolidin-1-yl}-propyl)-benzoic acid methyl ester was hydrolyzed with 6N NaOH at room temperature over 24 h to generate 4-(3-{2-[4-(3-fluoro-phenyl)-3-hydroxy-butyl]-5-oxo-pyrrolidin-1-yl}-propyl)-benzoic acid. $^1$H NMR (CDCl$_3$) δ7.99 (d, 2H), 7.26 (m, 3H), 6.95 (m, 3H), 3.81 (m, 1H), 3.65 (m, 2H), 3.01 (m, 1H), 2.86-2.66 (m, 3H), 2.39 (m, 2H), 2.08 (m, 1H), 2.00-1.30 (m, 9H).

EXAMPLE 1E 4-(3-{2-[3-Hydroxy-4-(3-phenoxy-phenyl)-butyl]-5-oxo-pyrrolidin-1-yl}-propyl)-benzoic acid Step A: 5-[3-Oxo-4-(3-phenoxy-phenyl)-butyl]-pyrrolidin-2-one. Analogous to the procedure described for Example 1B, Step A, tetrahydro-pyrrolizine-3,5-dione (650 mg, 4.68 mmol) and 3-phenoxybenzyl chloride (1.20 g, 5.49 mmol) were reacted over 3.5 h to provide 5-[3-oxo-4-(3-phenoxy-phenyl)-butyl]-pyrrolidin-2-one (924 mg). $^1$H NMR (CDCl$_3$) δ7.30 ( m, 3H), 7.10 (m, 1H), 6.99 (m, 2H), 6.92-6.84 (m, 3H), 3.66 (s, 2H), 3.57 (m, 1H), 2.52 (t, 2H), 2.27 (m, 2H), 2.17 (m, 1H), 1.80-1.58 (m, 3H).

Step B: 5-[3-Hydroxy-4-(3-phenoxy-phenyl)-butyl]-pyrrolidin-2-one. Analogous to the procedure described for Example 1A, Step B, 5-[3-oxo-4-(3-phenoxy-phenyl)-butyl]-pyrrolidin-2-one (923.6 mg, 2.86 mmol) was reduced with NaBH$_4$ (54 mg, 1.4 mmol). Purification by medium pressure chromatography (1:1 hexanes:EtOAc to 2% MeOH in CH$_2$Cl$_2$ to 4% MeOH in CH$_2$Cl$_2$ to 10% MeOH in CH₂Cl₂) provided 5-[3-hydroxy-4-(3-phenoxy-phenyl)-butyl]-pyrrolidin-2-one (668.3 mg). ¹H NMR (CDCl₃) δ7.31 (m, 2H), 7.23 (m, 1H), 7.08 (m, 1H), 6.97 (d, 2H), 6.91 (d, 1H), 6.84 (m, 2H), 3.80 (m, 1H), 3.73 (m, 1H), 2.77-2.03 (m, 2H), 2.40 (m, 2H), 2.24 (m, 1H), 1.75-1.41 (m, 5H); MS 326.3 (M+1).

Step C: 5-[3-(tert-Butyl-dimethyl-silanyloxy)-4-(3-phenoxy-phenyl)-butyl]-pyrrolidin-2-one. Analogous to the procedure described for Example 1A, Step C, 5-[3-hydroxy-4-(3-phenoxy-phenyl)-butyl]-pyrrolidin-2-one (668.3 mg, 2.05 mmol) was reacted with tert-butyldimethylsilyl chloride (341 mg, 2.26 mmol). Purification by medium pressure chromatography (CH₂Cl₂ to 1% MeOH in CH₂Cl₂ to 2% MeOH in CH₂Cl₂) provided 5-[3-(tert-butyl-dimethyl-silanyloxy)-4-(3-phenoxy-phenyl)-butyl]-pyrrolidin-2-one (673 mg). ¹H NMR (CDCl₃) δ7.32 (m, 2H), 7.22 (m, 1H), 7.09 (m, 1H), 6.99 (d, 2H), 6.89 (d, 1H), 6.83 (m, 2H), 3.85 (m, 1H), 3.58 (m, 1H), 2.76-2.62 (m, 2H), 2.32 (m, 2H), 2.23 (m, 1H), 1.73-1.34 (m, 5H), 0.84 (s, 9H), −0.03 (d, 3H), −0.16 (d, 3H); MS 440.7 (M+1).

Step D: 4-(3-{2-[3-(tert-Butyl-dimethyl-silanyloxy)-4-(3-phenoxy-phenyl)-butyl]-5-oxo-pyrrolidin-1-yl}-propyl)-benzoic acid methyl ester. Analogous to the procedure described for Example 1A, Step D, 5-[3-(tert-butyl-dimethyl-silanyloxy)-4-(3-phenoxy-phenyl)-butyl]-pyrrolidin-2-one (200 mg, 0.455 mmol) was alkylated with NaHMDS (1M in THF, 0.55 mL, 0.55 mmol) and 4-(3-bromo-propyl)-benzoic acid methyl ester (128 mg, 0.501 mmol) to yield 4-(3-{2-[3-(tert-butyl-dimethyl-silanyloxy)-4-(3-phenoxy-phenyl)-butyl]-5-oxo-pyrrolidin-1-yl}-propyl)-benzoic acid methyl ester (173.1 mg). ¹H NMR (CDCl₃) δ7.94 (d, 2H), 7.32 (m, 2H), 7.25-7.19 (m, 3H), 7.09 (m, 1H), 6.98 (d, 2H), 6.88-6.81 (m, 3H), 3.88 (s, 3H), 3.84 (m, 1H), 3.64 (m, 1H), 3.50 (m, 1H), 2.95 (m, 1H), 2.76-2.57 (m, 4H), 2.37 (m, 2H), 2.03 (m, 1H), 1.92-1.67 (m, 3H), 1.56 (m, 1H), 1.46-1.25 (m, 3H), 0.84 (s, 9H), −0.04 (d, 3H), −0.15 (d, 3H).

Step E: 4-(3-{2-[3-Hydroxy-4-(3-phenoxy-phenyl)-butyl]-5-oxo-pyrrolidin-1-yl}-propyl)-benzoic acid methyl ester. 4-(3-{2-[3-Hydroxy-4-(3-phenoxy-phenyl)-butyl]-5-oxo-pyrrolidin-1-yl}-propyl)-benzoic acid methyl ester was prepared analogous to the procedure described for Example 1A, Step E after purification by medium pressure chromatography (CH₂Cl₂ to 1% MeOH in CH₂Cl₂ to 2% MeOH in CH₂Cl₂ to 5% MeOH in CH₂Cl₂). ¹H NMR (CDCl₃) δ7.94 (d, 2H), 7.35-7.23 (m, 5H), 7.11 (m, 1H), 7.00 (d, 2H), 6.93-6.85 (m, 3H), 3.88 (s, 3H), 3.77 (m, 1H), 3.70-3.53 (m, 2H), 2.97 (m, 1H), 2.77 (m, 1H), 2.62 (m, 3H), 2.46-2.26 (m, 2H), 2.06 (m, 1H), 1.96-1.28 (m, 7H).

Step F: 4-(3-{2-[3-Hydroxy-4-(3-phenoxy-phenyl)-butyl]-5-oxo-pyrrolidin-1-yl}-propyl)-benzoic acid. Analogous to the procedure described for Example 1A, Step F, 4-(3-{2-[3-hydroxy-4-(3-phenoxy-phenyl)-butyl]-5-oxo-pyrrolidin-1-yl}-propyl)-benzoic acid methyl ester was hydrolyzed with 6N NaOH at room temperature over 24 h to generate 4-(3-{2-[3-hydroxy-4-(3-phenoxy-phenyl)-butyl]-5-oxo-pyrrolidin-1-yl}-propyl)-benzoic acid. ¹H NMR (CDCl₃) δ7.99 (d, 2H), 7.37-7.26 (m, 5H), 7.12 (m, 1H), 7.03-6.88 (m, 5H), 3.82 (m, 1H), 3.66 (m, 2H), 3.00 (m, 1H), 2.85-2.60 (m, 4H), 2.41 (m, 2H), 2.09 (m, 1H), 2.03-1.28 (m, 8H).

EXAMPLE 1F

4-{3-[2-(4-Biphenyl-3-yl-3-hydroxy-butyl)-5-oxo-pyrrolidin-1-yl]-propyl}-benzoic acid Step A: 5-(3-Bromo-3-oxo-butyl)-pyrrolidin-2-one. Analogous to the procedure described for Example 1A, Step A, tetrahydro-pyrrolizine-3,5-dione (5 g, 36 mmol) was reacted with 3-bromobenzylmagnesium bromide (0.25M in Et₂O, 155 mL, 38.8 mmol) over 2 h. Purification by medium pressure chromatography using a solvent gradient (1:1 hexanes:EtOAc to EtOAc to 5% MeOH in CH₂Cl₂) provided 5-(3-bromo-3-oxo-butyl)-pyrrolidin-2-one (7.84 g). ¹H NMR (CDCl₃) δ7.41-7.11 (m, 4H), 6.24 (bs, 1H), 3.67 (s, 2H), 3.60 (m, 1H), 2.52 (t, 2H), 2.32 (m, 2H), 2.20 (m, 1H), 1.88-1.60 (m, 3H).

Step B: 5-(3-Bromo-3-hydroxy-butyl)-pyrrolidin-2-one. Analogous to the procedure described for Example 1A, Step B, 5-(3-bromo-3-oxo-butyl)-pyrrolidin-2-one (7.84 g, 25.3 mmol) was reduced with NaBH₄ (480 mg, 12.6 mmol). Purification by medium pressure chromatography using a solvent gradient (1:1 hexanes:EtOAc to EtOAc to 1% MeOH in CH₂Cl₂ to 3% MeOH in CH₂Cl₂ to 5% MeOH in CH₂Cl₂ to 8% MeOH in CH₂Cl₂) provided 5-(3-bromo-3-hydroxy-butyl)-pyrrolidin-2-one (6.76 g). ¹H NMR (CDCl₃) δ7.36-7.09 (m, 4H), 6.27 (m, 1H), 3.78 (m, 1H), 3.63 (m, 1H), 2.75 (m, 1H), 2.62 (m, 1H), 2.32-2.18 (m, 3H), 1.88 (m, 1H), 1.73-1.42 (m, 5H); MS 312.2, 314. (M+).

Step C: 5-[3-Bromo-3-(tert-butyl-dimethyl-silanyloxy)-butyl]-pyrrolidin-2-one. Analogous to the procedure described for Example 1A, Step C, 5-(3-bromo-3-hydroxy-butyl)-pyrrolidin-2-one (6.76 g, 21.6 mmol) was reacted with tert-butyldimethylsilyl chloride (3.59 g, 23.8 mmol). Purification by medium pressure chromatography using a solvent gradient (CH₂Cl₂ to 1% MeOH in CH₂Cl₂ to 3% MeOH in CH₂Cl₂ to 5% MeOH in CH₂Cl₂ to 8% MeOH in CH₂Cl₂) provided 5-[3-bromo-3-(tert-butyl-dimethyl-silanyloxy)-butyl]-pyrrolidin-2-one (7.45 g). ¹H NMR (CDCl₃) δ7.30 (m, 2H), 7.12 (m, 1H), 7.04 (m, 1H), 5.71 (m, 1H), 3.81 (m, 1H), 3.56 (m, 1H), 2.66 (m, 2H), 2.32-2.17 (m, 3H), 1.70-1.35 (m, 5H), 0.82 (s, 9H), −0.06 (d, 3H), −0.24 (d, 3H); MS 426.2, 428.2 (M+).

Step D: 5-[4-Biphenyl-3-yl-3-(tert-butyl-dimethyl-silanyloxy)-butyl]-pyrrolidin-2-one. To a solution of 5-[3-bromo-3-(tert-butyl-dimethyl-silanyloxy)-butyl]-pyrrolidin-2-one (750 mg, 1.76 mmol) in DME (15 mL) was added phenylboronic acid (236 mg, 1.93 mmol). Palladium acetate (26.8 mg, 0.120 mmol) and tri-o-tolylphosphine (39.5 mg, 0.130 mmol) were added, followed by a solution of Na₂CO₃ (373 mg, 3.52 mmol) in water (1.8 mL). The reaction mixture was heated under reflux for 24 h. The reaction mixture was cooled and the volatiles were removed in vacuo. The residue was diluted with brine and EtOAc. The aqueous solution was washed with EtOAc (3×) and the combined organic extracts were dried (MgSO₄), filtered and concentrated. Purification by medium pressure chromatography eluting with a solvent gradient (1:1 hexanes:EtOAc to EtOAc to 1% MeOH in CH₂Cl₂ to 3% MeOH in CH₂Cl₂ to 5% MeOH in CH₂Cl₂) provided 5-[4-biphenyl-3-yl-3-(tert-butyl-dimethyl-silanyloxy)-butyl]-pyrrolidin-2-one (717.3 mg). ¹H NMR (CDCl₃) δ7.57 (m, 2H), 7.43 (m, 2H), 7.33 (m, 3H), 7.11 (m, 2H), 5.78 (m, 1H), 3.91 (m, 1H), 3.59 (m, 1H), 2.76 (m, 2H), 2.27 (m, 3H), 1.73-1.38 (m, 5H), 0.83 (s, 9H), −0.03 (d, 3H), −0.16 (d, 3H); MS 424.3 (M+1).

Step E: 4-(3-{2-[4-Biphenyl-3-yl-3-(tert-butyl-dimethyl-silanyloxy)-butyl]-5-oxo-pyrrolidin-1-yl}-propyl)-benzoic acid methyl ester. Analogous to the procedure described for Example 1A, Step D, 5-[4-biphenyl-3-yl-3-(tert-butyl-dimethyl-silanyloxy)-butyl]-pyrrolidin-2-one (5.116 g, 12.08 mmol) was alkylated with 4-(3-bromo-propyl)-benzoic acid methyl ester (3.41 g, 13.3 mmol) over 20 h. Purification by medium pressure chromatography using a solvent gradient (5:1 hexanes:EtOAc to 1:1 hexanes:EtOAc to EtOAc to 1% MeOH in CH₂Cl₂ to 5% MeOH in CH₂Cl₂)

provided 4-(3-{2-[4-biphenyl-3-yl-3-(tert-butyl-dimethyl-silanyloxy)-butyl]-5-oxo-pyrrolidin-1-yl}-propyl)-benzoic acid methyl ester (5.38 g). $^1$H NMR (CDCl$_3$) δ7.93 (d, 2H), 7.56 (d, 2H), 7.43 (m, 3H), 7.34 (m, 3H), 7.23 (m, 2H), 7.12 (m, 1H), 3.89 (m, 1H), 3.87 (s, 3H), 3.64 (m, 1H), 3.49 (m, 1H), 2.95-2.61 (m, 5H), 2.30 (m, 2H), 2.01 (m, 1H), 1.89-1.70 (m, 3H), 1.59-1.24 (m, 4H), 0.84 (s, 9H), −0.04 (d, 3H), −0.16 (d, 3H).

Step F: 4-{3-[2-(4-Biphenyl-3-yl-3-hydroxy-butyl)-5-oxo-pyrrolidin-1-yl]-propyl}-benzoic acid methyl ester. Analogous to the procedure described for Examples 1A, Step E, 4-(3-{2-[4-biphenyl-3-yl-3-(tert-butyl-dimethyl-silanyloxy)-butyl]-5-oxo-pyrrolidin-1-yl}-propyl)-benzoic acid methyl ester (5.38 g, 8.97 mmol) was deprotected. Purification by medium pressure chromatography using a solvent gradient (hexanes to 2:1 hexanes:EtOAc to 1:1 hexanes:EtOAc to 0.5% MeOH in CH$_2$Cl$_2$ to 1% MeOH in CH$_2$Cl$_2$) provided 4-{3-[2-(4-biphenyl-3-yl-3-hydroxy-butyl)-5-oxo-pyrrolidin-1-yl]-propyl}-benzoic acid methyl ester (3.70 g). $^1$H NMR (CDCl$_3$) δ7.93 (d, 2H), 7.57 (d, 2H), 7.40 (m, 6H), 7.24 (m, 2H), 7.17 (m, 1H), 3.86 (s, 3H), 3.80 (m, 1H), 3.66 (m, 1H), 3.56 (m, 1H), 2.97 (m, 1H), 2.90-2.60 (m, 4H), 2.33 (m, 2H), 2.07 (m, 1H), 1.98-1.34 (m, 8H).

Step G: 4-{3-[2-(4-Biphenyl-3-yl-3-hydroxy-butyl)-5-oxo-pyrrolidin-1-yl]-propyl}-benzoic acid. Analogous to the procedure described for Example 1A, Step F, 4-{3-[2-(4-biphenyl-3-yl-3-hydroxy-butyl)-5-oxo-pyrrolidin-1-yl]-propyl}-benzoic acid methyl ester (3.14 g, 6.47 mmol) was hydrolyzed with 6N NaOH (40 mL) in MeOH (160 mL) at room temperature over 24 h to generate 4-{3-[2-(4-biphenyl-3-yl-3-hydroxy-butyl)-5-oxo-pyrrolidin-1-yl]-propyl}-benzoic acid (2.73 g). $^1$H NMR (CDCl$_3$) δ7.98 (d, 2H), 7.57 (d, 2H), 7.40 (m, 6H), 7.26 (m, 2H), 7.18 (m, 1H), 3.85 (m, 1H), 3.68 (m, 1H), 3.59 (m, 1H), 2.98 (m, 1H), 2.88 (m, 1H), 2.70 (m, 3H), 2.36 (m, 2H), 2.08 (m, 1H), 1.85 (m, 3H), 1.69-1.35 (m, 4H); MS 470.1 (M−1), 472.2 (M+1).

EXAMPLE 1G 4-(3-{2-[4-(4-Fluoro-phenyl)-3-hydroxy-butyl]-5-oxo-pyrrolidin-1-yl}-propyl)-benzoic acid Step A: 5-[4-(4-Fluoro-phenyl)-3-oxo-butyl]-pyrrolidin-2-one. Analogous to the procedure described for Example 1A, Step A, tetrahydro-pyrrolizine-3,5-dione (1.41 g, 10.1 mmol) was reacted with 4-fluorobenzylmagnesium chloride (0.25M in Et$_2$O, 50 mL, 12.5 mmol) over 5 h. Purification by medium pressure chromatography (2% MeOH in CH$_2$Cl$_2$) provided 5-[4-(4-fluoro-phenyl)-3-oxo-butyl]-pyrrolidin-2-one (2.64 g). $^1$H NMR (CDCl$_3$) δ7.18 (m, 2H), 7.03 (m, 2H), 6.34 (m, 1H), 3.70 (s, 2H), 3.62 (m, 1H), 2.54 (t, 2H), 2.34-2.15 (m, 3H), 1.82-1.61 (m, 3H).

Step B: 5-[4-(4-Fluoro-phenyl)-3-hydroxy-butyl]-pyrrolidin-2-one. Analogous to the procedure described for Example 1A, Step B, 5-[4-(4-fluoro-phenyl)-3-oxo-butyl]-pyrrolidin-2-one (2.64 g, 10.6 mmol) was reduced with NaBH$_4$ (400 mg, 10.5 mmol) at room temperature for 1 h. Additional NaBH$_4$ (150 mg, 3.95 mmol) was added and the reaction mixture was stirred for 20 h. Purification by medium pressure chromatography using a solvent gradient (CH$_2$Cl$_2$ to 2% MeOH in CH$_2$Cl$_2$ to 4% MeOH in CH$_2$Cl$_2$) provided 5-[4-(4-fluoro-phenyl)-3-hydroxy-butyl]-pyrrolidin-2-one (2.01 g). $^1$H NMR (CDCl$_3$) δ7.14 (m, 2H), 6.98 (m, 2H), 6.78 (m, 1H), 3.76 (m, 1H), 3.65 (m, 1H), 2.76 (m, 1H), 2.64 (m, 1H), 2.32-2.18 (m, 4H), 1.72-1.47 (m, 5H).

Step C: 5-[3-(tert-Butyl-dimethyl-silanyloxy)-4-(4-fluoro-phenyl)-butyl]-pyrrolidin-2-one. Analogous to the procedure described for Example 1A, Step C, 5-[4-(4-fluoro-phenyl)-3-hydroxy-butyl]-pyrrolidin-2-one (1.95 g, 7.79 mmol) was reacted with tert-butyldimethylsilyl chloride (1.47 g, 9.76 mmol). Purification by medium pressure chromatography (1% MeOH in CH$_2$Cl$_2$) provided 5-[3-(tert-butyl-dimethyl-silanyloxy)-4-(4-fluoro-phenyl)-butyl]-pyrrolidin-2-one. $^1$H NMR (CDCl$_3$) δ7.12 (m, 2H), 6.97 (m, 2H), 5.75 (m, 1H), 3.83 (m, 1H), 3.60 (m, 1H), 2.71 (m, 2H), 2.36-2.24 (m, 3H), 1.70-1.38 (m, 5H), 0.84 (s, 9H), −0.05 (d, 3H), −0.2 (d, 3H).

Step D: 4-(3-{2-[3-(tert-Butyl-dimethyl-silanyloxy)-4-(4-fluoro-phenyl)-butyl]-5-oxo-pyrrolidin-1-yl}-propyl)-benzoic acid methyl ester. Analogous to the procedure described for Example 1A, Step D, 5-[3-(tert-butyl-dimethyl-silanyloxy)-4-(4-fluoro-phenyl)-butyl]-pyrrolidin-2-one (296 mg, 0.809 mmol) was alkylated with 4-(3-bromo-propyl)-benzoic acid methyl ester (276 mg, 1.07 mmol) over 72 h. Purification by medium pressure chromatography (1:1 hexanes:EtOAc) provided 4-(3-{2-[3-(tert-butyl-dimethyl-silanyloxy)-4-(4-fluoro-phenyl)-butyl]-5-oxo-pyrrolidin-1-yl}-propyl)-benzoic acid methyl ester (250 mg). $^1$H NMR (CDCl$_3$) (selected peaks) δ7.92 (d, 2H), 7.21 (d, 2H), 7.05 (m, 2H), 6.92 (m, 2H), 3.86 (s, 3H), 3.76 (m, 1H), 3.62 (m, 1H), 3.45 (m, 1H), 0.81 (s, 9H).

Step E: 4-(3-{2-[4-(4-Fluoro-phenyl)-3-hydroxy-butyl]-5-oxo-pyrrolidin-1-yl}-propyl)-benzoic acid methyl ester. Analogous to the procedure described for Example 1A, Step E, 4-(3-{2-[3-(tert-butyl-dimethyl-silanyloxy)-4-(4-fluoro-phenyl)-butyl]-5-oxo-pyrrolidin-1-yl}-propyl)-benzoic acid methyl ester (241.2 mg, 0.445 mmol) was deprotected to yield, after medium pressure chromatography (1:1 hexanes:EtOAc to EtOAc to 1% MeOH in CH$_2$Cl$_2$ to 3% MeOH in CH$_2$Cl$_2$ to 5% MeOH in CH$_2$Cl$_2$), 4-(3-{2-[4-(4-fluoro-phenyl)-3-hydroxy-butyl]-5-oxo-pyrrolidin-1-yl}-propyl)-benzoic acid methyl ester (61.1 mg). $^1$H NMR (CDCl$_3$) (selected peaks) δ7.93 (d, 2H), 7.24 (d, 2H), 7.14 (m, 2H), 7.00 (m, 2H), 3.88 (s, 3H), 3.80-3.51 (m, 3H), 2.98 (m, 1H), 2.32 (m, 2H).

Step F: 4-(3-{2-[4-(4-Fluoro-phenyl)-3-hydroxy-butyl]-5-oxo-pyrrolidin-1-yl}-propyl)-benzoic acid. Analogous to the procedure described for Example 1A, Step F, 4-(3-{2-[4-(4-fluoro-phenyl)-3-hydroxy-butyl]-5-oxo-pyrrolidin-1-yl}-propyl)-benzoic acid methyl ester (61.1 mg, 0.143 mmol) was hydrolyzed with 6N NaOH (1 mL) in MeOH (5 mL) at room temperature over 24 h. Purification by medium pressure chromatography eluting with a solvent gradient (CH$_2$Cl$_2$ to 2% MeOH in CH$_2$Cl$_2$ to 4% MeOH in CH$_2$Cl$_2$ to 6% MeOH in CH$_2$Cl$_2$ to 10% MeOH in CH$_2$Cl$_2$) provided the title compound (45 mg). $^1$H NMR (CDCl$_3$) δ7.97 (d, 2H), 7.25 (m, 2H), 7.14 (m, 2H), 6.99 (m, 2H), 3.75-3.58 (m, 3H), 2.97 (m, 1H), 2.69 (m, 4H), 2.40 (m, 2H), 2.15-1.35 (m, 9H); MS 413.8 (M+).

EXAMPLE 1H

4-{2-[2-(3-Hydroxy4-phenyl-butyl)-5-oxo-pyrrolidin-1-yl]-ethoxy}-benzoic acid

Step A: 4-(2-{2-[3-(tert-Butyl-dimethyl-silanyloxy)-4-phenyl-butyl]-5-oxo-pyrrolidin-1-yl}-ethoxy)-benzoic acid ethyl ester. Analogous to the procedure described for Example 1A, Step D, 5-[3-(tert-butyl-dimethyl-silanyloxy)-4-phenyl-butyl]-pyrrolidin-2-one (prepared in Example 1A, Step C) (250 mg, 0.719 mmol) was alkylated with NaHMDS (1M in THF, 0.86 mL, 0.86 mmol) and 4-(2-bromo-ethoxy)-benzoic acid ethyl ester (216 mg, 0.791 mmol). The reaction temperature was maintained at 50° C. over 24 h. Purification by radial chromatography (hexanes to 4:1 hexanes:EtOAc) provided 4-(2-{2-[3-(tert-butyl-dimethyl-silanyloxy)-4-phenyl-butyl]-5-oxo-pyrrolidin-1-yl}-ethoxy)-benzoic acid ethyl ester (66.4 mg). $^1$H NMR (CDCl$_3$) (selected peaks) δ7.96 (m, 2H), 7.29-7.13 (m, 5H), 6.84 (m, 2H), 4.33 (q, 2H), 4.12 (m, 2H), 3.90 (m, 2H), 3.68 (m, 1H), 3.34 (m, 1H), 2.73 (m, 2H), 2.32 (m, 2H), 1.36 (t, 3H), 0.85 (s, 9H), −0.03 (s, 3H), −0.15 (d, 3H).

Step B: 4-{2-[2-(3-Hydroxy-4-phenyl-butyl)-5-oxo-pyrrolidin-1-yl]-ethoxy}-benzoic acid ethyl ester. Analogous to the procedure described for Example 1A, Step E, 4-(2-{2-[3-(tert-butyl-dimethyl-silanyloxy)-4-phenyl-butyl]-5-oxo-pyrrolidin-1-yl}-ethoxy)-benzoic acid ethyl ester (66.4 mg, 0.122 mmol) was deprotected to provide 4-{2-[2-(3-hydroxy-4-phenyl-butyl)-5-oxo-pyrrolidin-1-yl]-ethoxy}-benzoic acid ethyl ester (52 mg) after purification by radial chromatography (CH$_2$Cl$_2$ to 2% MeOH in CH$_2$Cl$_2$). $^1$H NMR (CDCl$_3$) δ7.94 (m, 2H), 7.31-7.16 (m, 5H), 6.83 (m, 2H), 4.30 (q, 2H), 4.12 (m, 2H), 3.90 (m, 1H), 3.76 (m, 2H), 3.38 (m, 1H), 2.80 (m, 1H), 2.64 (m, 1H), 2.33 (m, 2H), 2.10 (m, 1H), 1.69-1.37 (m, 6H), 1.34 (t, 3H).

Step C: 4-{2-[2-(3-Hydroxy-4-phenyl-butyl)-5-oxo-pyrrolidin-1-yl]-ethoxy}-benzoic acid. Analogous to the procedure described for Example 1A, Step F, 4-{2-[2-(3-hydroxy-4-phenyl-butyl)-5-oxo-pyrrolidin-1-yl]-ethoxy}-benzoic acid ethyl ester (52 mg, 0.122 mmol) was hydrolyzed with 6N NaOH (1 mL) to yield the title compound (41.5 mg). $^1$H NMR (CDCl$_3$) δ7.98 (d, 2H), 7.32-7.16 (m, 5H), 6.85 (m, 2H), 4.13 (m, 2H), 3.92 (m, 1H), 3.81 (m, 1H), 3.75 (m, 1H), 3.40 (m, 1H), 2.82 (m, 1H), 2.66 (m, 1H), 2.36 (m, 2H), 2.10 (m, 2H), 1.70-1.34 (m, 5H); MS 398.4 (M+1), 396.3 (M−1).

EXAMPLE 2A

7-{2S-[3R-Hydroxy-4-(3-methoxymethyl-phenyl)-butyl]-5-oxo-pyrrolidin-1-yl}-heptanoic acid Step A: 7-(2R-Formyl-5-oxo-pyrrolidin-1-yl)-heptanoic acid ethyl ester. To a solution of 7-(2R-hydroxymethyl-5-oxo-pyrrolidin-1-yl)-heptanoic acid ethyl ester (1.63 g, 6.01 mmol) in anhydrous benzene (50 mL) was added 1-(3-dimethylaminopropyl)-3-ethylcarbodiimide hydrochloride (3.46 g, 18.03 mmol) and DMSO (1.5 mL, 24.04 mmol). The solution was cooled to 0° C. and pyridinium trifluoroacetate (1.28 g, 6.61 mmol) was added. The reaction mixture was stirred at 0° C. for 15 minutes and at room temperature for 2 h. The solution was decanted from the oily residue. The residue was washed with benzene (3×) and the combined benzene washes were concentrated in vacuo to provide 7-(2R-formyl-5-oxo-pyrrolidin-1-yl)-heptanoic acid ethyl ester, which was used in Step B without further purification.

Step B: 7-{2R-[4-(3-Methoxymethyl-phenyl)-3-oxo-but-1-enyl]-5-oxo-pyrrolidin-1-yl}-heptanoic acid ethyl ester. To a solution of [3-(3-methoxymethyl-phenyl)-2-oxo-propyl]-phosphonic acid diethyl ester (1.715 g, 5.46 mmol) in THF (43 mL) at 0° C. was added NaH (60% by weight in oil, 240 mg, 6.00 mmol) portionwise. The reaction mixture was stirred at room temperature for 45 minutes. The reaction mixture was cooled to 0° C. and a solution of 7-(2R-formyl-5-oxo-pyrrolidin-1-yl)-heptanoic acid ethyl ester (prepared in Step A, assumed 6.01 mmol) in THF (32 mL) was added dropwise. The reaction mixture was stirred at 0° C. for 15 minutes and at room temperature for 24 h. The reaction mixture was cooled to 0° C. and acetic acid was added until a pH of 5 was achieved. EtOAc and water were added and the aqueous solution was washed with EtOAc (3×). The organic solutions were combined, washed with water, dried (MgSO$_4$), filtered and concentrated. The residue was purified by medium pressure chromatography eluting with a solvent gradient (2:1 hexanes:EtOAc to 1:1 hexanes:EtOAc to 1% MeOH in CH$_2$Cl$_2$ to 3% MeOH in CH$_2$Cl$_2$) to provide 7-{2R-[4-(3-methoxymethyl-phenyl)-3-oxo-but-1-enyl]-5-oxo-pyrrolidin-1-yl}-heptanoic acid ethyl ester (1.4 g). $^1$H NMR (CDCl$_3$) δ7.29 (m, 1H), 7.22 (m, 1H), 7.16 (s, 1H), 7.09 (d, 1H), 6.62 (dd, 1H), 6.19 (d, 1H), 4.41 (s, 2H), 4.10 (m, 3H), 3.82 (s, 2H), 3.51 (m, 1H), 3.36 (s, 3H), 2.67 (m, 1H), 2.43-2.18 (m, 5H), 1.75 (m, 1H), 1.56 (m, 2H), 1.42-1.17 (m, 9H).

Step C: 7-{2R-[3S-Hydroxy-4-(3-methoxymethyl-phenyl)-but-1-enyl]-5-oxo-pyrrolidin-1-yl}-heptanoic acid ethyl ester. To a solution of 7-{2R-[4-(3-methoxymethyl-phenyl)-3-oxo-but-1-enyl]-5-oxo-pyrrolidin-1-yl}-heptanoic acid ethyl ester (1.40 g, 3.26 mmol) in anhydrous CH$_2$Cl$_2$ (200 mL) was added (R)-2-methyl-CBS-oxazaborolidine (1M in toluene, 0.49 mL, 0.49 mmol) and the solution was cooled to −45° C. The reaction mixture was stirred for 20 minutes and catecholborane (1M in THF, 9.8 mL, 9.8 mmol) was added. The reaction mixture was stirred for 24 h at −45° C. and THF (100 mL) and HCl (1N, 100 mL) were added. The reaction mixture was stirred at room temperature for 24 h and at 40–45° C. for 1.5 h. The solution was diluted with CH$_2$Cl$_2$ and water and the layers were separated. The organic solution was cooled to 0° C. and was washed with ice-cold NaOH (0.5N) followed by brine. The organic solution was again washed with ice-cold NaOH (0.5N) followed by brine and was dried (MgSO$_4$), filtered and concentrated. Purification by medium pressure chromatography eluting with a solvent gradient (5:1 hexanes:EtOAc to 2:1 hexanes:EtOAc to 1:1 hexanes:EtOAc to EtOAc to 2% MeOH in CH$_2$Cl$_2$) provided 7-{2R-[3S-hydroxy-4-(3-methoxymethyl-phenyl)-but-1-enyl]-5-oxo-pyrrolidin-1-yl}-heptanoic acid ethyl ester (1.2 g) as an approximate 12:1 mixture of 3S:3R alcohol diastereomers by HPLC analysis. $^1$H NMR (CDCl$_3$) (selected peaks) δ7.26-7.07 (m, 4H), 5.67 (m, 1H), 5.43 (m, 1H), 4.39 (s, 2H), 4.36 (m, 1H), 4.06 (q, 2H), 3.98 (m, 1H), 3.41 (m, 1H), 3.35 (s, 3H); MS 432.3 (M+1), 430.3 (M−1).

Step D: 7-{2S-[3R-Hydroxy-4-(3-methoxymethyl-phenyl)-butyl]-5-oxo-pyrrolidin-1-yl}-heptanoic acid ethyl ester. To a solution of 7-{2R-[3S-hydroxy-4-(3-methoxymethyl-phenyl)-but-1-enyl]-5-oxo-pyrrolidin-1-yl}-heptanoic acid ethyl ester (1.2 g, 2.78 mmol) in EtOH (100 mL) was added 10% palladium on carbon (120 mg). The reaction mixture was hydrogenated on a Parr shaker at 45 psi for 24 h. The catalyst was removed via filtration through Celite® with the aid of EtOH. Purification by medium pressure chromatography eluting with a solvent gradient (CH$_2$Cl$_2$ to 2% MeOH in CH$_2$Cl$_2$ to 5% MeOH in CH$_2$Cl$_2$) (2×) provided 7-{2S-[3R-hydroxy-4-(3-methoxymethyl-phenyl)-butyl]-5-oxo-pyrrolidin-1-yl}-heptanoic acid ethyl ester (1.1 g). $^1$H NMR (CDCl$_3$) δ7.28 (m, 1H), 7.18 (m, 2H), 7.11 (m, 1H), 4.42 (s, 2H), 4.08 (q, 2H), 3.82 (m, 1H), 3.58 (m, 2H), 3.38 (s, 3H), 2.84 (m, 2H), 2.66 (m, 1H), 2.41-2.23 (m, 4H), 2.08 (m, 1H), 1.78 (m, 1H), 1.64-1.37 (m, 9H), 1.28 (m, 4H), 1.22 (t, 3H).

Step E: 7-{2S-[3R-Hydroxy-4-(3-methoxymethyl-phenyl)-butyl]-5-oxo-pyrrolidin-1-yl}-heptanoic acid. To a solution of 7-{2S-[3R-hydroxy-4-(3-methoxymethyl-phenyl)-butyl]-5-oxo-pyrrolidin-1-yl}-heptanoic acid ethyl ester (1.1 g, 2.53 mmol) in EtOH (32 mL) was added NaOH (6N, 16 mL). The reaction mixture was stirred for 24 h and 1N HCl was added to obtain a pH of about 2. Brine and CH$_2$Cl$_2$ were added and the layers were separated. The aqueous solution was washed with 5% MeOH in CH$_2$Cl$_2$ (2 times). The combined organic layers were dried (MgSO$_4$), filtered and concentrated to provide the title compound of Example 2A (990 mg). $^1$H NMR (CDCl$_3$) δ7.28 (m, 1H), 7.18 (m, 2H), 7.11 (m, 1H), 4.43 (s, 2H), 3.83 (m, 1H), 3.57 (m, 2H), 3.40 (s, 3H), 2.91 (m, 1H), 2.79 (m, 1H), 2.66 (m, 1H), 2.43-2.25 (m, 4H), 2.10 (m, 1H), 1.83 (m, 1H), 1.66-1.22 (m, 13H); MS 406.3 (M+1), 404.3 (M−1).

EXAMPLE 2B

7-[2R-(3-Hydroxy-4-naphthalen-2-yl-butyl)-5-oxo-pyrrolidin-1-yl]-heptanoic acid

Step A: 7-[2R-(4-Naphthalen-2-yl-3-oxo-but-1-enyl)-5-oxo-pyrrolidin-1-yl]-heptanoic acid ethyl ester. Analogous to the procedure described for Example 2A, Step B, the anion derived from (3-naphthalen-2-yl-2-oxo-propyl)-phosphonic acid dimethyl ester (646 mg, 2.21 mmol) and NaH (60% by weight in oil, 81 mg, 2.02 mmol) was reacted with 7-(2R-formyl-5-oxo-pyrrolidin-1-yl)-heptanoic acid ethyl ester (assumed 1.84 mmol) over 163 h. Purification by medium pressure chromatography (1:1 hexanes:EtOAc to EtOAc) provided 7-[2R-(4-naphthalen-2-yl-3-oxo-but-1-enyl)-5-oxo-pyrrolidin-1-yl]-heptanoic acid ethyl ester (340 mg). $^1$H NMR (CDCl$_3$) δ7.78 (m, 3H), 7.65 (s, 1H), 7.46 (m, 2H), 7.30 (d, 1H), 6.66 (dd, 1H), 6.24 (d, 1H), 4.10 (m, 3H), 3.99 (s, 2H), 3.45 (m, 1H), 2.63 (m, 1H), 2.44-2.18 (m, 5H), 1.75 (m, 1H), 1.52 (m, 2H), 1.37-1.06 (m, 9H); MS 436.1 (M+1), 434.1 (M−1).

Step B: 7-[2S-(4-Naphthalen-2-yl-3-oxo-butyl)-5-oxo-pyrrolidin-1-yl]-heptanoic acid ethyl ester. Analogous to the procedure described for Example 2A, Step D, a mixture of 7-[2R-(4-naphthalen-2-yl-3-oxo-but-1-enyl)-5-oxo-pyrrolidin-1-yl]-heptanoic acid ethyl ester (337 mg, 0.774 mmol) and 10% palladium on carbon (50 mg) in EtOH (50 mL) was hydrogenated at 50 psi for 3 h. Medium pressure chromatography (1:1 hexanes: EtOAc to EtOAc) provided 7-[2S-(4-naphthalen-2-yl-3-oxo-butyl)-5-oxo-pyrrolidin-1-yl]-heptanoic acid ethyl ester (290 mg). $^1$H NMR (CDCl$_3$) δ7.80 (m, 3H), 7.66 (s, 1H), 7.47 (m, 2H), 7.30 (m, 1H), 4.10 (q, 2H), 3.85 (s, 2H), 3.52 (m, 2H), 2.77 (m, 1H), 2.47 (m, 2H), 2.26 (m, 4H), 1.98 (m, 2H), 1.61-1.16 (m, 13H); MS 438.1 (M+1), 436.1 (M−1).

Step C: 7-[2S-(3-Hydroxy-4-naphthalen-2-yl-butyl)-5-oxo-pyrrolidin-1-yl]-heptanoic acid ethyl ester. To a solution of 7-[2S-(4-naphthalen-2-yl-3-oxo-butyl)-5-oxo-pyrrolidin-1-yl]-heptanoic acid ethyl ester (367 mg, 0.839 mmol) in EtOH (20 mL) was added NaBH$_4$ (32 mg, 0.839 mmol). The reaction mixture was stirred for 2 h and water (5 mL) was added. The volatiles were removed in vacuo and the remaining aqueous solution was washed with CHCl$_3$ (4×10 mL). The organic solutions were combined, dried (MgSO$_4$), filtered and concentrated. Purification by medium pressure chromatography (1:1 hexanes:EtOAc to EtOAc) provided 7-[2S-(3-hydroxy-4-naphthalen-2-yl-butyl)-5-oxo-pyrrolidin-1-yl]-heptanoic acid ethyl ester (332 mg). $^1$H NMR (CDCl$_3$) δ7.80 (m, 3H), 7.65 (s, 1H), 7.46 (m, 2H), 7.33 (m, 1H), 4.07 (m, 2H), 3.91 (m, 1H), 3.60 (m, 2H), 2.98 (m, 1H), 2.84 (m, 2H), 2.35 (m, 2H), 2.25 (t, 2H), 2.10 (m, 1H), 2.01 (m, 1H), 1.81 (m, 1H), 1.70 (d, 1H), 1.68-1.37 (m, 7H), 1.36-1.20 (m, 7H); MS 440.1 (M+1).

Step D: 7-[2S-(3-Hydroxy-4-naphthalen-2-yl-butyl)-5-oxo-pyrrolidin-1-yl]-heptanoic acid. A solution of 7-[2S-(3-hydroxy-4-naphthalen-2-yl-butyl)-5-oxo-pyrrolidin-1-yl]-heptanoic acid ethyl ester (327 mg, 0.744 mmol), NaOH (1M, 0.8 mL), and MeOH (15 mL) was heated under reflux for 4 h. The volatiles were removed in vacuo and water (15 mL) was added. The aqueous solution was acidified to a pH of 5 with 1N HCl and the acidic solution was washed with CHCl$_3$ (4×10 mL). The organic solutions were combined, dried (MgSO$_4$), filtered and concentrated to provide 7-[2S-(3-hydroxy-4-naphthalen-2-yl-butyl)-5-oxo-pyrrolidin-1-yl]-heptanoic acid (180 mg). $^1$H NMR (CDCl$_3$) δ7.80 (m, 3H), 7.65 (s, 1H), 7.46 (m, 2H), 7.33 (m, 1H), 3.94 (m, 1H), 3.58 (m, 2H), 3.02-2.80 (m, 3H), 2.34 (m, 4H), 2.08 (m, 2H), 1.67-1.23 (m, 13H); MS 412.1 (M+1), 410.2 (M−1).

Step E: Sodium salt of 7-[2S-(3-hydroxy-4-naphthalen-2-yl-butyl)-5-oxo-pyrrolidin-1-yl]-heptanoic acid. To a solution of 7-[2S-(3-hydroxy-4-naphthalen-2-yl-butyl)-5-oxo-pyrrolidin-1-yl]-heptanoic acid (35 mg, 0.0851 mmol) in MeOH (5 mL) at 0° C. was added NaOH (1M, 0.085 mL). The reaction mixture was stirred for 1.5 h at 0° C. and was concentrated in vacuo, azeotroping with CHCl$_3$ (3×5 mL) to yield the sodium salt of the title compound of Example 2B (37 mg). $^1$H NMR (CDCl$_3$) δ7.69-7.24 (m, 7H), 3.78 (m, 1H), 3.40 (m, 2H), 2.80 (m, 6H), 2.16-1.70 (m, 4H), 1.43-1.18 (m, 12H).

EXAMPLE 2C

7-[2R-(4-Benzo[1,3]dioxol-5-yl-3-hydroxy-but-1-enyl)-5-oxo-pyrrolidin-1-yl]-heptanoic acid Step A: 7-[2R-(4-Benzo[1,3]dioxol-5-yl-3-oxo-but-1-enyl)-5-oxo-Pyrrolidin-1-yl]-heptanoic acid ethyl ester. Analogous to the procedure described for Example 2A, Step B, the anion generated from (3-benzo[1,3]dioxol-5-yl-2-oxo-propyl)-phosphonic acid dimethyl ester (12.65 g, 44.2 mmol) and NaH (60% by weight in oil, 1.62 g, 40.5 mmol) was reacted with 7-(2R-formyl-5-oxo-pyrrolidin-1-yl)-heptanoic acid ethyl ester (assumed 36.8 mmol) over 24 h. Purification by medium pressure chromatography (10% EtOAc in hexanes to 40% EtOAc in hexanes) provided 7-[2R-(4-benzo[1,3]dioxol-5-yl-3-oxo-but-1-enyl)-5-oxo-pyrrolidin-1-yl]-heptanoic acid ethyl ester (4.18 g). $^1$H NMR (CDCl$_3$) δ6.76 (d, 1H), 6.63 (m, 3H), 6.20 (d, 1H), 5.94 (s, 2H), 4.13 (m, 3H), 3.74 (s, 2H), 3.52 (m, 1H), 2.71 (m, 1H), 2.38 (m, 2H), 2.26 (m, 3H), 1.78 (m, 1H), 1.58 (m, 5H), 1.46-1.19 (m, 6H).

Step B: 7-[2R-(4-Benzo[1,31]dioxol-5-yl-3-hydroxy-but-1-enyl)-5-oxo-pyrrolidin-1-yl]-heptanoic acid ethyl ester. Analogous to the procedure described for Example 2B, Step C, 7-[2R-(4-benzo[1,3]dioxol-5-yl-3-oxo-but-1 -enyl)-5-oxo-pyrrolidin-1-yl]-heptanoic acid ethyl ester (4.18 g, 9.74 mmol) was reacted with NaBH$_4$ (369 mg, 9.74 mmol) in EtOH (32 mL). The NaBH$_4$ addition was performed at 0° C. and the reaction mixture was stirred at room temperature for 3 h. Purification by medium pressure chromatography (EtOAc) provided 7-[2R-(4-benzo[1,3]dioxol-5-yl-3-hydroxy-but-1-enyl)-5-oxo-pyrrolidin-1-yl]-heptanoic acid ethyl ester (3.36 g).

Step C: 7-[2R-(4-Benzo[1,3]dioxol-5-yl-3-hydroxy-but-1-enyl)-5-oxo-pyrrolidin-1-yl]-heptanoic acid. Analogous to the procedure described for Example 2A, Step E, 7-[2R-(4-benzo[1,3]dioxol-5-yl-3-hydroxy-but-1-enyl)-5-oxo-pyrrolidin-1-yl]-heptanoic acid ethyl ester (3.36 g, 7.79 mmol) was hydrolyzed with 2N NaOH (11 mL) in MeOH. Purification by medium pressure chromatography (50% EtOAc in hexanes to EtOAc to 5% MeOH in CH$_2$Cl$_2$) followed by a second column eluting with a solvent gradient (1% MeOH to CH$_2$Cl$_2$ to 5% MeOH in CH$_2$Cl$_2$) provided 7-[2R-(4-benzo[1,3]dioxol-5-yl-3-hydroxy-but-1-enyl)-5-oxo-pyrrolidin-1-yl]-heptanoic acid (2.26 g). $^1$H NMR (CDCl₃) δ6.66 (m, 3H), 5.91 (s, 2H), 5.69 (m, 1H), 5.44 (m, 1H), 4.31 (m, 1H), 4.01 (m, 1H), 3.45 (m, 1H), 2.76 (m, 3H), 2.34 (m, 4H), 2.15 (m, 1H), 1.70-1.20 (m, 10H); MS 404.3 (M+1), 402.1 (M−1).

Step D: Sodium salt of 7-[2R-(4-Benzo[1,3]dioxol-5-yl-3-hydroxy-but-1-enyl)-5-oxo-pyrrolidin-1-yl]-heptanoic acid. The sodium salt was prepared by addition of NaHCO₃ (470 mg, 5.60 mmol) in water to a solution of 7-[2R-(4-benzo[1,3]dioxol-5-yl-3-hydroxy-but-1-enyl)-5-oxo-pyrrolidin-1-yl]-heptanoic acid (2.26 g, 5.60 mmol) in EtOH. The reaction mixture was stirred for 3 h and was concentrated in vacuo to provide the sodium salt of the title compound of Example 2C. ¹H NMR (CD₃OD) δ6.65 (m, 3H), 5.85 (s, 2H), 5.67 (m, 1H), 5.34 (m, 1H), 4.24 (m, 1H), 4.09 (m, 1H), 3.45 (m, 1H), 2.79 (m, 2H), 2.61 (m, 2H), 2.29 (m, 2H), 2.16 (m, 3H), 1.68-1.17 (m, 9H).

EXAMPLE 2D

7-[2S-(4-Benzo[1,3]dioxol-5-yl-3-hydroxy-butyl)-5-oxo-pyrrolidin-1-yl]-heptanoic acid Step A: 7-[2S-(4-Benzo[1,3]dioxol-5-yl-3-hydroxy-butyl)-5-oxo-pyrrolidin-1-yl]-heptanoic acid. Analogous to the procedure described for Example 2A, Step D, a mixture of 7-[2R-(4-benzo[1,3]dioxol-5-yl-3-hydroxy-but-1-enyl)-5-oxo-pyrrolidin-1-yl]-heptanoic acid (120 mg, 2.96 mmol), MeOH (30 mL), and 10% palladium on carbon (14 mg) was hydrogenated at 50 psi for 18 h to provide 7-[2S-(4-benzo[1,3]dioxol-5-yl-3-hydroxy-butyl)-5-oxo-pyrrolidin-1-yl]-heptanoic acid (71.3 mg). ¹H NMR (CDCl₃) δ6.68 (m, 3H), 5.92 (s, 2H), 3.74 (m, 1H), 3.57 (m, 2H), 2.87 (m, 1H), 2.72 (m, 1H), 2.54 (m, 1H), 2.31 (m, 4H), 2.10 (m, 1H), 1.99 (m, 1H), 1.66-1.19 (m, 13H); MS 406.3 (M+1), 404.3 (M−1).

EXAMPLE 2E

4-{3-[2R-(4-Benzo[1,3]dioxol-5-yl-3-hydroxy-but-1-enyl)-5-oxo-pyrrolidin-1-yl]-propyl}-benzoic acid Step A: 4-{3-[2R-(4-Benzo[1,3]dioxol-5-yl-3-oxo-but-1-enyl)-5-oxo-pyrrolidin-1-yl]-propyl}-benzoic acid methyl ester. Analogous to the procedure described for Example 2A, Step B, the anion derived from (3-benzo[1,3]dioxol-5-yl-2-oxo-propyl)-phosphonic acid dimethyl ester (356 mg, 1.28 mmol) and NaH (60% in oil, 46 mg, 1.14 mmol) was reacted with 4-[3-(2R-formyl-5-oxo-pyrrolidin-1-yl)-propyl]-benzoic acid methyl ester (assumed 1.04 mmol) over 24 h. Purification by medium pressure chromatography (30% hexane in EtOAc to EtOAc) provided 4-{3-[2R-(4-benzo[1,3]dioxol-5-yl-3-oxo-but-1-enyl)-5-oxo-pyrrolidin-1-yl]-propyl}-benzoic acid methyl ester (202 mg). ¹H NMR (CDCl₃) δ7.92 (d, 2H), 7.18 (d, 2H), 6.73 (d, 1H), 6.60 (m, 3H), 6.15 (d, 1H), 5.91 (s, 2H), 4.08 (m, 1H), 3.87 (s, 3H), 3.68 (s, 2H), 3.56 (m, 1H), 2.79 (m, 1H), 2.59 (t, 2H), 2.34 (m, 2H), 2.14 (m, 1H), 1.72 (m, 3H); MS 450.1 (M+1).

Step B: 4-{3-[2R-(4-Benzo[1,3]dioxol-5-yl-3-hydroxy-but-1-enyl)-5-oxo-pyrrolidin-1-yl]-propyl}-benzoic acid methyl ester. Analogous to the procedure described for Example 2B, Step C, 4-{3-[2R-(4-benzo[1,3]dioxol-5-yl-3-oxo-but-1-enyl)-5-oxo-pyrrolidin-1-yl]-propyl}-benzoic acid methyl ester (202 mg, 0.449 mmol) was reacted with NaBH₄ (17 mg, 0.45 mmol) in MeOH (8 mL) at 0° C. over 2 h. Purification by medium pressure chromatography (EtOAc to 2% MeOH in CH₂Cl₂) provided 4-{3-[2R-(4-benzo[1,3]dioxol-5-yl-3-hydroxy-but-1-enyl)-5-oxo-pyrrolidin-1-yl]-propyl}benzoic acid methyl ester (156 mg). ¹H NMR (CDCl₃) δ7.94 (d, 2H), 7.23 (d, 2H), 6.67 (m, 3H), 5.92 (s, 2H), 5.66 (m, 1H), 5.45 (m, 1H), 4.28 (m, 1H), 3.99 (m, 1H), 3.87 (s, 3H), 3.55 (m, 1H), 2.88-2.59 (m, 5H), 2.50-1.61 (m, 7H); MS 452.1 (M+1).

Step C: 4-{3-[2R-(4-Benzo[1,3]dioxol-5-yl-3-hydroxy-but-1-enyl)-5-oxo-pyrrolidin-1-yl]-propyl}-benzoic acid. Analogous to the procedure described for Example 2A, Step E, 4-{3-[2R-(4-benzo[1,3]dioxol-5-yl-3-hydroxy-but-1-enyl)-5-oxo-pyrrolidin-1-yl]-propyl}-benzoic acid methyl ester (156 mg, 0.345 mmol) was hydrolyzed with 2N NaOH in MeOH (5 mL) to provide the title compound of Example 2E (120 mg). ¹H NMR (CDCl₃) δ7.99 (d, 2H), 7.26 (m, 2H), 6.74 (d, 1H), 6.63 (m, 2H), 5.91 (s, 2H), 5.67 (m 1H), 5.46 (m, 1H), 4.29 (m, 1H), 3.99 (m, 1H), 3.57 (m, 1H), 2.94-2.60 (m, 5H), 2.36 (m, 2H), 2.14 (m, 1H), 1.87-1.62 (m, 4H); MS 436.2 (M−1).

EXAMPLE 2F

4-{3-[2S-(4-Benzo[1,3]dioxol-5-yl-3-hydroxy-butyl)-5-oxo-pyrrolidin-1-yl]-propyl}-benzoic acid Step A: 4-{3-[2S-(4-Benzo[1,3]dioxol-5-yl-3-hydroxy-butyl)-5-oxo-pyrrolidin-1-yl]-propyl}-benzoic acid. Analogous to the procedure described for Example 2A, Step D, 4-{3-[2R-(4-benzo[1,3]dioxol-5-yl-3-hydroxy-but-1-enyl)-5-oxo-pyrrolidin-1-yl]-propyl}-benzoic acid (116 mg, 0.265 mmol) was hydrogenated to provide 4-{3-[2S-(4-benzo[1,3]dioxol-5-yl-3-hydroxy-butyl)-5-oxo-pyrrolidin-1-yl]-propyl}-benzoic acid (101 mg). ¹H NMR (CDCl₃) δ7.99 (d, 2H), 7.26 (m, 2H), 6.74 (d, 1H), 6.63 (m, 2H), 5.91 (s, 2H), 5.68 (m, 1H), 5.46 (m, 1H), 4.29 (m, 1H), 3.99 (m, 1H), 3.56 (m, 1h), 2.91 (m, 4H), 2.84-2.60 (m, 4H), 2.36 (m, 2H), 2.14 (m, 1H), 1.87-1.62 (m, 4H); MS 438.2 (M−1).

EXAMPLE 2G

7-{2S-[3R-Hydroxy-4-(3-trifluoromethoxy-phenyl)-butyl]-5-oxo-pyrrolidin-1-yl}-heptanoic acid Step A: 7-{2-Oxo-5R-[3-oxo-4-(3-trifluoromethoxy-phenyl)-but-1-enyl]-pyrrolidin-1-yl}-heptanoic acid ethyl ester. Analogous to the procedure described for Example 2A, Step B, the anion derived from [2-oxo-3-(3-trifluoromethoxy-phenyl)-propyl]-phosphonic acid dimethyl ester (370 mg, 1.13 mmol) and NaH (60% in oil, 45 mg, 1.13 mmol) was reacted with 7-(2R-formyl-5-oxo-pyrrolidin-1-yl)-heptanoic acid ethyl ester (assumed 1.13 mmol) over 16 h. Medium pressure chromatography (19:1 hexanes:EtOAc to 6:4 hexanes:EtOAc to 1:1 hexanes:EtOAc to EtOAc) provided 7-{2-oxo-5R-[3-oxo-4-(3-trifluoromethoxy-phenyl)-but-1-enyl]-pyrrolidin-1-yl}-heptanoic acid ethyl ester (132 mg). ¹H NMR (CDCl₃) δ7.35 (m, 1H), 7.12 (m, 2H), 7.05 (s, 1H), 6.66 (dd, 1H), 6.21 (d, 1H), 4.18 (m, 1H), 4.10 (q, 2H), 3.86 (s, 2H), 3.54 (m, 1H), 2.70 (m, 1H), 2.47-2.22 (m, 5H), 1.78 (m, 1H), 1.57 (m, 2H), 1.61-1.21 (m, 9H); MS 470.2 (M+1), 468.1 (M−1).

Step B: 7-{2R-[3S-Hydroxy-4-(3-trifluoromethoxy-phenyl)-but-1-enyl]-5-oxo-pyrrolidin-1-yl}-heptanoic acid ethyl ester. To a solution of 7-{2-oxo-5R-[3-oxo-4-(3-trifluoromethoxy-phenyl)-but-1-enyl]-pyrrolidin-1-yl}-heptanoic acid ethyl ester (169 mg, 0.360 mmol) and (R)-2-methyl-CBS-oxazaborolidine (1M in toluene, 0.054 mL, 0.054 mmol) in CH₂Cl₂ (25.0 mL) at −45° C. was added catecholborane (1M in THF, 1.08 mL, 1.08 mmol) dropwise. The reaction mixture was stirred at −45° C. for 19 h. methanol (5 mL) was added and the reaction mixture was warmed to room temperature and was concentrated in vacuo. The residue was dissolved in CHCl₃ and the organic solution was washed with 1M NaOH (4×10 mL), 1M HCl (1×10 mL), and water (1×10 mL). The organic solution was dried (MgSO$_4$), filtered and concentrated. Purification by medium pressure chromatography (9:1 hexanes:EtOAc to 1:1 hexanes:EtOAc to EtOAc) provided 7-{2R-[3S-hydroxy-4-(3-trifluoromethoxy-phenyl)-but-1-enyl]-5-oxo-pyrrolidin-1-yl}-heptanoic acid ethyl ester (90 mg) as a 9:1 mixture (3S:3R) of alcohol diastereomers by HPLC analysis. $^1$H NMR (CDCl$_3$) δ7.32 (m, 1H), 7.10 (m, 3H), 5.70 (dd, 1H), 5.50 (dd, 1H), 4.41 (m, 1H), 4.09 (q, 2H), 4.01 (m, 1H), 3.45 (m, 1H), 2.85 (d, 2H), 2.70 (m, 1H), 2.41-2.24 (m, 4H), 2.17 (m, 1H), 1.71-1.54 (m, 5H), 1.47-1.21 (m, 8H); MS 472.3 (M+1), 470.2 (M−1).

Step C: 7-{2S-[3R-Hydroxy-4-(3-trifluoromethoxy-phenyl)-butyl]-5-oxo-pyrrolidin-1-yl}-heptanoic acid ethyl ester. Analogous to the procedure described for Example 2A, Step D, a solution of 7-{2R-[3S-hydroxy-4-(3-trifluoromethoxy-phenyl)-but-1-enyl]-5-oxo-pyrrolidin-1-yl}-heptanoic acid ethyl ester (86 mg, 0.182 mmol) in EtOH (40 mL) was hydrogenated in the presence of 10% palladium on carbon (50 mg) at 50 psi for 2.5 h. Purification by medium pressure chromatography (9:1 hexanes:EtOAc to 1:1 hexanes:EtOAc to EtOAc) provided 7-{2S-[3R-hydroxy-4-(3-trifluoromethoxy-phenyl)-butyl]-5-oxo-pyrrolidin-1-yl}-heptanoic acid ethyl ester (49 mg). $^1$H NMR (CDCl3) δ7.33 (m, 1H), 7.11 (m, 3H), 4.09 (q, 2H), 3.84 (m, 1H), 3.59 (m, 2H), 2.85 (m, 2H), 2.72 (m, 1H), 2.42-2.24 (m, 4H), 2.10 (m, 1H), 1.79 (m, 1H), 1.68-1.21 (m, 16H); MS 474.2 (M+1).

Step D: 7-{2S-[3R-Hydroxy-4-(3-trifluoromethoxy-phenyl)-butyl]-5-oxo-pyrrolidin-1-yl}-heptanoic acid. Analogous to the procedure described for Example 2A, Step E, 7-{2S-[3R-hydroxy-4-(3-trifluoromethoxy-phenyl)-butyl]-5-oxo-pyrrolidin-1-yl}-heptanoic acid ethyl ester (45 mg, 0.095 mmol) was hydrolyzed with 1M NaOH (0.95 mL) in MeOH (20 mL) under reflux over 4 h to provide the title compound of Example 2G (35 mg). $^1$H NMR (CDCl$_3$) δ7.33 (m, 1H), 7.10 (m, 3H), 3.86 (m, 1H), 3.58 (m, 2H), 2.90 (m, 1H), 2.81 (m, 1H), 2.73 (m, 1H), 2.34 (m, 4H), 2.10 (m, 1H), 1.80 (m, 1H), 1.66-1.24 (m, 13H); MS 446.3 (M+1), 444.2 (M−1).

EXAMPLE 2H

7-{2S-[4-(3-Cyano-phenyl)-3R-hydroxy-butyl]-5-oxo-pyrrolidin-1-yl}-heptanoic acid Step A: 7-{2R-[4-(3-Bromo-phenyl)-3-oxo-but-1-enyl]-5-oxo-pyrrolidin-1-yl}-heptanoic acid ethyl ester. Analogous to the procedure described for Example 2A, Step B, the anion derived from [3-(3-bromo-phenyl)-2-oxo-propyl]-phosphonic acid dimethyl ester (2.90 g, 9.03 mmol) and NaH (60% in oil, 489 mg, 12.23 mmol) was reacted with 7-(2R-formyl-5-oxo-pyrrolidin-1-yl)-heptanoic acid ethyl ester (assumed 11.06 mmol) over 24 h. Flash chromatography (EtOAc to 5% MeOH in EtOAc) provided 7-{2R-[4-(3-bromo-phenyl)-3-oxo-but-1-enyl]-5-oxo-pyrrolidin-1-yl}-heptanoic acid ethyl ester (2.63 g). $^1$H NMR (CDCl$_3$) δ7.40 (d, 1H), 7.35 (s, 1H), 7.20 (m, 1H), 7.12 (d, 1H), 6.66 (dd, 1H), 6.21 (d, 1H), 4.17 (m, 1H), 4.11 (q, 2H), 3.81 (s, 2H), 3.54 (m, 1H), 2.71 (m, 1H), 2.48-2.21 (m, 5H), 1.79 (m, 1H), 1.58 (m, 2H), 1.47-1.20 (m, 9H); MS 466.1 (M+1).

Step B: 7-{2R-[4-(3-Bromo-phenyl)-3S-hydroxy-but-1-enyl]-5-oxo-pyrrolidin-1-yl}-heptanoic acid ethyl ester. To a solution of 7-{2R-[4-(3-bromo-phenyl)-3-oxo-but-1-enyl]-5-oxo-pyrrolidin-1-yl}-heptanoic acid ethyl ester (2.63 g, 5.66 mmol) and (R)-2-methyl-CBS-oxazaborolidine (1M in toluene, 0.85 mL, 0.85 mmol) in CH$_2$Cl$_2$ (225 mL) at −45° C. was added catecholborane (1M in THF, 17.0 mL, 17.0 mmol) dropwise. The reaction mixture was stirred at −45° C. for 17 h. Aqueous HCl (1N, 17 mL) was added and the reaction mixture was warmed to room temperature. The organic solution was washed consecutively with 1N HCl (1×100 mL), water (2×100 mL) and brine (1×100 mL). The organic solution was dried (MgSO$_4$), filtered and concentrated. Purification by flash chromatography (EtOAc to 5% MeOH in EtOAc) provided 7-{2R-[4-(3-bromo-phenyl)-3S-hydroxy-but-1-enyl]-5-oxo-pyrrolidin-1-yl}-heptanoic acid ethyl ester (705 mg) as an approximate 95:5 ratio of 3S:3R alcohol diastereomers by $^1$H NMR. $^1$H NMR (CDCl$_3$) δ7.36 (m, 2H), 7.15 (m, 2H), 5.70 (dd, 1H), 5.48 (dd, 1H), 4.40 (m, 1H), 4.10 (q, 2H), 4.03 (m, 1H), 3.46 (m, 1H), 2.81 (d, 2H), 2.72 (m, 1H), 2.39 (m, 2H), 2.27 (t, 2H), 2.20 (m, 1H), 1.84-1.22 (m, 13H).

Step C: 7-{2R-[4-(3-Cyano-phenyl)-3S-hydroxy-but-1-enyl]-5-oxo-pyrrolidin-1-yl}-heptanoic acid ethyl ester. Nitrogen was bubbled into a solution of 7-{2R-[4-(3-bromo-phenyl)-3S-hydroxy-but-1-enyl]-5-oxo-pyrrolidin-1-yl}-heptanoic acid ethyl ester (700 mg, 1.50 mmol) in DMF (2.6 mL) for 5 minutes. Zinc cyanide (108 mg, 0.92 mmol) and tetrakis(triphenylphosphine)palladium(0) (58 mg, 0.05 mmol) were added and nitrogen was bubbled into the reaction mixture for 5 minutes. The reaction mixture was heated at 105° C. for 24 h. Additional tetrakis(triphenylphosphine)palladium(0) (58 mg, 0.050 mmol) was added and heating was continued for 1.5 h. The reaction mixture was poured into water (50 mL) and the aqueous solution was washed with Et$_2$O (3×50 mL). The combined ethereal layers were dried (MgSO$_4$), filtered and concentrated in vacuo. Medium pressure chromatography (EtOAc to 5% MeOH in EtOAc to 10% MeOH in EtOAc) provided 7-{2R-[4-(3-cyano-phenyl)-3S-hydroxy-but-1-enyl]-5-oxo-pyrrolidin-1-yl}-heptanoic acid ethyl ester (323 mg). $^1$H NMR (CDCl$_3$) δ7.53 (m, 2H), 7.48-7.39 (m, 2H), 5.72 (dd, 1H), 5.51 (dd, 1H), 4.41 (m, 1H), 4.10 (q, 2H), 4.03 (m, 1H), 3.46 (m, 1H), 2.86 (m, 2H), 2.73 (m, 1H), 2.36 (m, 2H), 2,27 (t, 2H), 2.20 (m, 1H), 1.71-1.22 (m, 13H); MS 413.3 (M+1).

Step D: 7-{2S-[4-(3-Cyano-phenyl)-3R-hydroxy-butyl]-5-oxo-pyrrolidin-1-yl}-heptanoic acid ethyl ester. Analogous to the procedure described for Example 2A, Step D, a solution of 7-{2R-[4-(3-cyano-phenyl)-3S-hydroxy-but-1-enyl]-5-oxo-pyrrolidin-1-yl}-heptanoic acid ethyl ester (150 mg, 0.36 mmol) in EtOH (13 mL) was hydrogenated in the presence of 10% palladium on carbon (16 mg) at 45 psi for 3.5 h to provide 7-{2S-[4-(3-cyano-phenyl)-3R-hydroxy-butyl]-5-oxo-pyrrolidin-1-yl}-heptanoic acid ethyl ester (150 mg). $^1$H NMR (CDCl$_3$) δ7.54 (m, 2H), 7.44 (m, 2H), 4.09 (q,2H), 3.84 (m, 1H), 3.60 (m, 2H), 2.95-2.71 (m, 3H), 2.36 (m, 2H), 2.27 (t, 2H), 2.11 (m, 1H), 1.79 (m, 1H), 1.68-1.20 (m, 16H); MS 415.2 (M+1).

Step E: 7-{2S-[4-(3-Cyano-phenyl)-3R-hydroxy-butyl]-5-oxo-pyrrolidin-1-yl}-heptanoic acid. Analogous to the procedure described for Example 2A, Step E, 7-{2S-[4-(3-cyano-phenyl)-3R-hydroxy-butyl]-5-oxo-pyrrolidin-1-yl}-heptanoic acid ethyl ester (150 mg, 0.36 mmol) was hydrolyzed with 5M NaOH (3 mL) in EtOH (5 mL) at room temperature over 24 h to provide the title compound of Example 2H (119 mg).1H NMR (CDCl$_3$) δ7.52 (m, 2H), 7.43 (m, 2H), 3.84 (m, 1H), 3.56 (m, 2H), 2.93-2.70 (m, 3H), 2.32 (m, 4H), 2.09 (m, 1H), 1.78 (m, 1H), 1.65-1.21 (m, 13H); MS 387.2 (M+1).

EXAMPLE 2I 7-(2S-{3R-Hydroxy-4-[3-(2-methoxy-ethyl)-phenyl]-butyl}-5-oxo-pyrrolidin-1-yl)-heptanoic acid Step A: 7-(2R-{4-[3-(2-Methoxy-ethyl)-phenyl]-3-oxo-but-1-enyl}-5-oxo-pyrrolidin-1yl)-heptanoic acid ethyl ester. Analogous to the procedure described for Example 2A, Step B, the anion derived from {3-[3-(2-methoxy-ethyl)-phenyl]-2-oxo-propyl}-phosphonic acid diethyl ester (130 mg, 0.396 mmol) and NaH (60% in oil, 17 mg, 0.425 mmol) was reacted with 7-(2R-formyl-5-oxo-pyrrolidin-1-yl)-heptanoic acid ethyl ester (assumed 0.461 mmol) over 24 h. Medium pressure chromatography (50% EtOAc in hexanes to EtOAc) provided 7-(2R-{4-[3-(2-methoxy-ethyl)-phenyl]-3-oxo-but-1-enyl}-5-oxo-pyrrolidin-1-yl)-heptanoic acid ethyl ester (101 mg). $^1$H NMR (CDCl$_3$) δ7.23 (m, 1H), 7.11 (m, 1H), 7.02 (m, 2H), 6.62 (dd, 1H), 6.20 (d, 1H), 4.12 (m, 3H), 3.80 (s, 2H), 3.56 (t, 2H), 3.51 (m, 1H), 3.32 (s, 3H), 2.84 (t, 2H), 2.68 (m, 1H), 2.37 (m, 2H), 2.24 (m, 3H), 1.75 (m, 1H), 1.56 (m, 2H), 1.42-1.17 (m, 9H); MS 444.2 (M+1).

Step B: 7-(2R-{3S-Hydroxy-4-[3-(2-methoxy-ethyl)-phenyl]-but-1-enyl}-5-oxo-pyrrolidin-1-yl)-heptanoic acid ethyl ester. To a solution of 7-(2R-{4-[3-(2-methoxy-ethyl)-phenyl]-3-oxo-but-1-enyl}-5-oxo-pyrrolidin-1-yl)-heptanoic acid ethyl ester (88 mg, 0.198 mmol) and (R)-2-methyl-CBS-oxazaborolidine (1M in toluene, 0.200 mL, 0.200 mmol) in CH$_2$Cl$_2$ (10 mL) at −45° C. was added catecholborane (1M in THF, 0.60 mL, 0.60 mmol) dropwise. The reaction mixture was stirred at −45° C. for 24 h. Aqueous HCl (1N, 10 mL) was added and the reaction mixture was warmed to room temperature and was stirred for 1.5 h. The organic solution was washed with cold 1N NaOH (3×15 mL) followed by brine (1×20 mL). The organic solution was dried (MgSO$_4$), filtered and concentrated. Purification by medium pressure chromatography (50% EtOAc in hexanes to 75% EtOAc in hexanes to EtOAc) provided 7-(2R-{3S-hydroxy-4-[3-(2-methoxy-ethyl)-phenyl]-but-1-enyl}-5-oxo-pyrrolidin-1-yl)-heptanoic acid ethyl ester (45 mg) as an approximate 4:1 mixture of 3S:3R alcohol diasteromers by $^1$H NMR. $^1$H NMR (CDCl$_3$) δ7.22 (m, 1H), 7.09 (m, 1H), 7.04 (m, 2H), 5.72 (dd, 1H), 5.49 (dd, 1H), 4.38 (m, 1H), 4.10 (q, 2H), 4.02 (m, 1H), 3.58 (t, 2H), 3.46 (m, 1H), 3.34 (s, 3H), 2.87-2.68 (m, 5H), 2.41-2.24 (m, 4H), 2.18 (m, 1H), 1.70 (m, 2H), 1.59 (m, 2H), 1.48-1.21 (m, 9H); MS 446.4 (M+1).

Step C: 7-(2S-{3R-Hydroxy-4-[3-(2-methoxy-ethyl)-phenyl]-butyl}-5-oxo-pyrrolidin-1-yl)-heptanoic acid ethyl ester. Analogous to the procedure described for Example 2A, Step D, a solution of 7-(2R-{3S-hydroxy-4-[3-(2-methoxy-ethyl)-phenyl]-but-1-enyl}-5-oxo-pyrrolidin-1-yl)-heptanoic acid ethyl ester (43 mg, 0.0965 mmol) in EtOH (20 mL) was hydrogenated in the presence of 10% palladium on carbon (20 mg) at 50 psi for 18 h. Purification by medium pressure chromatography (50% EtOAc in hexanes to EtOAc to 10% MeOH in CH$_2$Cl$_2$) provided 7-(2S-{3R-hydroxy-4-[3-(2-methoxy-ethyl)-phenyl]-butyl}-5-oxo-pyrrolidin-1-yl)-heptanoic acid ethyl ester (16 mg). MS 448.3 (M+1).

Step D: 7-(2S-{3R-Hydroxy-4-[3-(2-methoxy-ethyl)-phenyl]-butyl}-5-oxo-pyrrolidin-1-yl)-heptanoic acid. Analogous to the procedure described for Example 2A, Step E, 7-(2S-{3R-hydroxy-4-[3-(2-methoxy-ethyl)-phenyl]-butyl}-5-oxo-pyrrolidin-1-yl)-heptanoic acid ethyl ester (15 mg, 0.034 mmol) was hydrolyzed with 6M NaOH (0.20 mL) in EtOH (0.50 mL) at room temperature over 18 h to provide the title compound of Example 2I (14 mg). $^1$H NMR (CDCl$_3$) δ7.22 (m, 1H), 7.05 (m, 3H), 3.82 (m, 1H), 3.56 (m, 4H), 3.32 (s, 3H), 2.93-2.82 (m, 3H), 2.76 (m, 1H), 2.62 (m, 1H), 2.42-2.25 (m, 4H), 2.09 (m, 1H), 1.81 (m, 1H), 1.66-1.22 (m, 13H); MS 420.3 (M+1); 418.2 (M−1).

EXAMPLE 2J

7-{2R-[3-Hydroxy-4-(3-phenoxy-phenyl)-but-1-enyl]-5-oxo-pyrrolidin-1-yl}-heptanoic acid Step A: 7-{2-Oxo-5R-[3-oxo-4-(3-phenoxy-phenyl)-but-1-enyl]-pyrrolidin-1-yl}-heptanoic acid ethyl ester. Analogous to the procedure described for Example 2A, Step B, the anion derived from [2-oxo-3-(3-phenoxy-phenyl)-propyl]-phosphonic acid dimethyl ester (633 mg, 1.98 mmol) and NaH (60% in oil, 70 mg, 1.74 mmol) was reacted with 7-(2R-formyl-5-oxo-pyrrolidin-1-yl)-heptanoic acid ethyl ester (assumed 1.58 mmol) over 24 h. Medium pressure chromatography (EtOAc) provided 7-{2-oxo-5R-[3-oxo-4-(3-phenoxy-phenyl)-but-1-enyl]-pyrrolidin-1-yl}-heptanoic acid ethyl ester (215 mg). $^1$H NMR (CDCl$_3$) δ7.28 (m, 3H), 7.08 (m, 1H), 6.97 (m, 2H), 6.89 (m, 2H), 6.83 (m, 1H), 6.62 (dd, 1H), 6.19 (d, 1H), 4.13 (m, 1H), 4.08 (q, 2H), 3.79 (s, 2H), 3.51 (m, 1H), 2.68 (m, 1H), 2.35 (m, 2H), 2.24 (m, 3H), 2.24 (m, 3H), 1.75 (m, 1H), 1.54 (m, 2H), 1.43-1.20 (m, 9H).

Step B: 7-{2R-[3-hydroxy-4-(3-phenoxy-phenyl)-but-1-enyl]-5-oxo-pyrrolidin-1-yl}-heptanoic acid ethyl ester. Analogous to the procedure described for Example 2B, Step C, 7-{2-oxo-5R-[3-oxo-4-(3-phenoxy-phenyl)-but-1-enyl]-pyrrolidin-1-yl}-heptanoic acid ethyl ester (215 mg, 0.451 mmol) was reacted with NaBH$_4$ (17 mg, 0.45 mmol) in EtOH (3 mL) at 0° C. over 4 h. Purification by medium pressure chromatography (EtOAc) provided 7-{2R-[3-hydroxy-4-(3-phenoxy-phenyl)-but-1-enyl]-5-oxo-pyrrolidin-1-yl}-heptanoic acid ethyl ester (167 mg). $^1$H NMR (CDCl$_3$) δ7.33 (m, 2H), 7.25 (m, 1H), 7.10 (m, 1H), 6.99 (m, 2H), 6.93 (m, 1H), 6.86 (m, 2H), 5.72 (m, 1H), 5.45 (m, 1H), 4.37 (m, 1H), 4.10 (q, 2H), 3.47 (m, 1H), 2.82 (m, 3H), 2.35 (m, 2H), 2.26 (t, 2H), 2.15 (m, 1H), 1.70-1.21 (m, 13H).

Step C: 7-{2R-[3-Hydroxy-4-(3-phenoxy-phenyl)-but-1-enyl]-5-oxo-pyrrolidin-1-yl}-heptanoic acid. Analogous to the procedure described for Example 2A, Step E, 7-{2R-[3-hydroxy-4-(3-phenoxy-phenyl)-but-1-enyl]-5-oxo-pyrrolidin-1-yl}-heptanoic acid ethyl ester (29 mg, 0.060 mmol) was hydrolyzed with 2M NaOH in EtOH (4.0 mL) at room temperature over 24 h to provide the title compound of Example 2J (20 mg). $^1$H NMR (CDCl$_3$) δ7.33-7.21 (m, 3H), 7.08 (m, 1H), 6.98-6.84 (m, 5H), 5.70 (m, 1H), 5.44 (m, 1H), 4.36 (m, 1H), 4.00 (m, 1H), 3.44 (m, 1H), 2.85-2.51 (m, 3H), 2.32 (m, 4H), 2.14 (m, 1H), 1.68-1.18 (m, 10H).

EXAMPLE 2K

7-{2S-[3-Hydroxy-4-(3-phenoxy-phenyl)-butyl]-5-oxo-pyrrolidin-1-yl}-heptanoic acid Step A: 7-{2S-[3-Hydroxy-4-(3-phenoxy-phenyl)-butyl]-5-oxo-pyrrolidin-1-yl}-heptanoic acid ethyl ester. Analogous to the procedure described for Example 2A, Step D, a mixture of 7-{2R-[3-hydroxy4-(3-phenoxy-phenyl)-but-1-enyl]-5-oxo-pyrrolidin-1-yl}-heptanoic acid ethyl ester (139 mg, 0.290 mmol), MeOH (30 mL), and 10% palladium on carbon (14 mg) was hydrogenated on a Parr shaker at 50 psi for 18 h. Purification by medium pressure chromatography (1:1 hexanes:EtOAc) provided 7-{2S-[3-hydroxy-4-(3-phenoxy-phenyl)-butyl]-5-oxo-pyrrolidin-1-yl}-heptanoic acid ethyl ester (86 mg). $^1$H NMR (CDCl$_3$) δ7.35-7.24 (m, 3H), 7.10 (m, 1H), 6.99 (m, 2H), 6.93 (m, 1H), 6.87 (m, 2H), 4.09 (q, 2H), 3.80 (m, 1H), 3.58 (m, 2H), 2.82 (m, 2H), 2.64 (m, 1H), 2.42-2.24 (m, 4H), 2.10 (m, 1H), 1.77 (m, 1H), 1.66-1.21 (m, 16H).

Step B: 7-{2S-[3-Hydroxy-4-(3-phenoxy-phenyl)-butyl]-5-oxo-pyrrolidin-1-yl}-heptanoic acid. Analogous to the procedure described for Example 2A, Step E, 7-{2S-[3-hydroxy-4-(3-phenoxy-phenyl)-butyl]-5-oxo-pyrrolidin-1-yl}-heptanoic acid ethyl ester (86 mg, 1.79 mmol) was hydrolyzed with 2N NaOH in MeOH (4 mL) over 18 h to provide the title compound of Example 2K (62 mg). $^1$H NMR (CDCl$_3$) δ7.33-7.23 (m, 3H), 7.09 (m, 1H), 6.98 (m, 2H), 6.91 (m, 1H), 6.86 (m, 2H), 3.80 (m, 1H), 3.56 (m, 2H), 2.88 (m, 1H), 2.77 (m, 1H), 2.64 (m, 1H), 2.38-2.28 (m, 4H), 2.09 (m, 1H), 1.77 (m, 1H), 1.64-1.21 (m, 13H).

EXAMPLE 3A

5{-3-[2S-(3-Hydroxy-4-thiophen-2-yl-butyl)-5-oxo-pyrrolidin-1-yl]-propyl}-thiophene-2-carboxylic acid Step A: 5-{3-[2-Oxo-5R-(3-oxo-4-thiophen-2-yl-but-1-enyl)-pyrrolidin-1-yl]-propyl}-thiophene-2-carboxylic acid methyl ester. Analogous to the procedure described for Example 2A, Step B, the anion derived from (2-oxo-3-thiophen-2-yl-propyl)-phosphonic acid dimethyl ester (101 mg, 0.407 mmol) and NaH (60% by weight in oil, 16 mg, 0.41 mmol) was reacted with 5-[3-(2R-formyl-5-oxo-pyrrolidin-1-yl)-propyl]-thiophene-2-carboxylic acid methyl ester (prepared from 5-[3-(2R-hydroxymethyl-5-oxo-pyrrolidin-1-yl)-propyl]-thiophene-2-carboxylic acid methyl ester analogous to the procedure described for Example 2A, Step A) (assumed 0.34 mmol) over 17 h. Purification by medium pressure chromatography (1:1 hexanes:EtOAc to EtOAc) provided 5-{3-[2-oxo-5R-(3-oxo-4-thiophen-2-yl-but-1-enyl)-pyrrolidin-1-yl]-propyl}-thiophene-2-carboxylic acid methyl ester (74 mg). $^1$H NMR (CDCl$_3$) δ7.60 (d, 1H), 7.21 (m, 1H), 6.96 (m, 1H), 6.88 (m, 1H), 6.78 (d, 1H), 6.65 (dd, 1H), 6.23 (d, 1H), 4.14 (m, 1H), 4.01 (s, 2H), 3.84 (s, 3H), 3.58 (m, 1H), 2.88-2.77 (m, 3H), 2.46-2.17 (m, 3H), 1.82 (m, 3H); MS 418.0 (M+1), 416.0 (M−1).

Step B: 5-{3-[2-Oxo-5S-(3-oxo-4-thiophen-2-yl-butyl)-pyrrolidin-1-yl]-propyl}-thiophene-2-carboxylic acid methyl ester. Analogous to the procedure described for Example 2A, Step D, 5-{3-[2-oxo-5R-(3-oxo-4-thiophen-2-yl-but-1-enyl)-pyrrolidin-1-yl]-propyl}-thiophene-2-carboxylic acid methyl ester (71 mg, 0.17 mmol) was hydrogenated in EtOH (20 mL) in the presence of 10% palladium on carbon (50 mg) at 50 psi for 2 h. Additional catalyst was added (50 mg) and the reaction mixture was hydrogenated at 50 psi for an additional 1 h to provide 5-{3-[2-oxo-5S-(3-oxo-4-thiophen-2-yl-butyl)-pyrrolidin-1-yl]-propyl}-thiophene-2-carboxylic acid methyl ester (63 mg). $^1$H NMR (CDCl$_3$) δ7.61 (d, 1H), 7.22 (m, 1H), 6.97 (m, 1H), 6.88 (m, 1H), 6.80 (d, 1H), 3.88 (s, 2H), 3.84 (s, 3H), 3.65 (m, 1H), 3.52 (m, 1H), 2.95 (m, 1H), 2.81 (t, 2H), 2.48 (m, 1H), 2.30 (m, 2H), 2.07-1.80 (m, 4H), 1.55 (m, 3H); MS 419.9 (M+1), 418.0 (M−1).

Step C: 5-{3-[2S-(3-Hydroxy-4-thiophen-2-yl-butyl)-5-oxo-pyrrolidin-1-yl]-propyl}-thiophene-2-carboxylic acid methyl ester. Analogous to the procedure described for Example 2B, Step C, 5-{3-[2-oxo-5S-(3-oxo-4-thiophen-2-yl-butyl)-pyrrolidin-1-yl]-propyl}-thiophene-2-carboxylic acid methyl ester (60 mg, 0.143 mmol) was reduced with NaBH$_4$ (5 mg, 0.132 mmol) over 2 h. Purification by preparative thin layer chromatography (EtOAc) provided 5-{3-[2S-(3-hydroxy-4-thiophen-2-yl-butyl)-5-oxo-pyrrolidin-1-yl]-propyl}-thiophene-2-carboxylic acid methyl ester (10 mg). $^1$H NMR (CDCl$_3$) δ7.61 (d, 1H), 7.18 (d, 1H), 6.96 (m, 1H), 6.85 (d, 1H), 6.81 (d, 1H), 3.83 (s, 3H), 3.80 (m, 1H), 3.61 (m, 2H), 3.00 (m, 2H), 2.89 (m, 1H), 2.83 (t, 2H), 2.34 (m, 2H), 2.10 (m, 1H), 1.98-1.23 (m, 8H); MS 422.2 (M+1).

Step D: 5-{3-[2S-(3-Hydroxy-4-thiophen-2-yl-butyl)-5-oxo-pyrrolidin-1-yl]propyl}-thiophene-2-carboxylic acid. Analogous to the procedure described for Example 2A, Step E, 5-{3-[2S-(3-hydroxy-4-thiophen-2-yl-butyl)-5-oxo-pyrrolidin-1-yl]-propyl}-thiophene-2-carboxylic acid methyl ester (10 mg, 0.024 mmol) was hydrolyzed with NaOH (1M, 0.03 mL) in MeOH (5 mL) over 29 h to provide the title compound of Example 3A (10 mg). $^1$H NMR (CDCl$_3$) δ7.68 (d, 1H), 7.18 (m, 1H), 6.96 (m, 1H), 6.85 (m, 2H), 3.80 (m, 1H), 3.63 (m, 2H), 3.01 (m, 2H), 2.91 (m, 1H), 2.85 (t, 2H), 2.36 (m, 2H), 2.11 (m, 1H), 2.00-1.18 (m, 8H).

EXAMPLE 3B 5-(3-{2S-[4-(4-Chloro-phenyl)-3-hydroxy-butyl]-5-oxo-pyrrolidin-1-yl}-propyl)-thiophene-2-carboxylic acid Step A: 5-(3-{2R-[4-(4-Chloro-phenyl)-3-oxo-but-1-enyl]-5-oxo-pyrrolidin-1-yl}-propyl)-thiophene-2-carboxylic acid methyl ester. Analogous to the procedure described for Example 2A, Step B, the anion derived from [3-(4-chloro-phenyl)-2-oxo-propyl]-phosphonic acid dimethyl ester (113 mg, 0.407 mmol) and NaH (60% by weight in oil, 16 mg, 0.41 mmol) was reacted with 5-[3-(2R-formyl-5-oxo-pyrrolidin-1-yl)-propyl]-thiophene-2-carboxylic acid methyl ester (assumed 0.34 mmol) over 17 h. Purification by medium pressure chromatography (1:1 hexanes:EtOAc to EtOAc) provided 5-(3-{2R-[4-(4-chloro-phenyl)-3-oxo-but-1-enyl]-5-oxo-pyrrolidin-1-yl}-propyl)-thiophene-2-carboxylic acid methyl ester (94 mg). $^1$H NMR (CDCl$_3$) δ7.61 (d, 1H), 7.29 (m, 2H), 7.10 (d, 2H), 6.78 (d, 1H), 6.62 (dd, 1H), 6.18 (d, 1H), 4.13 (m, 1H), 3.84 (s, 3H), 3.79 (s, 2H), 3.56 (m, 1H), 2.87-2.77 (m, 3H), 2.47-2.16 (m, 3H), 1.80 (m, 3H).

Step B: 5-(3-{2S-[4-(4-Chloro-phenyl)-3-oxo-butyl]-5-oxo-pyrrolidin-1-yl}-propyl)-thiophene-2-carboxylic acid methyl ester. Analogous to the procedure described for Example 2A, Step D, 5-(3-{2R-[4-(4-chloro-phenyl)-3-oxo-but-1-enyl]-5-oxo-pyrrolidin-1-yl}-propyl)-thiophene-2-carboxylic acid methyl ester (91 mg, 0.204 mmol) was hydrogenated in EtOH (20 mL) in the presence of 10% palladium on carbon (50 mg) at 50 psi for 2 h to provide 5-(3-{2S-[4-(4-chloro-phenyl)-3-oxo-butyl]-5-oxo-pyrrolidin-1-yl}-propyl)-thiophene-2-carboxylic acid methyl ester (84 mg). $^1$H NMR (CDCl$_3$) δ7.61 (d, 1H), 7.30 (d, 2H), 7.11 (d, 2H), 6.80 (d, 1H), 3.84 (s, 3H), 3.66 (s, 2H), 3.64 (m, 1H), 3.51 (m, 1H), 2.94 (m, 1H), 2.81 (t, 2H), 2.42 (m, 2H), 2.29 (m, 2H), 2.04-1.79 (m, 4H), 1.56 (m, 2H); MS 448.0 (M+1), 446.0 (M−1).

Step C: 5-(3-{2S-[4-(4-Chloro-phenyl)-3-hydroxy-butyl]-5-oxo-pyrrolidin-1-yl}-propyl)-thiophene-2-carboxylic acid methyl ester. Analogous to the procedure described for Example 2B, Step C, 5-(3-{2S-[4-(4-chloro-phenyl)-3-oxo-butyl]-5-oxo-pyrrolidin-1-yl}-propyl)-thiophene-2-carboxylic acid methyl ester (81 mg, 0.181 mmol) was reduced with NaBH$_4$ (7 mg, 0.181 mmol) over 2 h. Purification by preparative thin layer chromatography (EtOAc, 2×) provided 5-(3-{2S-[4-(4-chloro-phenyl)-3-hydroxy-butyl]-5-oxo-pyrrolidin-1-yl}-propyl)-thiophene-2-carboxylic acid methyl ester (54 mg). $^1$H NMR (CDCl$_3$) δ7.61 (d, 1H), 7.28 (d, 2H), 7.12 (d, 2H), 6.81 (d, 1H), 3.82 (s, 3H), 3.77 (m, 1H), 3.60 (m, 2H), 2.99 (m, 1H), 2.83 (t, 2H), 2.77 (m, 1H), 2.62 (m, 1H), 2.34 (m, 2H), 2.09 (m, 1H), 1.97-1.30 (m, 8H); MS 450.0 (M+1).

Step D: 5-(3-{2S-[4-(4-Chloro-phenyl)-3-hydroxy-butyl]-5-oxo-pyrrolidin-1-yl}-propyl)-thiophene-2-carboxylic acid. Analogous to the procedure described for Example 2A, Step E, 5-(3-{2S-[4-(4-chloro-phenyl)-3-hydroxy-butyl]-5-oxo-pyrrolidin-1-yl}-propyl)-thiophene- 2-carboxylic acid methyl ester (52 mg, 0.116 mmol) was hydrolyzed with NaOH (1M, 0.14 mL) in MeOH (5 mL) under reflux over 29 h to provide 5-(3-{2S-[4-(4-chloro-phenyl)-3-hydroxy-butyl]-5-oxo-pyrrolidin-1-yl}-propyl)-thiophene-2-carboxylic acid (16 mg). $^1$H NMR (CDCl$_3$) δ7.67 (d, 1H), 7.28 (d, 2H), 7.12 (d, 2H), 6.84 (d, 1H), 3.78 (m, 1H), 3.62 (m, 1H), 3.01 (m, 1H), 2.85 (t, 2H), 2.77 (m, 1H), 2.63 (m, 1H), 2.36 (m, 2H), 2.10 (m, 1H), 1.90 (m, 3H), 1.75 (m, 1H), 1.69-1.24 (m, 4H); MS 434.0 (M−1).

EXAMPLE 3C 5-(3-{2S-[3-Hydroxy4-(2-trifluoromethyl-phenyl)-butyl]-5-oxo-pyrrolidin-1-yl}-propyl)-thiophene-2-carboxylic acid Step A: 5-(3-{2-Oxo-5R-[3-oxo-4-(2-trifluoromethyl-phenyl)-but-1-enyl]-pyrrolidin-1-yl}-propyl)-thiophene-2-carboxylic acid methyl ester. Analogous to the procedure described for Example 2A, Step B, the anion derived from [2-oxo-3-(2-trifluoromethyl-phenyl)-propyl]-phosphonic acid dimethyl ester (74 mg, 0.239 mmol) and NaH (60% by weight in oil, 10 mg, 0.239 mmol) was reacted with 5-[3-(2R-formyl-5-oxo-pyrrolidin-1-yl)-propyl]-thiophene-2-carboxylic acid methyl ester (assumed 0.239 mmol) over 17 h. Purification by medium pressure chromatography (1:1 hexanes:EtOAc to EtOAc) provided 5-(3-{2-oxo-5R-[3-oxo-4-(2-trifluoromethyl-phenyl)-but-1-enyl]-pyrrolidin-1-yl}-propyl)-thiophene-2-carboxylic acid methyl ester (32 mg). $^1$H NMR (CDCl$_3$) δ7.66 (d, 1H), 7.60 (m, 1H), 7.51 (m, 1H), 7.39 (m, 1H), 7.28 (m, 1H), 6.79 (m, 1H), 6.64 (dd, 1H), 6.22 (d, 1H), 4.16 (m, 1H), 3.83 (s, 3H), 3.78 (s, 2H), 3.60 (m, 1H), 2.93-2.79 (m, 3H), 2.48-2.20 (m, 3H), 1.83 (m, 3H); MS 479.9 (M+1). 478.0 (M−1).

Step B: 5-(3-{2-Oxo-5S-[3-oxo-4-(2-trifluoromethyl-phenyl)-butyl]-pyrrolidin-1-yl}-propyl)-thiophene-2-carboxylic acid methyl ester. Analogous to the procedure described for Example 2A, Step D, 5-(3-{2-oxo-5R-[3-oxo-4-(2-trifluoromethyl-phenyl)-but-1-enyl]-pyrrolidin-1-yl}-propyl)-thiophene-2-carboxylic acid methyl ester (29 mg, 0.060 mmol) was hydrogenated in EtOH (20 mL) in the presence of 10% palladium on carbon (40 mg) at 50 psi for 2 h to provide 5-(3-{2-oxo-5S-[3-oxo-4-(2-trifluoromethyl-phenyl)-butyl]-pyrrolidin-1-yl}-propyl)-thiophene-2-carboxylic acid methyl ester (29 mg). $^1$H NMR (CDCl$_3$) δ7.66 (d, 1H), 7.59 (m, 1H), 7.52 (m, 1H), 7.39 (m, 1H), 7.27 (m,1H), 6.80 (d, 1H), 3.83 (s, 3H), 3.78 (s, 2H), 3.64 (m, 1 H), 3.55 (m, 1H), 2.97 (m, 1H), 2.81 (t, 2H), 2.48 (m, 1H), 2.33 (m, 2H), 2.05 (m, 2H), 1.87 (m, 2H), 1.56 (m, 3H); MS 482.0 (M+1), 480.0 (M−1).

Step C: 5-(3-{2S-[3-Hydroxy-4-(2-trifluoromethyl-phenyl)-butyl]-5-oxo-pyrrolidin-1-yl}-propyl)-thiophene-2-carboxylic acid methyl ester. Analogous to the procedure described for Example 2B, Step C, 5-(3-{2-oxo-5S-[3-oxo-4-(2-trifluoromethyl-phenyl)-butyl]-pyrrolidin-1-yl}-propyl)-thiophene-2-carboxylic acid methyl ester (26 mg, 0.054 mmol) was reduced with NaBH$_4$ (2 mg, 0.054 mmol) over 2 h. Purification by preparative thin layer chromatography (EtOAc) provided 5-(3-{2S-[3-hydroxy-4-(2-trifluoromethyl-phenyl)-butyl]-5-oxo-pyrrolidin-1-yl}-propyl)-thiophene-2-carboxylic acid methyl ester (10 mg). $^1$H NMR (CDCl$_3$) δ7.65 (d, 1H), 7.59 (m, 1H), 7.49 (m, 1H), 7.36 (m, 2H), 6.81 (d, 1H), 3.81 (s, 3H), 3.81 (m, 1H), 3.62 (m, 2H), 3.02 (m, 2H), 2.83 (t, 2H), 2.78 (m, 1H), 2.34 (m, 2H), 2.12 (m, 1H), 2.01-1.35 (m, 8H); MS 484.0 (M+1).

Step D: 5-(3-{2S-[3-Hydroxy-4-(2-trifluoromethyl-phenyl)-butyl]-5-oxo-pyrrolidin-1-yl}-propyl)-thiophene-2-carboxylic acid. Analogous to the procedure described for Example 2A, Step E, 5-(3-{2S-[3-hydroxy-4-(2-trifluoromethyl-phenyl)-butyl]-5-oxo-pyrrolidin-1-yl}-propyl)-thiophene-2-carboxylic acid methyl ester (10 mg, 0.0207 mmol) was hydrolyzed with NaOH (1M, 0.07 mL) in MeOH (5 mL) heated under reflux for 29 h to provide 5-(3-{2S-[3-hydroxy-4-(2-trifluoromethyl-phenyl)-butyl]-5-oxo-pyrrolidin-1-yl}-propyl)-thiophene-2-carboxylic acid (13 mg). $^1$H NMR (CDCl$_3$) δ7.66 (m, 1H), 7.50 (m, 1H), 7.37 (m, 3H), 6.84 (d, 1H), 3.83 (m, 1H), 3.64 (m, 2H), 3.04 (m, 2H), 2.85 (t, 2H), 2.78 (m, 1H), 2.37 (m, 2H), 2.12 (m, 1H), 2.02-1.24 (m, 8H); MS 470.1 (M+1), 468.0 (M−1).

EXAMPLE 3D 5-(3-{2S-[4-(4-Fluoro-phenyl)-3-hydroxy-butyl]-5-oxo-pyrrolidin-1-yl}-propyl)-thiophene-2-carboxylic acid Step A: 5-(3-{2R-[4-(4-Fluoro-phenyl)-3-oxo-but-1-enyl]-5-oxo-pyrrolidin-1-yl}-propyl)-thiophene-2-carboxylic acid methyl ester. Analogous to the procedure described for Example 2A, Step B, the anion derived from [3-(4-fluoro-phenyl)-2-oxo-propyl]-phosphonic acid dimethyl ester (106 mg, 0.407 mmol) and NaH (60% by weight in oil, 16 mg, 0.407 mmol) was reacted with 5-[3-(2R-formyl-5-oxo-pyrrolidin-1-yl)-propyl]-thiophene-2-carboxylic acid methyl ester (assumed 0.407 mmol) over 17 h. Purification by medium pressure chromatography (1:1 hexanes:EtOAc to EtOAc) provided 5-(3-{2R-[4-(4-fluoro-phenyl)-3-oxo-but-1-enyl]-5-oxo-pyrrolidin-1-yl}-propyl)-thiophene-2-carboxylic acid methyl ester (77 mg). $^1$H NMR (CDCl$_3$) δ7.60 (d, 1H), 7.16 (m, 2H), 7.00 (m, 2H), 6.77 (d, 1H), 6.62 (dd, 1H), 6.19 (d, 1H), 4.13 (m, 1H), 3.84 (s, 3H), 3.79 (s, 2H), 3.57 (m, 1H), 2.87-2.77 (m, 3H), 2.37 (m, 2H), 2.20 (m, 1H), 1.80 (m, 3H); MS 430.0 (M+1), 428.1 (M−1).

Step B: 5-(3-{2S-[4-(4-Fluoro-phenyl)-3-oxo-butyl]-5-oxo-pyrrolidin-1-yl}-propyl)-thiophene-2-carboxylic acid methyl ester. Analogous to the procedure described for Example 2A, Step D, 5-(3-{2R-[4-(4-fluoro-phenyl)-3-oxo-but-1-enyl]-5-oxo-pyrrolidin-1-yl}-propyl)-thiophene-2-carboxylic acid methyl ester (74 mg, 0.172 mmol) was hydrogenated in EtOH (20 mL) in the presence of 10% palladium on carbon (50 mg) at 50 psi for 2 h to provide 5-(3-{2S-[4-(4-fluoro-phenyl)-3-oxo-butyl]-5-oxo-pyrrolidin-1-yl}-propyl)-thiophene-2-carboxylic acid methyl ester (72 mg). $^1$H NMR (CDCl$_3$) δ7.61 (d, 1H), 7.14 (m, 2H), 7.01 (m, 2H), 6.80 (d, 1H), 3.84 (s, 3H), 3.66 (s, 2H), 3.64 (m, 1H), 3.51 (m, 1H), 2.94 (m, 1H), 2.81 (t, 2H), 2.43 (m, 2H), 2.30 (m, 2H), 2.05-1.79 (m, 4H), 1.56 (m, 2H); MS 432.0 (M+1), 430.1 (M−1).

Step C: 5-(3-{2S-[4-(4-Fluoro-phenyl)-3-hydroxy-butyl]-5-oxo-pyrrolidin-1-yl}-propyl)-thiophene-2-carboxylic acid methyl ester. Analogous to the procedure described for Example 2B, Step C, 5-(3-{2S-[4-(4-fluoro-phenyl)-3-oxo-butyl]-5-oxo-pyrrolidin-1-yl}-propyl)-thiophene-2-carboxylic acid methyl ester (69 mg, 0.160 mmol) was reduced with NaBH$_4$ (6 mg, 0.160 mmol) over 2 h. Purification by preparative thin layer chromatography (EtOAc) provided 5-(3-{2S-[4-(4-fluoro-phenyl)-3-hydroxy-butyl]-5-oxo-pyrrolidin-1-yl}-propyl)-thiophene-2-carboxylic acid methyl ester (37 mg). $^1$H NMR (CDCl$_3$) δ7.61 (d, 1H), 7.15 (m, 2H), 7.00 (m, 2H), 6.81 (d, 1H), 3.82 (s, 3H), 3.75 (m, 1H), 3.60 (m, 2H), 2.99 (m, 1H), 2.83 (t, 2H), 2.77 (m, 1H), 2.34 (m, 2H), 2.10 (m, 1H), 2.00-1.80 (m, 4H), 1.75 (m, 1H), 1.68-1.34 (m, 4H); MS 434.3 (M+1).

Step D: 5-(3-{2S-[4-(4-Fluoro-phenyl)-3-hydroxy-butyl]-5-oxo-pyrrolidin-1-yl}-propyl)-thiophene-2-carboxylic acid. Analogous to the procedure described for Example 2A, Step E, 5-(3-{2S-[4-(4-fluoro-phenyl)-3-hydroxy-butyl]-5-oxo-pyrrolidin-1-yl}-propyl)-thiophene-2-carboxylic acid methyl ester (35 mg, 0.0807 mmol) was hydrolyzed with NaOH (1M, 0.10 mL) in MeOH (5 mL) heated under reflux over 29 h to provide 5-(3-{2S-[4-(4-fluoro-phenyl)-3-hydroxy-butyl]-5-oxo-pyrrolidin-1-yl}-propyl)-thiophene-2-carboxylic acid (36 mg). $^1$H NMR (CDCl$_3$) δ7.67 (d, 1H), 7.15 (m, 2H), 7.00 (m, 2H), 6.84 (d, 1H), 3.77 (m, 1H), 3.62 (m, 2H), 3.01 (m, 1H), 2.85 (t, 2H), 2.78 (m, 1H), 2.62 (m, 1H), 2.36 (m, 2H), 2.10 (m, 1H), 2.00-1.72 (m, 4H), 1.69-1.34 (m, 4H); MS 420.1 (M+1), 417.7 (M−1).

EXAMPLE 3E 5-(3-{2S-[4-(4-Fluoro-phenyl)-3R-hydroxy-butyl]-5-oxo-pyrrolidin-1-yl}-propyl)-thiophene-2-carboxylic acid Step A: 5-(3-{2R-[4-(4-Fluoro-phenyl)-3S-hydroxy-but-1-enyl]-5-oxo-pyrrolidin-1-yl}-propyl)-thiophene-2-carboxylic acid methyl ester. To a solution of 5-(3-{2R-[4-(4-fluoro-phenyl)-3-oxo-but-1-enyl]-5-oxo-pyrrolidin-1-yl}-propyl)-thiophene-2-carboxylic acid methyl ester (20 mg, 0.047 mmol) and (R)-2-methyl-CBS-oxazaborolidine (1M in toluene, 0.047 mL, 0.047 mmol) in anhydrous toluene (3.0 mL) at −45° C. was added catecholborane (1M in THF, 0.14 mL, 0.14 mmol) dropwise. The reaction mixture was stirred at −45° C. for 17 h. Methanol (1 mL) was added and the reaction mixture was warmed to room temperature and was concentrated in vacuo. The residue was dissolved in CHCl$_3$ and the organic solution was washed with 1M NaOH (4×5 mL), 1M HCl (1×5 mL), and water (1×5 mL). The organic solution was dried (MgSO$_4$), filtered and concentrated. Purification by preparative thin layer chromatography (EtOAc) provided 5-(3-{2R-[4-(4-fluoro-phenyl)-3S-hydroxy-but-1-enyl]-5-oxo-pyrrolidin-1-yl}-propyl)-thiophene-2-carboxylic acid methyl ester as an approximate 39:1 ratio of 3S:3R alcohol diastereomers by HPLC. MS 432.1 (M+1).

Step B: 5-(3-{2S-[4-(4-Fluoro-phenyl)-3R-hydroxy-butyl]-5-oxo-pyrrolidin-1-yl}-propyl)-thiophene-2-carboxylic acid methyl ester. Analogous to the procedure described for Example 2A, Step D, 5-(3-{2R-[4-(4-fluoro-phenyl)-3S-hydroxy-but-1-enyl]-5-oxo-pyrrolidin-1-yl}-propyl)-thiophene-2-carboxylic acid methyl ester (15 mg, 0.035 mmol) was hydrogenated in ethanol (10 mL) in the presence of 10% palladium on carbon (5 mg) at 50 psi for 2 h to provide 5-(3-{2S-[4-(4-fluoro-phenyl)-3R-hydroxy-butyl]-5-oxo-pyrrolidin-1-yl}-propyl)-thiophene-2-carboxylic acid methyl ester (11 mg). $^1$H NMR (CDCl$_3$) δ7.60 (d, 1H), 7.14 (m, 2H), 7.00 (m, 2H), 6.81 (d, 1H), 3.82 (s, 3H), 3.77 (m, 1H), 3.60 (m, 2H), 3.00 (m, 1H), 2.83 (t, 2H), 2.76 (d, 1H), 2.63 (dd, 1H), 2.34 (m, 2H), 2.08 (m, 1H), 1.98-1.42 (m, 8H); MS 434.1 (M+1).

Step C: 5-(3-{2S-[4-(4-Fluoro-phenyl)-3R-hydroxy-butyl]-5-oxo-pyrrolidin-1-yl}-propyl)-thiophene-2-carboxylic acid. Analogous to the procedure described for Example 2A, Step E, 5-(3-{2S-[4-(4-fluoro-phenyl)-3R-hydroxy-butyl]-5-oxo-pyrrolidin-1-yl}-propyl)-thiophene-2-carboxylic acid methyl ester (11 mg, 0.0254 mmol) was hydrolyzed with NaOH (1M, 0.25 mL) in MeOH (4 mL) heated under reflux for 3 h to provide 5-(3-{2S-[4-(4-fluoro-phenyl)-3R-hydroxy-butyl]-5-oxo-pyrrolidin-1-yl}-propyl)-thiophene-2-carboxylic acid (9 mg). $^1$H NMR (CDCl$_3$) δ7.67 (d, 1H), 7.14 (m, 2H), 6.99 (m, 2H), 6.83 (d, 1H), 3.78 (m, 1H), 3.62 (m, 2H), 3.02 (m, 1H), 2.85 (t, 2H), 2.76 (dd, 1H), 2.64 (dd, 1H), 2.37 (m, 2H), 2.09 (m, 1H), 2.00-1.42 (m, 8H); MS 420.1 (M+1), 418.0 (M−1).

EXAMPLE 3F

5-{3-[2S-(3-Hydroxy-4-naphthalen-2-yl-butyl)-5-oxo-pyrrolidin-1-yl]-propyl}-thiophene-2-carboxylic acid Step A: 5-{3-[2R-(4-Naphthalen-2-yl-3-oxo-but-1-enyl)-5-oxo-Pyrrolidin-1-yl]propyl}-thiophene-2-carboxylic acid tert-butyl ester. Analogous to the procedure described for Example 2A, Step B, the anion derived from (3-naphthalen-2-yl-2-oxo-propyl)-phosphonic acid dimethyl ester (208 mg, 0.71 mmol) and NaH (60% by weight in oil, 26 mg, 0.65 mmol) was reacted with 5-[3-(2R-formyl-5-oxo-pyrrolidin-1-yl)-propyl]-thiophene-2-carboxylic acid tert-butyl ester (assumed 0.589 mmol) over 18 h. Purification by medium pressure chromatography (1:1 hexanes:EtOAc to EtOAc) provided 5-{3-[2R-(4-naphthalen-2-yl-3-oxo-but-1-enyl)-5-oxo-pyrrolidin-1-yl]-propyl}-thiophene-2-carboxylic acid tert-butyl ester (181 mg). $^1$H NMR (CDCl$_3$) δ7.79 (m, 3H), 7.65 (s, 1H), 7.47 (m, 3H), 7.29 (m, 1H), 6.63 (m, 2H), 6.22 (d, 1H), 4.08 (m, 1H), 3.98 (s, 2H), 3.49 (m, 1H), 2.73 (m, 1H), 2.63 (m, 2H), 2.36 (m, 2H), 2.19 (m, 1H), 1.72 (m, 3H), 1.54 (s, 9H); MS 504.1 (M+1), 502.0 (M−1).

Step B: 5-{3-[2S-(4-Naphthalen-2-yl-3-oxo-butyl)-5-oxo-pyrrolidin-1-yl]-propyl}-thiophene-2-carboxylic acid tert-butyl ester. Analogous to the procedure described for Example 2A, Step D, 5-{3-[2R-(4-naphthalen-2-yl-3-oxo-but-1-enyl)-5-oxo-pyrrolidin-1-yl]-propyl}-thiophene-2-carboxylic acid tert-butyl ester (178 mg, 0.353 mmol) was hydrogenated in EtOH (40 mL) in the presence of 10% palladium on carbon (75 mg) at 50 psi for 3 h. Purification by medium pressure chromatography (1:1 hexanes:EtOAc to EtOAc) provided 5-{3-[2S-(4-naphthalen-2-yl-3-oxo-butyl)-5-oxo-pyrrolidin-1-yl]-propyl}-thiophene-2-carboxylic acid tert-butyl ester (144 mg). $^1$H NMR (CDCl$_3$) δ7.80 (m, 3H), 7.66 (s, 1H), 7.48 (m, 3H), 7.30 (m, 1H), 6.74 (d, 1H), 3.85 (s, 2H), 3.59 (m, 1H), 3.48 (m, 1H), 2.89 (m, 1H), 2.73 (t, 2H), 2.47 (m, 2H), 2.26 (m, 2H), 2.04-1.74 (m, 4H), 1.53 (s, 9H), 1.50 (m, 2H); MS 506.1 (M+1), 503.8 (M−1).

Step C: 5-{3-[2S-(3-Hydroxy-4-naphthalen-2-yl-butyl)-5-oxo-pyrrolidin-1-yl]-propyl}-thiophene-2-carboxylic acid tert-butyl ester. Analogous to the procedure described for Example 2B, Step C, 5-{3-[2S-(4-naphthalen-2-yl-3-oxo-butyl)-5-oxo-pyrrolidin-1-yl]-propyl}-thiophene-2-carboxylic acid tert-butyl ester (142 mg, 0.281 mmol) was reduced with NaBH$_4$ (11 mg, 0.281 mmol) over 2 h. Purification by medium pressure chromatography (1:1 hexanes:EtOAc to EtOAc) provided 5-{3-[2S-(3-hydroxy-4-naphthalen-2-yl-butyl)-5-oxo-pyrrolidin-1-yl]-propyl}-thiophene-2-carboxylic acid tert-butyl ester (125 mg). $^1$H NMR (CDCl$_3$) δ7.79 (m, 3H), 7.65 (s, 1H), 7.52 (d, 1H), 7.46 (m, 2H), 7.32 (d, 1H), 6.76 (d, 1H), 3.90 (m, 1H), 3.62 (m, 2H), 2.98 (m, 2H), 2.81 (m, 3H), 2.34 (m, 2H), 2.10 (m, 1H), 2.04-1.75 (m, 2H), 1.70-1.36 (m, 6H), 1.52 (s, 9H); MS 508.0(M+1).

Step D: 5-{3-[2S-(3-Hydroxy-4-naphthalen-2-yl-butyl)-5-oxo-pyrrolidin-1-propyl}-thiophene-2-carboxylic acid. To a solution of 5-{3-[2S-(3-hydroxy-4-naphthalen-2-yl-butyl)-5-oxo-pyrrolidin-1-yl]-propyl}-thiophene-2-carboxylic acid tert-butyl ester (123 mg, 0.242 mmol) in CH$_2$Cl$_2$ (20 mL) at 0° C. was added TFA (0.19 mL, 0.247 mmol). The reaction mixture was stirred at room temperature for 23 h and was concentrated in vacuo. The residue was purified by preparative thin layer chromatography (EtOAc) to provide the title compound of Example 3F (47 mg). $^1$H NMR (CDCl$_3$) δ7.78 (m, 3H), 7.63 (m, 2H), 7.44 (m, 2H), 7.31 (m, 1H), 6.78 (m, 1H), 3.89 (m, 1H), 3.57 (m, 2H), 2.94 (m, 2H), 2.79 (m, 3H), 2.32 (m, 2H), 2.10-1.17 (m, 9H); MS 452.3 (M+1), 450.2 (M−1).

EXAMPLE 3G

5-{3-[2S-(4-Biphenyl-3-yl-3-hydroxy-butyl)-5-oxo-pyrrolidin-1-yl]-propyl}-thiophene-2-carboxylic acid Step A: 5-{3-[2R-(4-Biphenyl-3-yl-3-oxo-but-1-enyl)-5-oxo-pyrrolidin-1-yl]-propyl}-thiophene-2-carboxylic acid methyl ester. Analogous to the procedure described for Example 2A, Step B, the anion derived from (3-biphenyl-3-yl-2-oxo-propyl)-phosphonic acid dimethyl ester (3.217 g, 10.09 mmol) and NaH (60% by weight in oil, 404 mg, 10.09 mmol) was reacted with 5-[3-(2R-formyl-5-oxo-pyrrolidin-1-yl)-propyl]-thiophene-2-carboxylic acid methyl ester (assumed 10.09 mmol) over 17 h. Purification by medium pressure chromatography (solvent gradient 9:1 hexanes:EtOAc to EtOAc) provided 5-{3-[2R-(4-bi phenyl-3-yl-3-oxo-but-1-enyl)-5-oxo-pyrrolidin-1-yl]-propyl}-thiophene-2-carboxylic acid methyl ester (4.0 g). $^1$H NMR (CDCl$_3$) δ7.56 (m, 3H), 7.49 (m, 1H), 7.42 (m, 4H), 7.34 (m, 1H), 7.16 (d, 1H), 6.73 (d, 1H), 6.62 (dd, 1H), 6.22 (d, 1H), 4.11 (m, 1H), 3.88 (s, 2H), 3.82 (s, 3H), 3.54 (m, 1H), 2.79 (m, 1H), 2.73 (t, 2H), 2.36 (m, 2H), 2.20 (m, 1H), 1.76 (m, 3H); MS 488.1 (M+1), 486.0 (M−1).

Step B: 5-{3-[2S-(4-Biphenyl-3-yl-3-oxo-butyl)-5-oxo-pyrrolidin-1-yl]-propyl}-thiophene-2-carboxylic acid methyl ester. Analogous to the procedure described for Example 2A, Step D, a mixture of 5-{3-[2R-(4-biphenyl-3-yl-3-oxo-but-1-enyl)-5-oxo-pyrrolidin-1-yl]-propyl}-thiophene-2-carboxylic acid methyl ester (3.535 g, 7.25 mmol), 10% palladium on carbon (750 mg), and EtOH (250 mL) was hydrogenated at 50 psi for 2 h to provide 5-{3-[2S-(4-biphenyl-3-yl-3-oxo-butyl)-5-oxo-pyrrolidin-1-yl]-propyl}-thiophene-2-carboxylic acid methyl ester which was used without further purification in Step C. MS 490.1 (M+1).

Step C: 5-{3-[2S-(4-Biphenyl-3-yl-3-hydroxy-butyl)-5-oxo-pyrrolidin-1-yl]-propyl}-thiophene-2-carboxylic acid ethyl ester. Analogous to the procedure described for Example 2B, Step C, 5-{3-[2S-(4-biphenyl-3-yl-3-oxo-butyl)-5-oxo-pyrrolidin-1-yl]-propyl}-thiophene-2-carboxylic acid methyl ester (7.25 mmol) was treated with NaBH$_4$ (274 mg, 7.25 mmol) in EtOH at room temperature for 1 h. Purification by medium pressure chromatography (1:1 hexanes:EtOAc to EtOAc) provided 5-{3-[2S-(4-biphenyl-3-yl-3-hydroxy-butyl)-5-oxo-pyrrolidin-1-yl]-propyl}-thiophene-2-carboxylic acid ethyl ester (1.68 g). $^1$H NMR (CDCl$_3$) δ7.58 (m, 3H), 7.40 (m, 6H), 7.17 (d, 1H), 6.79 (d, 1H), 4.27 (q, 2H), 3.85 (m, 1H), 3.62 (m, 2H), 3.00 (m, 1H), 2.86 (m, 3H), 2.71 (m, 1H), 2.34 (m, 2H), 2.10 (m, 1H), 2.01-1.75 (m, 4H), 1.70-1.35 (m, 4H), 1.31 (t, 3H); MS 506.1 (M+1).

Step D: 5-{3-[2S-(4-Biphenyl-3-yl-3-hydroxy-butyl)-5-oxo-pyrrolidin-1-yl]-propyl}-thiophene-2-carboxylic acid. Analogous to the procedure described for Example 2A, Step E, 5-{3-[2S-(4-biphenyl-3-yl-3-hydroxy-butyl)-5-oxo-pyrrolidin-1-yl]-propyl}-thiophene-2-carboxylic acid ethyl ester (1.882 g, 3.72 mmol) was hydrolyzed with NaOH (1 M, 5.6 mL) in MeOH (100 mL) over 3 h under reflux to provide the title compound of Example 3G (1.741 g). $^1$H NMR (CDCl$_3$) δ7.66 (d, 1H), 7.56 (d, 2H), 7.40 (m, 6H), 7.17 (d, 1H), 6.82 (d, 1H), 3.85 (m, 1H), 3.63 (m, 2H), 3.02 (m, 1H), 2.86 (m, 3H), 2.72 (m, 1H), 2.36 (m, 2H), 2.11 (m, 1H), 2.01-1.75 (m, 4H), 1.71-1.35 (m, 4H); MS 478.1 (M+1), 476.0 (M−1).

EXAMPLE 3H 5-(3{-2S-[4-(3-Fluoro-phenyl)-3-hydroxy-butyl]-5-oxo-pyrrolidin-1-yl}-propyl)-thiophene-2-carboxylic acid Step A: 5-(3-{2R-[4-(3-Fluoro-phenyl)-3-oxo-but-1-enyl]-5-oxo-pyrrolidin-1-yl}-propyl)-thiophene-2-carboxylic acid methyl ester. Analogous to the procedure described for Example 2A, Step B, the anion derived from [3-(3-fluoro-phenyl)-2-oxo-propyl]-phosphonic acid dimethyl ester (3.236 g, 12.4 mmol) and NaH (60% in oil, 458 mg, 11.4 mmol) was reacted with 5-[3-(2R-formyl-5-oxo-pyrrolidin-1-yl)-propyl]-thiophene-2-carboxylic acid methyl ester (assumed 10.4 mmol) over 18 h. Purification by medium pressure chromatography eluting with 20% EtOAc in hexanes to 80% EtOAc in hexanes followed by a second column eluting with 20% acetone in toluene to 30% acetone in toluene provided 5-(3-{2R-[4-(3-fluoro-phenyl)-3-oxo-but-1-enyl]-5-oxo-pyrrolidin-1-yl}-propyl)-thiophene-2-carboxylic acid methyl ester (2.95 g). $^1$H NMR (CDCl$_3$) δ7.60 (d, 1H), 7.27 (m, 1H), 6.92 (m, 3H), 6.76 (d, 1H), 6.60 (dd, 1H), 6.18 (d, 1), 4.12 (m, 1H), 3.83 (s, 3H), 3.80 (s, 2H), 3.56 (m, 1H), 2.82 (m, 1H), 2.77 (t, 2H), 2.37 (m, 2H), 2.22 (m, 1H), 1.78 (m, 3H).

Step B: 5-(3-{2S-[4-(3-Fluoro-phenyl)-3-oxo-butyl]-5-oxo-pyrrolidin-1-yl}-propyl)-thiophene-2-carboxylic acid methyl ester. Analogous to the procedure described for Example 2A, Step D, 5-(3-{2R-[4-(3-fluoro-phenyl)-3-oxo-but-1-enyl]-5-oxo-pyrrolidin-1-yl}-propyl)-thiophene-2-carboxylic acid methyl ester (2.95 g, 6.87 mmol) was hydrogenated in MeOH (60 mL) in the presence of 10% palladium on carbon (500 mg) at 50 psi for 2 h. Purification by medium pressure chromatography (50% EtOAc in hexanes to EtOAc) provided 5-(3-{2S-[4-(3-fluoro-phenyl)-3-oxo-butyl]-5-oxo-pyrrolidin-1-yl}-propyl)-thiophene-2-carboxylic acid methyl ester (2.60 g). $^1$H NMR (CDCl$_3$) δ7.60 (d, 1H), 7.28 (m, 1H), 6.92 (m, 3H), 6.79 (d, 1H), 3.82 (s, 3H), 3.67 (s, 2H), 3.62 (m, 1H), 3.50 (m, 1H), 2.93 (m, 1H), 2.80 (t, 2H), 2.43 (m, 2H), 2.27 (m, 2H), 2.04-1.76 (m, 4H), 1.50 (m, 2H); MS 432.2 (M+1), 430.1 (M−1).

Step C: 5-(3-{2S-[4-(3-Fluoro-phenyl)-3-hydroxy-butyl]-5-oxo-pyrrolidin-1-yl}-propyl)-thiophene-2-carboxylic acid methyl ester. Analogous to the procedure described for Example 2B, Step C, 5-(3-{2S-[4-(3-fluoro-phenyl)-3-oxo-butyl]-5-oxo-pyrrolidin-1-yl}-propyl)-thiophene-2-carboxylic acid methyl ester (2.60 g, 6.03 mmol) was reacted with NaBH$_4$ (114 mg, 3.01 mmol) in MeOH (30 mL) at 0° C. for 3 h. Purification by medium pressure chromatography (EtOAc to 2% MeOH in CH$_2$Cl$_2$) provided 5-(3-{2S-[4-(3-fluoro-phenyl)-3-hydroxy-butyl]-5-oxo-pyrrolidin-1-yl}-propyl)-thiophene-2-carboxylic acid methyl ester (2.43 g). MS 434.0 (M+1).

Step D: 5-(3-{2S-[4-(3-Fluoro-phenyl)-3-hydroxy-butyl]-5-oxo-pyrrolidin-1-yl}-propyl)-thiophene-2-carboxylic acid. Analogous to the procedure described for Example 2A, Step E, 5-(3-{2S-[4-(3-fluoro-phenyl)-3-hydroxy-butyl]-5-oxo-pyrrolidin-1-yl}-propyl)-thiophene-2-carboxylic acid methyl ester (2.43 g) was hydrolyzed with 2N NaOH in MeOH (30 mL) over 18 h to provide 5-(3-{2S-[4-(3-fluoro-phenyl)-3-hydroxy-butyl]-5-oxo-pyrrolidin-1-yl}-propyl)-thiophene-2-carboxylic acid (2.06 g). Step E: Sodium salt of 5-(3-{2S-[4-(3-Fluoro-phenyl)-3-hydroxy-butyl]-5-oxo-pyrrolidin-1-yl}-propyl)-thiophene-2-carboxylic acid.

Analogous to the procedure described for Example 2D, Step E, 5-(3-{2S-[4-(3-fluoro-phenyl)-3-hydroxy-butyl]-5-oxo-pyrrolidin-1-yl}-propyl)-thiophene-2-carboxylic acid (2.058 g, 4.905 mmol) was reacted with NaHCO$_3$ (412 mg, 4.906 mmol) to yield the sodium salt of the title compound of Example 3H. $^1$H NMR (CD$_3$OD) δ7.35 (d, 1H), 7.26 (m, 1H), 6.96 (m, 3H), 6.75 (d, 1H), 3.76 (m, 1H), 3.67 (m, 1H), 3.57 (m, 1H), 3.02 (m, 1H), 2.76 (m, 3H), 2.30 (m, 2H), 2.10 (m, 1H), 1.98-1.28 (m, 9H).

EXAMPLE 3I 5-(3-{2S-[4-(4-Ethyl-phenyl)-3-hydroxy-butyl]-5-oxo-pyrrolidin-1-yl}-propyl)-thiophene-2-carboxylic acid Step A: 5-(3-{2R-[4-(4-Ethyl-phenyl)-3-oxo-but-1-enyl]-5-oxo-pyrrolidin-1-yl}-propyl)-thiophene-2-carboxylic acid methyl ester. Analogous to the procedure described for Example 2A, Step B, the anion derived from [3-(4-ethyl-phenyl)-2-oxo-propyl]-phosphonic acid diethyl ester (274 mg, 0.915 mmol) and NaH (60% by weight in oil, 41 mg, 1.01 mmol) was reacted with 5-[3-(2R-formyl-5-oxo-pyrrolidin-1-yl)-propyl]-thiophene-2-carboxylic acid methyl ester (assumed 1.01 mmol) over 18 h. Purification by medium pressure chromatography (1:1 hexanes:EtOAc to EtOAc) provided 5-(3-{2R-[4-(4-ethyl-phenyl)-3-oxo-but-1-enyl]-5-oxo-pyrrolidin-1-yl}-propyl)-thiophene-2-carboxylic acid methyl ester (227 mg). $^1$H NMR (CDCl$_3$) δ7.59 (d, 1H), 7.13 (d, 2H), 7.07 (d, 2H), 6.75 (d, 1H), 6.58 (dd, 1H), 6.18 (d, 1H), 4.10 (m, 1H), 3.83 (s, 3H), 3.77 (s, 2H), 3.53 (m, 1H), 2.78 (m, 3H), 2.59 (q, 2H), 2.36 (m, 2H), 2.19 (m, 1H), 1.76 (m, 3H), 1.19 (t, 3H); MS 440.2 (M+1).

Step B: 5-(3-{2S-[4-(4-Ethyl-phenyl)-3-oxo-butyl]-5-oxo-pyrrolidin-1-yl}-propyl)-thiophene-2-carboxylic acid methyl ester. Analogous to the procedure described for Example 2A, Step D, 5-(3-{2R-[4-(4-ethyl-phenyl)-3-oxo-but-1-enyl]-5-oxo-pyrrolidin-1-yl}-propyl)-thiophene-2-carboxylic acid methyl ester (227 mg, 0.517 mmol) was hydrogenated in MeOH (30 mL) in the presence of 10% palladium on carbon at 50 psi for 1.5 h. Purification by medium pressure chromatography (1:1 hexanes:EtOAc to EtOAc) provided 5-(3-{2S-[4-(4-ethyl-phenyl)-3-oxo-butyl]-5-oxo-pyrrolidin-1-yl}-propyl)-thiophene-2-carboxylic acid methyl ester (119 mg). $^1$H NMR (CDCl$_3$) δ7.62 (d, 1H), 7.16 (d, 2H), 7.10 (d, 2H), 6.81 (d, 1H), 3.84 (s, 3H), 3.65 (s, 2H), 3.63 (m, 1H), 3.49 (m, 1H), 2.95 (m, 1H), 2.80 (t, 2H), 2.62 (q, 2H), 2.43 (m, 2H), 2.31 (m, 2H), 2.06-1.79 (m, 4H), 1.48 (m, 2H), 1.21 (t, 3H); MS 442.2 (M+1).

Step C: 5-(3-{2S-[4-(4-Ethyl-phenyl)-3-hydroxy-butyl]-5-oxo-pyrrolidin-1-yl}-propyl)-thiophene-2-carboxylic acid methyl ester. Analogous to the procedure described for Example 2B, Step C, 5-(3-{2S-[4-(4-ethyl-phenyl)-3-oxo-butyl]-5-oxo-pyrrolidin-1-yl}-propyl)-thiophene-2-carboxylic acid methyl ester (109 mg, 0.247 mmol) was reduced with NaBH$_4$ (5 mg, 0.132 mmol) in MeOH (7 mL) at 0° C. to room temperature over 3 h. Purification by medium pressure chromatography (1:1 hexanes:EtOAc to EtOAc) provided 5-(3-{2S-[4-(4-ethyl-phenyl)-3-hydroxy-butyl]-5-oxo-pyrrolidin-1-yl}-propyl)-thiophene-2-carboxylic acid methyl ester (77 mg). $^1$H NMR (CDCl$_3$) δ7.61 (d, 1H), 7.16 (d, 2H), 7.10 (d, 2H), 6.81 (d, 1H), 3.83 (s, 3H), 3.77 (m, 1H), 3.62 (m, 2H), 3.01 (m, 1H), 2.83 (t, 2H), 2.77 (m, 1H), 2.60 (m, 3H), 2.35 (m, 2H), 2.09 (m, 1H), 1.99-1.34 (m, 8H), 1.22 (t, 3H); MS 444.3 (M+1).

Step D: 5-(3-{2S-[4-(4-Ethyl-phenyl)-3-hydroxy-butyl]-5-oxo-pyrrolidin-1-yl}-propyl)-thiophene-2-carboxylic acid. Analogous to the procedure described for Example 2A, Step E, 5-(3-{2S-[4-(4-ethyl-phenyl)-3-hydroxy-butyl]-5-oxo-pyrrolidin-1-yl}-propyl)-thiophene-2-carboxylic acid methyl ester (76 mg) was hydrolyzed with 2N NaOH in MeOH (7 mL) over 18 h to provide the title compound of Example 3I(58 mg). $^1$H NMR (CD$_3$OD) δ7.57 (m, 1H), 7.08 (d, 4H), 6.88 (d, 1H), 3.72 (m, 1H), 3.63 (m, 1H), 3.52 (m, 1H), 2.99 (m, 1H), 2.81 (t, 2H), 2.68 (m, 2H), 2.56 (q, 2H), 2.27 (m, 2H), 2.06 (m, 1H), 1.95-1.25 (m, 6H), 1.16 (t, 3H); MS 430.3 (M+1), 428.5 (M−1).

EXAMPLE 3J 5-(3-{2S-[4-(4-Fluoro-3-methyl-phenyl)-3-hydroxy-butyl]-5-oxo-pyrrolidin-1-yl}-propyl)-thiophene-2-carboxylic acid Step A: 5-(3-{2R-[4-(4-Fluoro-3-methyl-phenyl)-3-oxo-but-1-enyl]-5-oxo-pyrrolidin-1-yl}-propyl)-thiophene-2-carboxylic acid methyl ester. Analogous to the procedure described for Example 2A, Step B, the anion derived from [3-(4-fluoro-3-methyl-phenyl)-2-oxo-propyl]-phosphonic acid diethyl ester (273 mg, 0.903 mmol) and NaH (60% by weight in oil, 41 mg, 1.01 mmol) was reacted with 5-[3-(2R-formyl-5-oxo-pyrrolidin-1-yl)-propyl]-thiophene-2-carboxylic acid methyl ester (assumed 1.01 mmol) over 18 h. Purification by medium pressure chromatography (20% EtOAc in hexanes to EtOAc) provided 5-(3-{2R-[4-(4-fluoro-3-methyl-phenyl)-3-oxo-but-1-enyl]-5-oxo-pyrrolidin-1-yl}-propyl)-thiophene-2-carboxylic acid methyl ester (174 mg). $^1$H NMR (CDCl$_3$) δ7.59 (d, 1H), 6.97 (d, 1H), 6.93 (d, 2H), 6.76 (d, 1H), 6.60 (dd, 1H), 6.18 (d, 1H), 4.11 (m, 1H), 3.82 (s, 3H), 3.73 (s, 2H), 3.56 (m, 1H), 2.82 (m, 1H), 2.77 (t, 2H), 2.36 (m, 2H), 2.22 (s, 3H), 2.19 (m, 1H), 1.78 (m, 3H); MS 444.2 (M+1); 442.2 (M−1).

Step B: 5-(3-{2S-[4-(4-Fluoro-3-methyl-phenyl)-3-oxo-butyl]-5-oxo-pyrrolidin-1-yl}-propyl)-thiophene-2-carboxylic acid methyl ester. Analogous to the procedure described for Example 2A, Step D, 5-(3-{2R-[4-(4-fluoro-3-methyl-phenyl)-3-oxo-but-1-enyl]-5-oxo-pyrrolidin-1-yl}-propyl)-thiophene-2-carboxylic acid methyl ester (174 mg, 0.392 mmol) was hydrogenated in MeOH (30 mL) in the presence of 10% palladium on carbon (70 mg) at 50 psi for 1.5 h. Purification by medium pressure (30% EtOAc in hexanes to EtOAc) provided 5-(3-{2S-[4-(4-fluoro-3-methyl-phenyl)-3-oxo-butyl]-5-oxo-pyrrolidin-1-yl}-propyl)-thiophene-2-carboxylic acid methyl ester (114 mg). $^1$H NMR (CDCl$_3$) δ7.60 (d, 1H), 6.97 (d, 1H), 6.93 (d, 2H), 6.79 (d, 1H), 3.82 (s, 3H), 3.63 (m, 1H), 3.60 (s, 2H), 3.50 (m, 1H), 2.93 (m, 1H), 2.79 (t, 2H), 2.42 (m, 2H), 2.33-2.21 (m, 5H), 2.02-1.78 (m, 4H), 1.50 (m, 2H); MS 446.1 (M+1).

Step C: 5-(3-{2S-[4-(4-Fluoro-3-methyl-phenyl)-3-hydroxy-butyl]-5-oxo-pyrrolidin-1-yl}-propyl)-thiophene-2-carboxylic acid methyl ester. Analogous to the procedure described for Example 2B, Step C, 5-(3-{2S-[4-(4-fluoro-3-methyl-phenyl)-3-oxo-butyl]-5-oxo-pyrrolidin-1-yl}-propyl)-thiophene-2-carboxylic acid methyl ester (114 mg, 0.256 mmol) was reduced with NaBH$_4$ (5 mg, 0.132 mmol) in MeOH (10 mL) at 0° C. to room temperature over 2.5 h. Purification by medium pressure chromatography (1:1 hexanes:EtOAc to EtOAc) provided 5-(3-{2S-[4-(4-fluoro-3-methyl-phenyl)-3-hydroxy-butyl]-5-oxo-pyrrolidin-1yl}-propyl)-thiophene-2-carboxylic acid methyl ester (80 mg). $^1$H NMR (CDCl$_3$) δ7.59 (d, 1H), 6.98 (d, 1H), 6.93 (m, 2H), 6.80 (d, 1H), 3.81 (s, 3H), 3.74 (m, 1H), 3.60 (m, 2H), 2.99 (m, 1H), 2.82 (t, 2H), 2.72 (m, 1H), 2.54 (m, 1H), 2.33 (m, 2H), 2.22 (s, 3H), 2.08 (m, 1H), 1.96-1.32 (m, 8H); MS 448.1 (M+1).

Step D: 5-(3-{2S-[4-(4-Fluoro-3-methyl-phenyl)-3-hydroxy-butyl]-5-oxo-pyrrolidin-1-yl}-propyl)-thiophene-2-carboxylic acid. Analogous to the procedure described for Example 2A, Step E, 5-(3-{2S-[4-(4-fluoro-3-methyl-phenyl)-3-hydroxy-butyl]-5-oxo-pyrrolidin-1-yl}-propyl)-thiophene-2-carboxylic acid methyl ester (80 mg, 0.179 mmol) was hydrolyzed with 2N NaOH in MeOH (6 mL) over 18 h to provide the title compound of Example 3J (56 mg). $^1$H NMR (CD$_3$OD) δ7.58 (d, 1H), 7.08-6.98 (m, 2H), 6.90 (m, 2H), 3.69 (m, 2H), 3.55 (m, 1H), 3.04 (m, 1H), 2.84 (t, 2H), 2.67 (m, 2H), 2.31 (m, 2H), 2.21 (s, 3H), 2.11 (m, 1H), 1.98-1.27 (m, 7H); MS 432.4 (M−1).

EXAMPLE 3K

5-{3-[2S-(3-Hydroxy-4-phenyl-butyl)-5-oxo-pyrrolidin-1-yl]-propyl}-thiophene-2-carboxylic acid Step A: 5-{3-[2-Oxo-5R-(3-oxo-4-phenyl-but-1-enyl)-pyrrolidin-1-yl]-propyl}-thiophene-2-carboxylic acid methyl ester. Analogous to the procedure described for Example 2A, Step B, the anion derived from (2-oxo-3-phenyl-propyl)-phosphonic acid dimethyl ester (543 mg, 2.24 mmol) and NaH (60% by weight in oil, 94 mg, 2.35 mmol) was reacted with 5-[3-(2R-formyl-5-oxo-pyrrolidin-1-yl)-propyl]-thiophene-2-carboxylic acid methyl ester (assumed 2.36 mmol) over 18 h. Purification by medium pressure chromatography (20% EtOAc in hexanes to 70% EtOAc in hexanes) provided 5-{3-[2-oxo-5R-(3-oxo-4-phenyl-but-1-enyl)-pyrrolidin-1-yl]-propyl}-thiophene-2-carboxylic acid methyl ester (315 mg). $^1$H NMR (CDCl$_3$) δ7.61 (d, 1H), 7.34-7.15 (m, 5H), 6.77 (m, 1H), 6.61 (dd, 1H), 6.19 (d, 1H), 4.12 (m, 1H), 3.85 (s, 3H), 3.82 (s, 2H), 3.54 (m, 1H), 2.81 (m, 3H), 2.37 (m, 2H), 2.20 (m, 1H), 1.78 (m, 3H); MS 411.8 (M+1); 409.7 (M−1).

Step B: 5-{3-[2-Oxo-5S-(3-oxo-4-phenyl-butyl)-pyrrolidin-1-yl]-propyl}-thiophene-2-carboxylic acid methyl ester. Analogous to the procedure described for Example 2A, Step D, 5-{3-[2-oxo-5R-(3-oxo-4-phenyl-but-1-enyl)-pyrrolidin-1-yl]-propyl}-thiophene-2-carboxylic acid methyl ester (305 mg, 0.741 mmol) was hydrogenated in MeOH (30 mL) in the presence of 10% palladium on carbon (100 mg) at 50 psi for 1.5 h. Purification by medium pressure (1:1 hexanes:EtOAc to EtOAc) provided 5-{3-[2-oxo-5S-(3-oxo-4-phenyl-butyl)-pyrrolidin-1-yl]-propyl}-thiophene-2-carboxylic acid methyl ester (235 mg). $^1$H NMR (CDCl$_3$) δ7.62 (d, 1H), 7.35-7.18 (m, 5H), 6.81 (d, 1H), 3.84 (s, 3H), 3.69 (s, 2H), 3.62 (m, 1H), 3.48 (m, 1H), 2.94 (m, 1H), 2.80 (t, 2H), 2.43 (m, 2H), 2.26 (m, 2H), 2.04-1.78 (m, 4H), 1.48 (m, 2H); MS 414.1 (M+1).

Step C: 5-{3-[2S-(3-Hydroxy-4-phenyl-butyl)-5-oxo-pyrrolidin-1-yl]-propyl}-thiophene-2-carboxylic acid methyl ester. Analogous to the procedure described for Example 2B, Step C, 5-{3-[2-oxo-5S-(3-oxo-4-phenyl-butyl)-pyrrolidin-1-yl]-propyl}-thiophene-2-carboxylic acid methyl ester (235 mg, 0.569 mmol) was reduced with NaBH$_4$ (11 mg, 0.284 mmol) in MeOH (7 mL) at 0° C. to room temperature over 2 h. Purification by medium pressure chromatography (30% EtOAc in hexanes to EtOAc) provided 5-{3-[2S-(3-hydroxy-4-phenyl-butyl)-5-oxo-pyrrolidin-1-yl]-propyl}-thiophene-2-carboxylic acid methyl ester (177 mg). $^1$H NMR (CDCl$_3$) δ7.70 (d, 1H), 7.32-7.16 (m, 5H), 6.79 (d, 1H), 3.80 (m, 4H), 3.60 (m, 2H), 2.99 (m, 1H), 2.80 (m, 3H), 2.62 (m, 1H), 2.32 (m, 2H), 2.09 (m, 1H), 1.97-1.32 (m, 8H); MS 416.0 (M+1).

Step D: 5-{3-[2S-(3-Hydroxy-4-phenyl-butyl)-5-oxo-pyrrolidin-1-yl]-propyl}-thiophene-2-carboxylic acid. Analogous to the procedure described for Example 2A, Step E, 5-{3-[2S-(3-hydroxy-4-phenyl-butyl)-5-oxo-pyrrolidin-1-yl]-propyl}-thiophene-2-carboxylic acid methyl ester (177 mg, 0.426 mmol) was hydrolyzed with 2N NaOH in MeOH (7 mL) over 18 h to provide the title compound of Example 3K (132 mg). $^1$H NMR (CD$_3$OD) δ7.57 (m, 1H), 7.26-7.14 (m, 5H), 6.88 (d, 1H), 3.75 (m, 1H), 3.64 (m, 1H), 3.54 (m, 1H), 3.00 (m, 1H), 2.82 (t, 2H), 2.71 (m, 2H), 2.28 (m, 2H), 2.08 (m, 1H), 1.96-1.26 (m, 7H); MS 402.2 (M+1), 400.4 (M−1).

EXAMPLE 3L 5-(3-{2S-[4-(3-Chloro-phenyl)-3R-hydroxy-butyl]-5-oxo-pyrrolidin-1-yl}-propyl)-thiophene-2-carboxylic acid Step A: 5-(3-{2R-[4-(3-Chloro-phenyl)-3-oxo-but-1-enyl]-5-oxo-pyrrolidin-1-yl}-propyl)-thiophene-2-carboxylic acid methyl ester. Analogous to the procedure described for Example 2C, Step D, the anion derived from [3-(3-chloro-phenyl)-2-oxo-propyl]-phosphonic acid dimethyl ester (3.68 g, 13.3 mmol) and NaH (60% by weight in oil, 533 mg, 14.5 mmol) was reacted with 5-[3-(2R-formyl-5-oxo-pyrrolidin-1-yl)-propyl]-thiophene-2-carboxylic acid methyl ester (assumed 12.1 mmol) over 24 h. Purification by medium pressure chromatography (15% acetone in toluene to 20% acetone in toluene) provided 5-(3-{2R-[4-(3-chloro-phenyl)-3-oxo-but-1-enyl]-5-oxo-pyrrolidin-1-yl}-propyl)-thiophene-2-carboxylic acid methyl ester (2.63 g). $^1$H NMR (CDCl$_3$) δ7.59 (d, 1H), 7.23 (m, 2H), 7.16 (s, 1H), 7.04 (m, 1H), 6.76 (d, 1H), 6.60 (dd, 1H), 6.17 (d, 1H), 4.12 (m, 1H), 3.82 (s, 3H), 3.78 (s, 2H), 3.56 (m, 1H), 2.87-2.75 (m, 3H), 2.45-2.28 (m, 2H), 2.21 (m, 1H), 1.78 (m, 3H).

Step B: 5-(3-{2R-[4-(3-Chloro-phenyl)-3S-hydroxy-but-1-enyl]-5-oxo-pyrrolidin-1-yl}-propyl)-thiophene-2-carboxylic acid methyl ester. To a solution of 5-(3-{2R-[4-(3-chloro-phenyl)-3-oxo-but-1-enyl]-5-oxo-pyrrolidin-1-yl}-propyl)-thiophene-2-carboxylic acid methyl ester (2.63 g, 5.91 mmol) and (R)-2-methyl-CBS-oxazaborolidine (1M in toluene, 5.9 mL, 5.9 mmol in CH$_2$Cl$_2$ (140 mL) at −45° C was added catecholborane (1M in THF, 17.7 mL, 17.7 mmol) dropwise. The reaction mixture was stirred for 18 h and MeOH was added. After stirring for 18 h, the volatiles were removed in vacuo and CH$_2$Cl$_2$ was added. The organic solution was washed with cold lN NaOH (3 times), 1N HCl, water and brine. The organic solution was dried (MgSO$_4$), filtered and concentrated. Purification by medium pressure chromatography (1:1 hexanes:EtOAc to 80% EtOAc in hexanes) provided 5-(3-{2R-[4-(3-chloro-phenyl)-3S-hydroxy-but-1-enyl]-5-oxo-pyrrolidin-1-yl}-propyl)-thiophene-2-carboxylic acid methyl ester (870 mg) as an approximate 10:1 ratio of 3S:3R alcohol diastereomers by $^1$H NMR. $^1$H NMR (CDCl$_3$) δ7.61 (d, 1H), 7.21 (m, 3H), 7.07 (m, 1H), 6.80 (d, 1H), 5.68 (dd, 1H), 5.45 (dd, 1H), 4.36 (m, 1H), 4.01 (m, 1H), 3.82 (s, 3H), 3.51 (m, 1H), 2.84-2.76 (m, 5H), 2.44-2.28 (m, 2H), 2.18 (m, 1H), 1.86-1.56 (m, 4H).

Step C: 5-(3-{2S-[4-(3-Chloro-phenyl)-3R-hydroxy-butyl]-5-oxo-pyrrolidin-1-yl}-propyl)-thiophene-2-carboxylic acid methyl ester. Analogous to the procedure described for Example 2A, Step D, a mixture of 5-(3-{2R-[4-(3-chloro-phenyl)-3S-hydroxy-but-1-enyl]-5-oxo-pyrrolidin-1-yl}-propyl)-thiophene-2-carboxylic acid methyl ester (850 mg) and 10% palladium on carbon (100 mg) in MeOH (50 mL) was hydrogenated on a Parr shaker at 50 psi for 3 h. The hydrogenation was repeated using 100 mg of 10% palladium on carbon for 6 h. Purification by medium pressure chromatography (1:1 hexanes:EtOAc to EtOAc) provided 5-(3-{2S-[4-(3-chloro-phenyl)-3R-hydroxy-butyl]-5-oxo-pyrrolidin-1-yl}-propyl)-thiophene-2-carboxylic acid methyl ester (504 mg). $^1$H NMR (CDCl$_3$) δ7.61 (d, 1H), 7.23 (m, 3H), 7.08 (m, $_1$H), 6.82 (d, 1H), 3.83 (s, 3H), 3.81 (m, 1H), 3.62 (m, 2H), 3.01 (m, 1H), 2.84 (t, 2H), 2.77 (m, 1H), 2.65 (m, 1H), 2.35 (m, 2H), 2.10 (m, 1H), 1.97-1.43 (m, 8H).

Step D: 5-(3-{2S-[4-(3-Chloro-phenyl)-3R-hydroxy-butyl]-5-oxo-pyrrolidin-1-yl}-propyl)-thiophene-2-carboxylic acid. Analogous to the procedure described for Example 2A, Step E, 5-(3-{2S-[4-(3-chloro-phenyl)-3R-hydroxy-butyl]-5-oxo-pyrrolidin-1-yl}-propyl)-thiophene-2-carboxylic acid methyl ester (504 mg) was hydrolyzed with 2N NaOH in MeOH (20 mL) at 50° C. over 4 h to provide the title compound of Example 3L (338.6 mg). $^1$H NMR (CDCl$_3$) δ7.68 (d, 1H), 7.22 (m, 3H), 7.08 (m, 1H), 6.84 (d, 1H), 3.80 (m, 1H), 3.64 (m, 2H), 3.01 (m, 1H), 2.82 (m, 4H), 2.64 (m, 1H), 2.38 (m, 2H), 2.12 (m, 1H), 1.92 (m, 3H), 1.66 (m, 1H), 1.57-1.19 (m, 3H). MS 436.1 (M+1), 434.2 (M−1).

EXAMPLE 3M 5-(3-{2S-[3R-Hydroxy-4-(3-trifluoromethyl-phenyl)-butyl]-5-oxo-pyrrolidin-1-yl}-propyl)-thiophene-2-carboxylic acid Step A: 5-(3-{2-Oxo-5R-[3-oxo-4-(3-trifluoromethyl-phenyl)-but-1-enyl]-pyrrolidin-1yl}-propyl)-thiophene-2-carboxylic acid methyl ester. Analogous to the procedure described for Example 2A, Step B, the anion derived from [2-oxo-3-(3-trifluoromethyl-phenyl)-propyl]-phosphonic acid dimethyl ester (5.026 g, 17.0 mmol) and NaH (60% by weight in oil, 750 mg, 18.8 mmol) was reacted with 5-[3-(2R-formyl-5-oxo-pyrrolidin-1-yl)-propyl]-thiophene-2-carboxylic acid methyl ester (assumed 18.8 mmol) over 24 h. Purification by medium pressure chromatography (15% acetone in toluene to 20% acetone in toluene) provided 5-(3-{2-oxo-5R-[3-oxo-4-(3-trifluoromethyl-phenyl)-but-1-enyl]-pyrrolidin-1-yl}-propyl)-thiophene-2-carboxylic acid methyl ester (4.02 g). $^1$H NMR (CDCl$_3$) δ7.61 (d, 1H), 7.54 (d, 1H), 7.45 (m, 2H), 7.37 (d, 1H), 6.79 (d, 1H), 6.66 (dd, 1H), 6.20 (d, 1H), 4.16 (m, 1H), 3.90 (s, 2H), 3.84 (s, 3H), 3.60 (m, 1H), 2.89-2.78 (m, 3H), 2.48-2.31 (m, 2H), 2.23 (m, 1H), 1.82 (m, 3H).

Step B: 5-(3-{2R-[3S-Hydroxy-4-(3-trifluoromethyl-phenyl)-but-1-enyl]-5-oxo-pyrrolidin-1-yl}-propyl)-thiophene-2-carboxylic acid methyl ester. Analogous to the procedure described for Example 2A, Step C, 5-(3-{2-oxo-5R-[3-oxo-4-(3-trifluoromethyl-phenyl)-but-1-enyl]-pyrrolidin-1-yl}-propyl)-thiophene-2-carboxylic acid methyl ester (2.63 g, 5.91 mmol) was reduced with catecholborane (1M in THF, 18.8 mL, 18.8 mmol) in the presence of (R)-2-methyl-CBS-oxazaborolidine (1M in toluene, 0.94 mL, 0.94 mmol) at −45° C. over 18 h. The reaction was quenched by addition of 1N HCl and the mixture was stirred for 40 minutes. The organic solution was washed consecutively with ice cold 1N NaOH (3 times), 1N HCl (1 time), water (1 time), and brine. The organic solution was dried (MgSO$_4$), filtered, and concentrated. Purification by medium pressure chromatography (10% acetone in toluene to 20% acetone in toluene) provided 5-(3-{2R-[3S-hydroxy-4-(3-trifluoromethyl-phenyl)-but-1-enyl]-5-oxo-pyrrolidin-1-yl}-propyl)-thiophene-2-carboxylic acid methyl ester (3 g) as an approximate 4:1 ratio of 3S:3R alcohol diastereomers by $^1$H NMR. $^1$H NMR (CDCl$_3$) δ7.60 (d, 1H), 7.50 (d, 1H), 7.41 (m, 3H), 6.79 (d, 1H), 5.70 (dd, 1H), 5.48 (dd, 1H), 4.41 (m, 1H), 4.00 (m, 1H), 3.81 (s, 3H), 3.50 (m, 1H), 2.86-2.77 (m, 5H), 2.42-2.26 (m, 2H), 2.16 (m, 1H), 1.81 (m, 2H), 1.72-1.54 (m, 2H).

Step C: 5-(3-{2S-[3R-Hydroxy-4-(3-trifluoromethyl-phenyl)-butyl]-5-oxo-pyrrolidin-1-yl}-propyl)-thiophene-2-carboxylic acid methyl ester. Analogous to the procedure described for Example 2A, Step D, a mixture of 5-(3-{2R-[3S-hydroxy-4-(3-trifluoromethyl-phenyl)-but-1-enyl]-5-oxo-pyrrolidin-1-yl}-propyl)-thiophene-2-carboxylic acid methyl ester (3 g) and 10% palladium on carbon (400 mg) in MeOH (70 mL) was hydrogenated on a Parr shaker at 50 psi for 16 h. Purification by medium pressure chromatography (20% EtOAc in hexanes to 70% EtOAc in hexanes) provided 5-(3-{2S-[3R-hydroxy-4-(3-trifluoromethyl-phenyl)-butyl]-5-oxo-pyrrolidin-1-yl}-propyl)-thiophene-2-carboxylic acid methyl ester (2.26 g). $^1$H NMR (CDCl$_3$) δ7.61 (d, 1H), 7.52-7.38 (m, 4H), 6.81 (d, 1H), 3.83 (m, 4H), 3.63 (m, 2H), 3.00 (m, 1H), 2.85 (m, 3H), 2.74 (m, 1H), 2.34 (m, 2H), 2.10 (m, 1H), 1.98-1.45 (m, 08H).

Step D: 5-(3-{2S-[3R-Hydroxy-4-(3-trifluoromethyl-phenyl)-butyl]-5-oxo-pyrrolidin-1-yl}-propyl)-thiophene-2-carboxylic acid. Analogous to the procedure described for Example 2A, Step E, 5-(3-{2S-[3R-hydroxy-4-(3-trifluoromethyl-phenyl)-butyl]-5-oxo-pyrrolidin-1-yl}-propyl)-thiophene-2-carboxylic acid methyl ester (625 mg) was hydrolyzed with 2N NaOH in MeOH (20 mL) at room temperature over 24 h to provide the title compound of Example 3M (599 mg). $^1$H NMR (CDCl$_3$) δ7.67 (d,1H), 7.51-7.38 (m, 4H), 6.84 (d, 1H), 3.85 (m, 1H), 3.63 (m, 2H), 3.02 (m, 1H), 2.85 (m, 3H), 2.75 (m, 1H), 2.37 (m, 2H), 2.11 (m, 1H), 2.00-1.45 (m, 8H); MS 470.2 (M+1), 468.2 (M−1).

EXAMPLE 4A 5S-(3-Hydroxy-4-naphthalen -2-yl-butyl)-1-[6-(2H-tetrazol-5-yl)-hexyl]-pyrrolidin-2-one Step A: 7-(2R-Formyl-5-oxo-pyrrolidin-1-yl)-heptanenitrile. Analogous to the procedure described for Example 2A, Step A, 7-(2R-hydroxymethyl-5-oxo-pyrrolidin-1-yl)-heptanenitrile (150 mg, 0.67 mmol) was oxidized to generate 7-(2R-formyl-5-oxo-pyrrolidin-1-yl)-heptanenitrile which was used in Step B without further purification.

Step B: 7-[2R-(4-Naphthalen-2-yl-3-oxo-but-1-enyl)-5-oxo-pyrrolidin-1-yl]-heptanenitrile. Analogous to the procedure described for Example 2A, Step B, the anion derived from (3-naphthalen-2-yl-2-oxo-propyl)-phosphonic acid dimethyl ester (196 mg, 0.67 mmol) and NaH (60% by weight in oil, 27 mg, 0.67 mmol) was reacted with 7-(2R-formyl-5-oxo-pyrrolidin-1-yl)-heptanenitrile (assumed 0.67 mmol) over 19 h. Purification by medium pressure chromatography (1:1 hexanes:EtOAc to EtOAc) provided 7-[2R-(4-naphthalen-2-yl-3-oxo-but-1-enyl)-5-oxo-pyrrolidin-1-yl]-heptanenitrile (74 mg). $^1$H NMR (CDCl$_3$) δ7.79 (m, 3H), 7.67 (m, 1H), 7.46 (m, 2H), 7.30 (d, 1H), 6.65 (dd, 1H), 6.25 (d, 1H), 4.10 (m, 1H), 3.99 (s, 2H), 3.42 (m, 1H), 2.66 (m, 1H), 2.37 (m, 2H), 2.22 (m, 3H), 1.76 (m, 1H), 1.52 (m, 2H), 1.29 (m, 4H), 1.10 (m, 2H); MS 389.1 (M+1), 387.0 (M−1).

Step C: 7-[2S-(4-Naphthalen-2-yl-3-oxo-butyl)-5-oxo-pyrrolidin-1-yl]-heptanenitrile. Analogous to the procedure described for Example 2A, Step D, 7-[2R-(4-naphthalen-2-yl-3-oxo-but-1-enyl)-5-oxo-pyrrolidin-1-yl]-heptanenitrile (74 mg, 0.19 mmol) was hydrogenated in EtOH (30 mL) in the presence of 10% palladium on carbon (50 mg) at 50 psi for 3 h. Purification by medium pressure (1:1 hexanes:EtOAc to EtOAc) provided 7-[2S-(4-naphthalen-2-yl-3-oxobutyl)-5-oxo-pyrrolidin-1-yl]-heptanenitrile (45 mg). $^1$H NMR (CDCl$_3$) δ7.80 (m, 3H), 7.66 (s, 1H), 7.47 (m, 2H), 7.30 (d, 1H), 3.85 (s, 2H), 3.51 (m, 2H), 2.81 (m, 1H), 2.48 (m, 2H), 2.28 (m, 4H), 1.98 (m, 2H), 1.62 (m, 4H), 1.44 (m, 4H), 1.22 (m, 2H); MS 391.4 (M+1), 389.3 (M−1).

Step D: 7-[2S-(3-Hydroxy-4-naphthalen-2-yl-butyl)-5-oxo-pyrrolidin-1-yl]-heptanenitrile. Analogous to the procedure described for Example 2B, Step C, 7-[2S-(4-naphthalen-2-yl-3-oxo-butyl)-5-oxo-pyrrolidin-1-yl]-heptanenitrile (42 mg, 0.108 mmol) was reduced with NaBH$_4$ (4 mg, 0.11 mmol) in EtOH (20 mL) at room temperature for 3 h to provide 7-[2S-(3-hydroxy-4-naphthalen-2-yl-butyl)-5-oxo-pyrrolidin-1-yl]-heptanenitrile (40 mg). $^1$H NMR (CDCl$_3$) δ7.80 (m, 3H), 7.65 (m, 1H), 7.46 (m, 2H), 7.33 (d, 1H), 3.92 (m, 1H), 3.59 (m, 2H), 3.03-2.78 (m, 3H), 2.35 (m, 4H), 2.12 (m, 1H), 1.81 (m, 1H), 1.68-1.40 (m, 11H), 1.28 (m, 2H); MS 393.1 (M+1).

Step E: 5S-(3-Hydroxy-4-naphthalen-2-yl-butyl)-1-[6-(2H-tetrazol-5-yl)-hexyl]-pyrrolidin-2-one. A solution of 7-[2S-(3-hydroxy-4-naphthalen-2-yl-butyl)-5-oxo-pyrrolidin-1-yl]-heptanenitrile (39 mg, 0.0994 mmol), azidotrimethylsilane (150 mg, 1.30 mmol), and dibutyltin oxide (25 mg, 0.10 mmol) in toluene (15 mL) was heated under reflux for 19 h. The reaction mixture was cooled and was acidified to pH of 2 with 1N HCl (5 mL). The volatiles were removed in vacuo and the aqueous solution was washed with EtOAc (4×10 mL). The organic solutions were combined, dried (MgSO$_4$), filtered and concentrated. The residue was purified by preparative thin layer chromatography (9:1 EtOAc:MeOH) to provide 5S-(3-hydroxy-4-naphthalen-2-yl-butyl)-1-[6-(2H-tetrazol-5-yl)-hexyl]-pyrrolidin-2-one (11 mg). $^1$H NMR (CDCl$_3$) δ7.79 (m, 3H), 7.65 (m, 1H), 7.45 (m, 2H), 7.32 (m, 1H), 3.94 (m, 1H), 3.66 (m, 1H), 3.52 (m, 1H), 3.03-2.83 (m, 5H), 2.44 (m, 2H), 2.18 (m, 1H), 1.87-1.20 (m, 14H); MS 436.1 (M+1), 435.2 (M−1).

EXAMPLE 4B

5S-[3R-Hydroxy-4-(3-methoxymethyl-phenyl)-butyl]-1-[6-(2H-tetrazol-5-yl)-hexyl]-pyrrolidin-2-one Step A: 7-{2R-[4-(3-Methoxymethyl-phenyl)-3-oxo-but-1-enyl]-5-oxo-pyrrolidin-1-yl}-heptanenitrile. Analogous to the procedure described for Example 2A, Step B, the anion derived from [3-(3-methoxymethyl-phenyl)-2-oxo-propyl]-phosphonic acid diethyl ester (2.87 g, 9.13 mmol) and NaH (60% in oil, 446 mg, 11.2 mmol) was reacted with 7-(2R-formyl-5-oxo-pyrrolidin-1-yl)-heptanenitrile (assumed 11.15 mmol) over 24 h. Purification by medium pressure chromatography (1:1 hexanes:EtOAc to EtOAc to 1% MeOH in CH$_2$Cl$_2$ to 3% MeOH in CH$_2$Cl$_2$) provided 7-{2R-[4-(3-methoxymethyl-phenyl)-3-oxo-but-1-enyl]-5-oxo-pyrrolidin-1-yl}-heptanenitrile (2.06 g). $^1$H NMR (CDCl$_3$) δ7.29 (m, 1H), 7.22 (m, 1H), 7.16 (s, 1H), 7.10 (m, 1H), 6.62 (dd, 1H), 6.20 (d, 1H), 4.41 (s, 2H), 4.12 (m, 1H), 3.82 (s, 2H), 3.49 (m, 1H), 3.37 (s, 3H), 2.72 (m, 1H), 2.43-2.20 (m, 5H), 1.76 (m, 1H), 1.60 (m, 2H), 1.40 (m, 4H), 1.24 (m, 2H)

Step B: 7-{2R-[3S-Hydroxy-4-(3-methoxymethyl-phenyl)-but-1-enyl]-5-oxo-pyrrolidin-1-yl}-heptanenitrile. To a solution of 7-{2R-[4-(3-methoxymethyl-phenyl)-3-oxo-but-1-enyl]-5-oxo-pyrrolidin-1-yl}-heptanenitrile (2.06 g, 5.39 mmol) and (R)-2-methyl-CBS-oxazaborolidine (1M in toluene, 0.81 mL, 0.81 mmol) in CH$_2$Cl$_2$ (200 mL) at −45° C. was added catecholborane (1M in THF, 16.2 mL, 16.2 mmol) dropwise. The reaction mixture was stirred at −45° C. for 24 h and 1N HCl was added. The reaction mixture was stirred at room temperature for 1 h and the layers were separated. The aqueous solution was washed with CH$_2$Cl$_2$ (2 times) and the organic solutions were combined, washed with cold 1N NaOH followed by brine 2 times. The organic solution was dried (MgSO$_4$), filtered and concentrated. Purification by medium pressure chromatography (1:1 hexanes:EtOAc to EtOAc to 1% MeOH in CH$_2$Cl$_2$ to 3% MeOH in CH$_2$Cl$_2$) provided 7-{2R-[3S-hydroxy-4-(3-methoxymethyl-phenyl)-but-1-enyl]-5-oxo-pyrrolidin-1-yl}-heptanenitrile (2.07 g) as an approximate 2:1 mixture of 3S:3R alcohol diastereomers by $^1$H NMR. $^1$H NMR (CDCl$_3$) δ7.30-7.09 (m, 4H), 5.71 (m, 1H), 5.46 (m, 1H), 4.41 (s, 2H), 4.38 (m, 1H), 4.00 (m, 1H), 3.45 (m, 1H), 3.38 (s, 3H), 2.88-2.68 (m, 3H), 2.31 (m, 4H), 2.17 (m, 1H), 1.70-1.21 (m, 10H).

Step C: 7-{2S-[3R-Hydroxy-4-(3-methoxymethyl-phenyl)-butyl]-5-oxo-pyrrolidin-1-yl}-heptanenitrile. Analogous to the procedure described for Example 2A, Step D, 7-{2R-[3S-hydroxy-4-(3-methoxymethyl-phenyl)-but-1-enyl]-5-oxo-pyrrolidin-1-yl}-heptanenitrile (2.07 g, 5.39 mmol) in EtOH (100 mL) was hydrogenated in the presence of 10% palladium on carbon (200 mg) at 50 psi for 24 h on a Parr shaker. Purification by medium pressure chromatography (1:1 hexanes:EtOAc to 2:1 EtOAc:hexanes to EtOAc to 2% MeOH in CH$_2$Cl$_2$ to 5% MeOH in CH$_2$Cl$_2$ to 10% MeOH in CH$_2$Cl$_2$) provided 7-{2S-[3R-hydroxy-4-(3-methoxymethyl-phenyl)-butyl]-5-oxo-pyrrolidin-1-yl}-heptanenitrile (1.28 g). $^1$H NMR (CDCl$_3$) δ7.30-7.10 (m, 4H), 4.41 (s, 2H), 3.82 (m, 1H), 3.57 (m, 2H), 3.38 (s, 3H), 2.89 (m, 2H), 2.66 (m, 1H), 2.32 (m, 4H), 2.10 (m, 1H), 1.77 (m, 1H), 1.66-1.40 (m, 11H), 1.29 (m, 2H).

Step D: 5S-[3R-Hydroxy-4-(3-methoxymethyl-phenyl)-butyl]-1-[6-(2H-tetrazol-5-yl)-hexyl]-pyrrolidin-2-one. Analogous to the procedure described for Example 4A, Step E, 7-{2S-[3R-hydroxy-4-(3-methoxymethyl-phenyl)-butyl]-5-oxo-pyrrolidin-1-yl}-heptanenitrile (1.28 g, 3.31 mmol) was reacted with azidotrimethylsilane (0.90 mL, 6.78 mmol) and dibutyltin oxide (128 mg, 0.514 mmol) in toluene (68 mL) heated under reflux for 24 h. Additional azidotrimethylsilane (1.8 mL, 13.56 mmol) and dibutyltin oxide (256 mg, 1.03 mmol) were added and the reaction mixture was continued under reflux for 3 days. Purification by medium pressure chromatography (CH$_2$Cl$_2$ to 2% MeOH in CH$_2$Cl$_2$ to 4% MeOH in CH$_2$Cl$_2$ to 6% MeOH in CH$_2$Cl$_2$ to 10% MeOH in CH$_2$Cl$_2$) provided 5S-[3R-hydroxy-4-(3-methoxymethyl-phenyl)-butyl]-1-[6-(2H-tetrazol-5-yl)-hexyl]-pyrrolidin-2-one (619.5 mg). $^1$H NMR (CDCl$_3$) δ7.30-7.11 (m, 4H), 4.42 (s, 2H), 3.87 (m, 1H), 3.64 (m, 1H), 3.52 (m, 1H), 3.39 (s, 3H), 2.99-2.67 (m, 5H), 2.42 (m, 2H), 2.16 (m, 1H), 1.87-1.25 (m, 14H).

Step E: Sodium salt of 5S-[3R-Hydroxy-4-(3-methoxymethyl-phenyl)-butyl]-1-[6-(2H-tetrazol-5-yl)-hexyl]-pyrrolidin-2-one. Analogous to the procedure described for Example 2C, Step D, treatment of 5S-[3R-hydroxy-4-(3-methoxymethyl-phenyl)-butyl]-1-[6-(2H-tetrazol-5-yl)-hexyl]-pyrrolidin-2-one (619.5 mg, 1.44 mmol) with NaHCO$_3$ (121 mg, 1.44 mmol) provided the sodium salt of the title compound of Example 4B (628.3 mg). $^1$H NMR (CD$_3$OD) δ7.20 (m, 4H), 3.79 (m, 1H), 3.64 (m, 1H), 3.50 (m, 1H), 2.97-2.69 (m, 5H), 2.29 (m, 2H), 2.10 (m, 1H), 1.81-1.28 (m, 14H).

EXAMPLE 5A

2-{3-[2S-(3-Hydroxy-4-phenyl-butyl)-5-oxo-pyrrolidin-1-yl]-propyl}-thiazole-4-carboxylic acid Step A: 2-{3-[2-Oxo-5R-(3-oxo-4-phenyl-but-1-enyl)-pyrrolidin-1-yl]-propyl}-thiazole-4-carboxylic acid ethyl ester. Analogous to the procedure described for Example 2A, Step B, the anion derived from (2-oxo-3-phenyl-propyl)-phosphonic acid dimethyl ester (105 mg, 0.434 mmol) and NaH (60% by weight in oil, 17 mg, 0.434 mmol) was reacted with 2-[3-(2R-formyl-5-oxo-pyrrolidin-1-yl)-propyl]-thiazole-4-carboxylic acid ethyl ester (prepared from 2-[3-(2R-hydroxymethyl-5-oxo-pyrrolidin-1-yl)-propyl]-thiazole-4-carboxylic acid ethyl ester analogous to the procedure described for Example 2A, Step A, assumed 0.359 mmol) over 17 h. Purification by medium pressure chromatography (1:1 hexanes:EtOAc to EtOAc) provided 2-{3-[2-oxo-5R-(3-oxo-4-phenyl-but-1-enyl)-pyrrolidin-1-yl]-propyl}-thiazole-4-carboxylic acid ethyl ester (59 mg). $^1$H NMR (CDCl$_3$) δ8.03 (s, 1H), 7.33-7.17 (m, 5H), 6.61 (dd, 1H), 6.20 (d, 1H), 4.40 (q, 2H), 4.19 (m, 1H), 3.82 (s, 2H), 3.60 (m, 1H), 2.98 (m, 2H), 2.80 (m, 1H), 2.44-2.15 (m, 3H), 1.94 (m, 2H), 1.75 (m, 1H), 1.38 (t, 3H); MS 427.0 (M+1), 424.9 (M−1).

Step B: 2-{3-[2-Oxo-5S-(3-oxo-4-phenyl-butyl)-pyrrolidin-1-yl]-propyl}-thiazole-4-carboxylic acid ethyl ester. Analogous to the procedure described for Example 2A, Step D, 2-{3-[2-oxo-5R-(3-oxo-4-phenyl-but-1-enyl)-pyrrolidin-1-yl]-propyl}-thiazole-4-carboxylic acid ethyl ester (23 mg, 0.0539 mmol) was hydrogenated in EtOH (15 mL) in the presence of 10% palladium on carbon (15 mg) at 50 psi for 3 h. Purification by preparative thin layer chromatography (1:1 hexanes:EtOAc) (2 times) provided 2-{3-[2-oxo-5S-(3-oxo-4-phenyl-butyl)-pyrrolidin-1-yl]-propyl}-thiazole-4-carboxylic acid ethyl ester (19 mg). $^1$H NMR (CDCl$_3$) δ8.03 (s, 1H), 7.34-7.17 (m, 5H), 4.39 (q, 2H), 3.68 (s, 2H), 3.65 (m, 1H), 3.53 (m, 1H), 2.98 (m, 3H), 2.43 (t, 2H), 2.26 (m, 2H), 1.98 (m, 4H), 1.49 (m, 2H), 1.37 (t, 3H); MS 429.0 (M+1).

Step C: 2-{3-[2S-(3-Hydroxy-4-phenyl-butyl)-5-oxo-pyrrolidin-1-yl]-propyl}-thiazole-4-carboxylic acid ethyl ester. Analogous to the procedure described for Example 2B, Step C, 2-{3-[2-oxo-5S-(3-oxo-4-phenyl-butyl)-pyrrolidin-1-yl]-propyl}-thiazole-4-carboxylic acid ethyl ester (34 mg, 0.0793 mmol) was reduced with NaBH$_4$ (3 mg, 0.079 mmol) in EtOH (10 mL) at room temperature for 2 h. Purification by preparative thin layer chromatography (EtOAc) provided 2-{3-[2S-(3-hydroxy-4-phenyl-butyl)-5-oxo-pyrrolidin-1-yl]-propyl}-thiazole-4-carboxylic acid ethyl ester (18 mg). $^1$H NMR (CDCl$_3$) δ8.02 (m, 1H), 7.33-7.18 (m, 5H), 4.38 (q, 2H), 3.82 (m, 1H), 3.65 (m, 2H), 3.06 (m, 3H), 2.80 (m, 1H), 2.67 (m, 1H), 2.32 (m, 2H), 2.09 (m, 2H), 1.98 (m, 2H), 1.82 (m, 1H), 1.68-1.42 (m, 4H), 1.37 (t, 3H); MS 431.1 (M+1).

Step D: 2-{3-[2S-(3-Hydroxy-4-phenyl-butyl)-5-oxo-pyrrolidin-1-yl]-propyl}-thiazole-4-carboxylic acid. Analogous to the procedure described for Example 2A, Step E, 2-{3-[2S-(3-hydroxy-4-phenyl-butyl)-5-oxo-pyrrolidin-1-yl]-propyl}-thiazole-4-carboxylic acid ethyl ester (18 mg, 0.042 mmol) was hydrolyzed with 1N NaOH (0.06 mL) in MeOH (5 mL) heated under reflux for 3 h to provide the title compound of Example 5A (8 mg). $^1$H NMR (CDCl$_3$) δ8.01 (s, 1H), 7.33-7.18 (m, 5H), 3.83 (m, 1H), 3.66 (m, 2H), 3.09 (m, 1H), 3.02 (t, 2H), 2.81 (m, 1H), 2.68 (m, 1H), 2.35 (m, 2H), 2.06 (m, 4H), 1.82 (m, 1H), 1.69-1.38 (m, 4H); MS 403.0 (M+1), 401.0 (M−1).

Step E: Sodium salt of 2-{3-[2S-(3-Hydroxy-4-phenyl-butyl)-5-oxo-pyrrolidin-1-yl]-propyl}-thiazole-4-carboxylic acid. The sodium salt of the title compound of Example 5A was prepared Analogous to the procedure described for Example 2B, Step E. $^1$H NMR (CDCl$_3$) δ7.58 (s, 1H), 7.25-7.14 (m, 5H), 3.75 (m, 1H), 3.36 (m, 2H), 2.78 (m, 1H), 2.61 (m, 3H), 2.16-1.20 (m, 12H).

EXAMPLE 5B 5-(3-Hydroxy-4-phenyl-butyl)-1-{3-[4-(2H-tetrazol-5-yl)-phenyl]-propyl}-pyrrolidin-2-one Step A: 4-(3-{2-[3-(tert-Butyl-dimethyl-silanyloxy)-4-phenyl-butyl]-5-oxo-pyrrolidin-1-yl}-propyl)-benzonitrile. Analogous to the procedure described for Example 1A, Step D, the anion derived from 5-[3-(tert-butyl-dimethyl-silanyloxy)-4-phenyl-butyl]-pyrrolidin-2-one (262.8 mg, 0.756 mmol) and NaHMDS (0.83 mL, 0.83 mmol) was reacted with 4-(3-bromo-propyl)-benzonitrile (186 mg, 0.832 mmol) at 70° C. for 24 h. Purification by medium pressure chromatography (5:1 hexanes:EtOAc to 1:1 hexanes:EtOAc to 1% MeOH in CH$_2$Cl$_2$ to 5% MeOH in CH$_2$Cl$_2$) provided 4-(3-{2-[3-(tert-butyl-dimethyl-silanyloxy)-4-phenyl-butyl]-5-oxo-pyrrolidin-1-yl}-propyl)-benzonitrile (257.6 mg). $^1$H NMR (CDCl$_3$) δ7.56 (m, 2H), 7.26 (m, 5H), 7.13 (m, 2H), 3.85 (m, 1H), 3.62 (m, 1H), 3.48 (m, 1H), 2.93 (m, 1H), 2.82-2.60 (m, 4H), 2.29 (m, 2H), 1.88-1.25 (m, 7H); MS 491.5 (M+1).

Step B: 4-{3-[2-(3-Hydroxy-4-phenyl-butyl)-5-oxo-pyrrolidin-1-yl]-propyl}-benzonitrile. Analogous to the procedure described for Example 1A, Step E, 4-(3-{2-[3-(tert-butyl-dimethyl-silanyloxy)-4-phenyl-butyl]-5-oxo-pyrrolidin-1-yl}-propyl)-benzonitrile (257.6 mg, 0.525 mmol) was deprotected with TBAF (1M in THF, 0.79 mL, 0.79 mmol) over 24 h. Purification by medium pressure chromatography (1:1 EtOAc: hexanes to EtOAc to 1% MeOH in CH$_2$Cl$_2$ to 3% MeOH in CH$_2$Cl$_2$) provided 4-{3-[2-(3-hydroxy-4-phenyl-butyl)-5-oxo-pyrrolidin-1-yl]-propyl}-benzonitrile (157.8 mg). $^1$H NMR (CDCl$_3$) δ7.56 (m, 2H), 7.26 (m, 7H), 3.80 (m, 1H), 3.67-3.55 (m, 2H), 2.98 (m, 1H), 2.80 (m, 1H), 2.65 (t, 2H), 2.43-2.24 (m, 2H), 2.08 (m, 1H), 1.89-1.33 (m, 9H); MS 375.3 (M−1).

Step C: 5-(3-Hydroxy-4-phenyl-butyl)-1-{3-[4-(2H-tetrazol-5-yl)-phenyl]-propyl}-pyrrolidin-2-one. Analogous to the procedure described for Example 4A, Step E, 4-{3-[2-(3-hydroxy-4-phenyl-butyl)-5-oxo-pyrrolidin-1-yl]-propyl}-benzonitrile (157.8 mg, 0.419 mmol) was reacted with azidotrimethylsilane (0.11 mL, 0.84 mmol) and dibutyltin oxide (20 mg, 0.08 mmol) in toluene (8.6 mL) heated under reflux for 60 h. Purification by medium pressure chromatography (CH$_2$Cl$_2$ to 2% MeOH in CH$_2$Cl$_2$ to 4% MeOH in CH$_2$Cl$_2$ to 6% MeOH in CH$_2$Cl$_2$) provided 5-(3-hydroxy-4-phenyl-butyl)-1-{3-[4-(2H-tetrazol-5-yl)-phenyl]-propyl}-pyrrolidin-2-one (144.7 mg). $^1$H NMR (CDCl$_3$) δ8.02 (m, 2H), 7.27 (m, 7H), 3.84 (m, 1H), 3.67 (m, 2H), 3.10 (m, 1H), 2.84 (m, 1H), 2.67 (m, 2H), 2.53 (m, 1H), 2.42 (m, 1H), 2.14 (m, 1H), 1.97-1.40 (m, 9H); MS 420.3 (M+1), 418.3 (M−1).

Preparation 1 5-[3-(2R-Hydroxymethyl-5-oxo-pyrrolidin-1-yl)-propyl]-thiophene-2-carboxylic acid methyl ester Step A: 5R-(tert-Butyl-dimethyl-silanyloxymethyl)-1-prop-2-ynyl-pyrrolidin-2-one. To a solution of 5R-(tert-butyl-dimethyl-silanyloxymethyl)-pyrrolidin-2-one (Tetrahdedron: Asymmetry, 1996, 7, 2113) (10.24 g, 44.6 mmol) in DMF (650 mL) at 0° C. was added NaHMDS (1M in THF, 49 mL, 49 mmol) dropwise. The reaction mixture was mechanically stirred at room temperature for 2 h to yield a thick suspension. The reaction mixture was cooled to 0° C. and propargyl bromide (80% in toluene, 5.0 mL, 45 mmol) in DMF (50 mL) was added slowly. The reaction mixture was stirred at 0° C. for 2 h and at room temperature for 0.5 h. Aqueous saturated ammonium chloride (700 mL) and water (300 mL) were added. The solution was washed with EtOAc (3×600 mL). The organic solutions were combined, washed with water (4×300 mL) followed by brine (1×300 mL). The organic solution was dried ($Na_2SO_4$), filtered and concentrated. Purification by medium pressure chromatography (10% EtOAc in hexanes to 25% EtOAc in hexanes) provided 5R-(tert-butyl-dimethyl-silanyloxymethyl)-1-prop-2-ynyl-pyrrolidin-2-one (9.85 g). $^1$H NMR ($CDCl_3$) δ4.58 (dd, 1H), 3.88 (m, 1H), 3.77 (dd, 1H), 3.70 (d, 1H), 3.61 (m, 1H), 2.50-2.28 (m, 2H), 2.18 (m, 1H), 2.10 (m, 1H), 1.86 (m, 1H), 0.87 (s, 9H), 0.05 (s, 6H); MS 268.2 (M+1).

Step B: 5-{3-[2R-(tert-Butyl-dimethyl-silanyloxymethyl)-5-oxo-pyrrolidin-1-yl]-prop-1-ynyl}-thiophene-2-carboxylic acid methyl ester. A mixture of 5R-(tert-butyl-dimethyl-silanyloxymethyl)-1-prop-2-ynyl-pyrrolidin-2-one (8.64 g, 32.3 mmol), 5-bromo-thiophene-2-carboxylic acid methyl ester (7.5 g, 33.9 mmol), CuI (308 mg, 1.62 mmol), tetrakis(triphenylphosphine)palladium(0) (1.9 g, 1.62 mmol), triethylamine (5.0 mL, 36 mmol), and $CH_3CN$ (300 mL) was heated under reflux for 19 h. The reaction mixture was cooled to room temperature and the volatiles were removed in vacuo. The residue was dissolved in EtOAc (500 mL) and the organic solution was washed with water (3×200 mL) followed by brine (1×200 mL). The organic solution was dried ($Na_2SO_4$), filtered and concentrated. Purification by medium pressure chromatography (10% EtOAc in hexanes to 25% EtOAc in hexanes) (2 times) provided 5-{3-[2R-(tert-butyl-dimethyl-silanyloxymethyl)-5-oxo-pyrrolidin-1-yl]-prop-1-ynyl}-thiophene-2-carboxylic acid methyl ester (11.42 g). $^1$H NMR ($CDCl_3$) δ7.61 (d, 1H), 7.09 (d, 1H), 4.81 (d, 1H), 3.98 (d, 1H), 3.87 (m, 1H), 3.85 (s, 3H), 3.78 (dd, 1H), 3.63 (dd, 1H), 2.49-2.29 (m, 2H), 2.11 (m, 1H), 1.82 (m, 1H); 0.85 (s, 9H), 0.03 (s, 6H); MS 408.0 (M+1).

Step C: 5-{3-[2R-(tert-Butyl-dimethyl-silanyloxymethyl)-5-oxo-Pyrrolidin-1-yl]-propyl}-thiophene-2-carboxylic acid methyl ester. A mixture of 5-{3-[2R-(tert-butyl-dimethyl-silanyloxymethyl)-5-oxo-pyrrolidin-1-yl]-prop-1-ynyl}-thiophene-2-carboxylic acid methyl ester (11.4 g, 28 mmol) in EtOH (200 mL) was hydrogenated on a Parr shaker at 50 psi in the presence of 10% palladium on carbon (1.2 g) for 3 h. The catalyst was removed by filtration through Celite® with the aid of EtOH and the organic solution was concentrated in vacuo. The hydrogenation was repeated using EtOH (200 mL) and 10% palladium on carbon (1.2 g) at 50 psi for 24 h. Purification by medium pressure chromatography (25% EtOAc in hexanes to 50% EtOAc in hexanes) provided 5-{3-[2R-(tert-butyl-dimethyl-silanyloxymethyl)-5-oxo-pyrrolidin-1-yl]-propyl}-thiophene-2-carboxylic acid methyl ester (10.2 g). $^1$H NMR ($CDCl_3$) δ7.64 (d, 1H), 6.83 (d, 1H), 3.87 (s, 3H), 3.64 (m, 3H), 3.13 (m, 1H), 2.86 (t, 2H), 2.51-2.24 (m, 2H), 2.12-1.78 (m, 4H), 0.88 (s, 9H), 0.04 (s, 6H).

Step D: 5-[3-(2R-Hydroxymethyl-5-oxo-pyrrolidin-1-yl)-propyl]-thiophene-2-carboxylic acid methyl ester. To a solution of 5-{3-[2R-(tert-butyl-dimethyl-silanyloxymethyl)-5-oxo-pyrrolidin-1-yl]-propyl}-thiophene-2-carboxylic acid methyl ester (1.5 g, 3.64 mmol) in MeOH (40 mL) was added 1N HCl (18 mL) and the reaction mixture was stirred for 1.5 h. The volatiles were removed in vacuo and the aqueous solution was washed with $CH_2Cl_2$ (3×50 mL). The organic solutions were combined, washed with brine, dried ($MgSO_4$), filtered and concentrated. Purification by medium pressure chromatography (5% MeOH in $CH_2Cl_2$) provided 5-[3-(2R-hydroxymethyl-5-oxo-pyrrolidin-1-yl)-propyl]-thiophene-2-carboxylic acid methyl ester (689 mg). $^1$H NMR ($CDCl_3$) δ7.59 (d, 1H), 6.79 (d, 1H), 3.82 (s, 3H), 3.75 (m, 1H), 3.62 (m, 3H), 3.07 (m, 1H), 2.82 (t, 2H), 2.44 (m, 1H), 2.26 (m, 2H), 2.09-1.83 (m, 4H); MS 298.2 (M+1).

Preparation 2 7-(2R-Hydroxymethyl-5-oxo-pyrrolidin-1-yl)-heptanoic acid ethyl ester Analogous to the procedure described for Preparation 1, Step A, the anion derived from 5R-(tert-butyl-dimethyl-silanyloxymethyl)-pyrrolidin-2-one (18.83 g, 82.1 mmol) and NaHMDS (1M in THF, 90 mL, 90 mmol) was alkylated with ethyl 7-bromoheptanoate (16 mL, 82 mmol). The reaction mixture was stirred at 60° C. for 16 h and was worked-up analogous to that described for Preparation 1, Step A. The crude residue was dissolved in MeOH (600 mL) and 1N HCl (300 mL) was added. The solution was stirred for 3 h and the volatiles were removed in vacuo. The aqueous solution was diluted with $CH_2Cl_2$ (300 mL) and the organic solution was washed with water (2×75 mL) followed by brine (1×75 mL). The organic solution was dried ($Na_2SO_4$), filtered and concentrated. Purification by medium pressure chromatography (EtOAc) provided 7-(2R-hydroxymethyl-5-oxo-pyrrolidin-1-yl)-heptanoic acid ethyl ester (21.2 g). $^1$H NMR ($CDCl_3$) δ4.12 (q, 2H), 3.80 (dd, 1H), 3.66 (m, 3H), 2.97 (m, 1H), 2.54-2.27 (m, 5H), 2.04 (m, 2H), 1.67-1.28 (m, 8H), 1.26 (t, 3H); MS 272.3 (M+1).

Preparation 3 7-(2R-Hydroxymethyl-5-oxo-pyrrolidin-1-yl)-heptanenitrile

Analogous to the procedure described for Preparation 1, Step A, the anion derived from 5R-(tert-butyl-dimethyl-silanyloxymethyl)-pyrrolidin-2-one (20 g, 87 mmol) and NaHMDS (1M in THF, 96 mL, 96 mmol) was alkylated with 7-bromoheptanenitrile (13 mL, 87 mmol). The reaction mixture was stirred at 60° C. for 24 h and was worked-up analogous to that described for Preparation 1, Step A. The crude residue was dissolved in MeOH (350 mL) and 1N HCl (154 mL) was added. The solution was stirred for 2 h and the volatiles were removed in vacuo. The aqueous solution was washed with $CH_2Cl_2$ (3×200 mL) and the organic solutions were combined and washed with brine (1×150 mL). The organic solution was dried ($Na_2SO_4$), filtered and concentrated. Purification by medium pressure chromatography (1% MeOH in EtOAc to 4% MeOH in EtOAc) provided 7-(2R-hydroxymethyl-5-oxo-pyrrolidin-1-yl)-heptanenitrile (10.3 g). $^1$H NMR ($CDCl_3$) δ3.76 (dd, 1H), 3.62 (m, 3H), 2.97 (m, 1H), 2.43 (m, 1H), 2.33-1.94 (m, 5H), 1.92 (m, 1H), 1.66-1.41 (m, 6H), 1.30 (m, 2H); MS 225.3 (M+1).

Preparation 4 4-(3-Bromo-propyl)-benzoic acid methyl ester

Step A: 4-(3-Hydroxy-prop-1-ynyl)-benzoic acid methyl ester. To a solution of methyl 4-iodobenzoate (20 g, 76 mmol), propargyl alcohol (5.55 g, 99.0 mmol) and triethylamine (20 mL) in acetonitrile (200 mL) was added dichlorobis(triphenylphosphine)palladium(II) (1.55 g, 2.21 mmol), followed by CuI (454 mg, 2.38 mmol). The reaction mixture was stirred at room temperature for 24 h. Water was added and the aqueous solution was washed with EtOAc (3×). The organic solutions were combined, dried ($MgSO_4$), filtered and concentrated. Purification by medium pressure chromatography (9:1 hexanes:EtOAc to 4:1 hexanes:EtOAc) provided 4-(3-hydroxy-prop-1-ynyl)-benzoic acid methyl ester (12.65 g).

Step B: 4-(3-Hydroxy-propyl)-benzoic acid methyl ester. A solution of 4-(3-hydroxy-prop-1-ynyl)-benzoic acid methyl ester (12.65 g) in EtOAc (75 mL) and MeOH (75 mL) was hydrogenated at 50 psi on a Parr shaker in the presence of 10% palladium on carbon (2 g) for 24 h. The catalyst was removed by filtration through Celite® and the filtrate was concentrated. The reaction was repeated by adding 10% palladium on carbon (2 g) and hydrogenating on a Parr shaker for 24 h. After filtering through Celite®, the solution was concentrated in vacuo to provide 4-(3-hydroxy-propyl)-benzoic acid methyl ester (11.98 g).

Step C: 4-(3-Bromo-propyl)-benzoic acid methyl ester. A solution of 4-(3-hydroxy-propyl)-benzoic acid methyl ester (11.98 g) and 1,1'-carbonyldiimidazole (9.0 g, 55.50 mmol) in $CH_3CN$ (200 mL) was stirred at room temperature for 1.5 h. Allyl bromide (20 mL) was added and the reaction mixture was heated under reflux for 20 h. The reaction mixture was cooled to room temperature and saturated aqueous $NaHCO_3$ was added. The aqueous solution was washed with EtOAc (3×) and the organic solutions were combined, dried ($MgSO_4$), filtered and concentrated. Purification by medium pressure chromatography (9:1 hexanes:EtOAc) provided the title compound of Preparation 4.

Preparation 5 2-[3-(2R-Hydroxymethyl-5-oxo-pyrrolidin-1-yl)-propyl]-thiazole-4-carboxylic acid ethyl ester Step A: 2-Bromo-thiazole-4-carboxylic acid ethyl ester. A cold solution of sodium nitrite (228 mg, 3.31 mmol) in water (2.0 mL) was added dropwise to a mixture of 2-amino-thiazole-4-carboxylic acid ethyl ester (J. Am. Chem. Soc., 1946, 68, 266) (500 mg, 2.90 mmol), $CuSO_4$ pentahydrate (2.100 g, 8.41 mmol), NaBr (1.134 g, 11.02 mmol), $H_2SO_4$ (3.0 mL) and water (3.0 mL) at −5° C. to 0° C. The reaction mixture was stirred at 0° C. for 20 minutes and at room temperature for 1 h. The reaction mixture was adjusted to pH 9 with 1N NaOH (105 mL) and the aqueous solution was washed with $CHCl_3$ (4×50 mL). The organic solutions were combined, dried ($MgSO_4$), filtered and concentrated. Purification by medium pressure chromatography (39:1 hexanes:EtOAc to 19:1 hexanes:EtOAc) provided 2-bromo-thiazole-4-carboxylic acid ethyl ester (257 mg).

Step B: 2-{3-[2R-(tert-Butyl-dimethyl-silanyloxymethyl)-5-oxo-pyrrolidin-1-yl]-prop-1-ynyl}-thiazole-4-carboxylic acid ethyl ester. Substituting the appropriate starting materials, the compound of Step B was prepared using an analogous procedure to that described for Preparation 4, Step A using tetrakis(triphenylphosphine)palladium(0) and CuI as catalysts.

Step C: 2-{3-[2R-(tert-Butyl-dimethyl-silanyloxymethyl)-5-oxo-pyrrolidin-1-yl]-propyl}-thiazole-4-carboxylic acid ethyl ester. Substituting the appropriate starting materials, the compound of Step C was prepared using an analogous procedure to that described for Preparation 4, Step B.

Step D: 2-[3-(2R-Hydroxymethyl-5-oxo-pyrrolidin-1-yl)-propyl]-thiazole-4-carboxylic acid ethyl ester. To a solution of 2-{3-[2R-(tert-butyl-dimethyl-silanyloxymethyl)-5-oxo-pyrrolidin-1-yl]-propyl}-thiazole-4-carboxylic acid ethyl ester (306 mg, 0.717 mmol) in THF (20 mL) at 0° C. was slowly added $Bu_4NF$ (1M in THF, 1.1 mL, 1.1 mmol). The reaction mixture was warmed to room temperature and was stirred for 2 h. Aqueous saturated $NaHCO_3$ was added and the volatiles were concentrated in vacuo. The aqueous solution was washed with $CHCl_3$ (4×10 mL). The organic solutions were combined, dried ($MgSO_4$), filtered and concentrated to provide the title compound of Preparation 5 (225 mg).

Preparation 6 [3-(4-Fluoro-3-methyl-phenyl)-2-oxo-propyl]-phosphonic acid diethyl ester Step A: [3-(4-Fluoro-3-methyl-phenyl)-2-hydroxy-propyl]-phosphonic acid diethyl ester. To a solution of 4-fluoro-3-methylphenylmagnesium bromide (0.5M in $Et_2O$, 15.5 mL, 7.75 mmol) in THF (10 mL) at −30° C. was added CuI (196 mg, 1.03 mmol) and the reaction mixture was stirred for 10 minutes. The reaction mixture was warmed to −15° C. and oxiranylmethyl-phosphonic acid diethyl ester (1 g, 5.2 mmol) in THF (10 mL) was added. The reaction mixture was stirred at 0° C. for 2 h. Saturated aqueous ammonium chloride was added and the product was extracted into EtOAc. The organic solution was dried ($MgSO_4$), filtered and concentrated. Purification by medium pressure chromatography (20% EtOAc in hexanes to 70% EtOAc in hexanes) provided [3-(4-fluoro-3-methyl-phenyl)-2-hydroxy-propyl]-phosphonic acid diethyl ester (1.37 g).

Step B: [3-(4-Fluoro-3-methyl-phenyl)-2-oxo-propyl]-phosphonic acid diethyl ester. To a solution of [3-(4-fluoro-3-methyl-phenyl)-2-hydroxy-propyl]-phosphonic acid diethyl ester (1.37 g, 4.51 mmol) in $CH_2Cl_2$ (30 mL) was added Dess-Martin reagent (Chemical Abstracts No. 87413-04-0, 2.10 g, 4.96 mmol). The reaction mixture was stirred at room temperature for 2 h and additional $CH_2Cl_2$ was added. The organic solution was washed with $NaHCO_3$ (2 times) and once with brine. The organic solution was dried ($MgSO_4$), filtered and concentrated. Purification by medium pressure chromatography (20% EtOAc in hexanes to 70% EtOAc in hexanes) provided the title compound of Preparation 6 (1.1 g).

Preparation 7 [3-(3-Methoxymethyl-phenyl)-2-oxo-propyl]-phosphonic acid diethyl ester Substituting the appropriate starting materials, the title compound of Preparation 7 was prepared following an analogous procedure to that described for Preparation 6.

Preparation 8 [3-(4-Ethyl-phenyl)-2-oxo-propyl]-phosphonic acid diethyl ester

Substituting the appropriate starting materials, the title compound of Preparation 8 was prepared following an analogous procedure to that described for Preparation 6.

Preparation 9 {3-[3-(2-Methoxy-ethyl)-phenyl]-2-oxo-propyl}-phosphonic acid diethyl ester Substituting the appropriate starting materials, the title compound of Preparation 9 was prepared following an analogous procedure to that described for Preparation 6.

Preparation 10 [2-Oxo-3-(3-trifluoromethyl-phenyl)-propyl]-phosphonic acid dimethyl ester Step A: N-Methoxy-N-methyl-2-(3-trifluoromethyl-phenyl)-acetamide. To a solution of N,O-dimethylhydroxylamine hydrochloride (1.577 g, 16.2 mmol) in DMF (25 mL) and $CH_2Cl_2$ (25 mL) at 0° C. was added triethylamine (2.25 mL). After stirring for 5 minutes, 3-trifluoromethylphenyl acetic acid (3.0 g, 14.7 mmol), HOBT (3.177 g, 23.5 mmol), and EDC (3.10 g, 16.2 mmol) were added. The reaction mixture was stirred at room temperature for 18 h and was concentrated in vacuo. The residue was diluted with EtOAc and the organic solution was washed consecutively with 1N NaOH (2 times), water, and brine. The organic solution was dried ($MgSO_4$), filtered and concentrated in vacuo. Medium pressure chromatography (20% EtOAc in hexanes to 50% EtOAc in hexanes) provided N-methoxy-N-methyl-2-(3-trifluoromethyl-phenyl)-acetamide.

Step B: [2-Oxo-3-(3-trifluoromethyl-phenyl)-propyl]-phosphonic acid dimethyl ester. To a solution of dimethyl methylphosphonate (9.4 g, 75.8 mmol) in toluene (80 mL) at −78° C. was slowly added n-BuLi (2.5M in hexanes, 28 mL, 70 mmol). The reaction mixture was stirred for 1 h and a solution of N-methoxy-N-methyl-2-(3-trifluoromethyl-phenyl)-acetamide (14.39 g) in toluene (50 mL) was slowly added. The reaction mixture was stirred for 2.5 h and AcOH (40 mL) was added. The reaction mixture was warmed to room temperature and water was added. The organic layer was washed with water followed by brine. The organic solution was dried (MgSO$_4$), filtered and concentrated in vacuo. Medium pressure chromatography (CH$_2$Cl$_2$ to 2% MeOH in CH$_2$Cl$_2$) provided the title compound of Preparation 10 (9.37 g). $^1$H NMR (CDCl$_3$) δ7.52 (m, 1H), 7.44 (m, 2H), 7.37 (m, 1H), 3.96 (s, 2H), 3.87 (s, 3H), 3.76 (S, 3H), 3.12 (d, 2H).

Preparation 11 [3-(3-Chloro-phenyl)-2-oxo-propyl]-phosphonic acid dimethyl ester Substituting the appropriate starting materials, the title compound of Preparation 11 was prepared following an analogous procedure to that described for Preparation 10.

Preparation 12 [3-(3-Bromo-phenyl)-2-oxo-propyl]-phosphonic acid dimethyl ester

Substituting the appropriate starting materials, the title compound of Preparation 12 was prepared following an analogous procedure to that described for Preparation 10.

Preparation 13 [2-Oxo-3-(3-trifluoromethoxy-phenyl)-propyl]-phosphonic acid dimethyl ester Substituting the appropriate starting materials, the title compound of Preparation 13 was prepared following an analogous procedure to that described for Preparation 10. MS 327.1 (M+1), 325.1 (M−1).

Preparation 14 [3-(3-Chloro-phenyl)-2-oxo-propyl]-phosphonic acid dimethyl ester To a solution of dimethyl methylphosphonate (17.93 g, 144 mmol) in THF (270 mL) at −78° C. was slowly added n-BuLi (2.5M, 64.2 mL, 160.6 mmol). The reaction mixture was stirred for 1 h and (3-chloro-phenyl)-acetic acid methyl ester (26.93 g, 146 mmol) was slowly added. The reaction mixture was allowed to warm to room temperature and was stirred for 24 h. Acetic acid (15 mL) was added and the volatiles were removed in vacuo. The residue was diluted with CH$_2$Cl$_2$ and the organic solution was washed carefully with saturated aqueous NaHCO$_3$ (3 times). The organic layer was dried (MgSO$_4$), filtered and concentrated in vacuo. Purification by medium pressure chromatography (20% EtOAc in hexanes to EtOAc) provided the title compound (9.28 g).

Preparations 15–24

Substituting the appropriate starting materials, the following phosphonates (Preparations 15–24) were prepared in an analogous fashion to the procedure described for Preparation 14.

Preparation 15: [3-(3-Fluoro-phenyl)-2-oxo-propyl]-phosphonic acid dimethyl ester Preparation 16: [3-(4-Fluoro-phenyl)-2-oxo-propyl]-phosphonic acid dimethyl ester Preparation 17: [3-(4-Chloro-phenyl)-2-oxo-propyl]-phosphonic acid dimethyl ester Preparation 18: (3-Naphthalen-2-yl-2-oxo-propyl)-phosphonic acid dimethyl ester Preparation 19: (2-Oxo-3-thiophen-2-yl-propyl)-phosphonic acid dimethyl ester Preparation 20: (3-Cyclohexyl-2-oxo-propyl)-phosphonic acid dimethyl ester Preparation 21: (2-Oxo-3-phenyl-propyl)-phosphonic acid dimethyl ester Preparation 22: (3-Benzo[1,3]dioxol-5-yl-2-oxo-propyl)-phosphonic acid dimethyl ester Preparation 23: [2-Oxo-3-(3-phenoxy-phenyl)-propyl]-phosphonic acid dimethyl ester Preparation 24: [2-Oxo-3-(2-trifluoromethyl-phenyl)-propyl]-phosphonic acid dimethyl ester Preparation 25 (3-Biphenyl-3-yl-2-oxo-propyl)-phosphonic acid dimethyl ester Step A: Biphenyl-3-yl-acetic acid methyl ester. A mixture of phenylboronic acid (1.000 g, 8.20 mmol), methyl 3-bromophenylacetate (1.691 g, 7.38 mmol), Na$_2$CO$_3$ (1.738 g, 16.4 mmol), tetrakis(triphenylphosphine) palladium(0) (0.474 g, 0.41 mmol), toluene (30 mL), and water (5 mL) was heated under reflux for 20 h. The reaction mixture was diluted with water (20 mL) and the volatiles were removed in vacuo. The aqueous solution was washed with EtOAc (4×20 mL). The organic solutions were combined, washed with 1N NaOH (15 mL) followed by water (15 mL). The organic solution was dried (MgSO$_4$), filtered and concentrated in vacuo. Purification by medium pressure chromatography (79:1 hexanes:EtOAc to 39:1 hexanes:EtOAc) provided biphenyl-3-yl-acetic acid methyl ester (1.316 g).

Step B: (3-Biphenyl-3-yl-2-oxo-propyl)-phosphonic acid dimethyl ester. The title compound of Preparation 25 was prepared from biphenyl-3-yl-acetic acid methyl ester of Step A following an analogous procedure as described for Preparation 14.

Preparation 26 Tetrahydro-pyrrolizine-3,5-dione

The title compound of Preparation 26 was prepared following the procedure described in U.S. Pat. No. 4,663,464.

What is claimed is:

1. A compound of the formula I

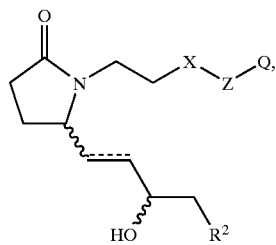

a prodrug thereof, a pharmaceutically acceptable salt of said compound or said prodrug or a stereoisomer or diastereomeric mixture of said compound, prodrug or salt, wherein:
the dotted line is a bond or no bond;
X is O;
Z is phenyl;
Q is carboxyl, $(C_1-C_4)$alkoxylcarbonyl or tetrazolyl;
$R^2$ is Ar;
Ar is Cyclohexyl, 1,2benxodioxolyl, napthyl or phenyl;
wherein said Ar moeity is optionally substituted with one or two $(C_1-C_4)$alkyl, $(C_1-C_4)$alkoxy, $(C_1-C_4)$alkoxy$(C_1-C_4)$alkyl,chloro, fluoro, phenoxy, phenyl or cyano; wherein said $(C_1-C_4)$alkyl, $(C_1-C_4)$alkoxy, or $(C_1-C_4)$alkoxy$(C_1-C_4)$alkyl substituents in the definition of Ar are optionally substituted on carbon with one to three fluoro.

2. A method of treating a condition which presents with low bone mass in a mammal comprising administering to said mammal a compound of claim 1, a prodrug thereof or a pharmaceutically acceptable salt of said compound or of said prodrug, or a diastereomeric mixture of said compound, salt or prodrug.

3. A method of claim 2 wherein said condition is osteoporosis, frailty, an osteoporotic fracture, a bone defect, childhood idiopathic bone loss, alveolar bone loss, mandibular bone loss, bone fracture, osteotomy, bone loss associated with periodontitis, or prosthetic ingrowth.

4. A method of claim 3 wherein said composition is administered systemically.

5. A method of claim 3 wherein said composition is administered locally.

6. A method of claim 3 wherein said condition is frailty.

7. A method of claim 3 wherein said condition is osteoporosis.

8. A method of claim 3 wherein said condition is bone fracture or osteoporotic fracture.

9. A pharmaceutical composition comprising a compound of claim 1, a prodrug thereof, a pharmaceutically acceptable salt of said compound or said prodrug or a stereoisomer or diastereomeric mixture of said compound, prodrug or salt, wherein and a pharmaceutically acceptable carrier, vehicle or diluent.

10. A method of treating a condition which presents with low bone mass in a mammal comprising administering to said mammal a pharmaceutical composition of claim 9.

11. A compound according to claim 1, wherein said compound is 4-{2-[2-(3-Hydroxy-4-phenyl-butyl)-5-oxo-pyrrolidin-1-yl]-ethoxy}-benzoic acid.

* * * * *